United States Patent
Thompson et al.

(10) Patent No.: US 6,197,258 B1
(45) Date of Patent: Mar. 6, 2001

(54) PHOTOLUMINESCENT SENSORS OF CHEMICAL ANALYTES

(75) Inventors: Richard B. Thompson, Baltimore; Vincent L. Feliccia, Arnold; Badri P. Maliwal, Baltimore, all of MD (US); Carol A. Fierke, Durham, NC (US)

(73) Assignee: University of Maryland, Baltimore, Baltimore, MD (US)

(*) Notice: Subject to any disclaimer, the term of this patent is extended or adjusted under 35 U.S.C. 154(b) by 0 days.

(21) Appl. No.: 09/273,303

(22) Filed: Mar. 19, 1999

Related U.S. Application Data

(63) Continuation-in-part of application No. 09/071,351, filed on Apr. 30, 1998, and a continuation-in-part of application No. 08/736,904, filed on Oct. 25, 1996, now Pat. No. 5,952,236.
(60) Provisional application No. 60/078,597, filed on Mar. 19, 1998, and provisional application No. 60/083,868, filed on May 1, 1998.

(51) Int. Cl.[7] .............................. G01N 33/20; C12Q 1/00
(52) U.S. Cl. .................. 422/82.07; 422/68.1; 422/82.05; 422/82.06; 422/82.08; 435/4; 435/18; 436/73; 436/80; 436/81; 530/350; 530/412
(58) Field of Search ..................................... 530/350, 412; 436/73, 74, 77, 80, 81; 422/68.1, 82.05, 82.06, 82.07, 82.08; 435/4, 18

(56) References Cited

U.S. PATENT DOCUMENTS 5,545,517   8/1996   Thompson et al. .
5,952,236 * 9/1999   Thompson et al. .................... 436/77

OTHER PUBLICATIONS

Thompson, R.B., "Fluorescence–Based Fiber–Optic Sensors" in *Topics in Fluorescence Spectroscopy, vol. 2: Principles*, Lakowicz, J.R. (Ed.) Plenum Press, NY (1991).
Saari, L.A. et al., "pH Sensor Based on Immobilized Fluoresceinamine," *Anal. Chem.* (1982) 54:821–3.
Thompson, R.B., et al., "Chemistry and Technology of Evanescent Wave Biosensors" in *Biosensors with Fiber Optics*, Wise, D. and L. Windgard (Eds.) pp. 111–138, Humana Press, Clifton, NJ (1991).
Tsien, R.Y., "Fluorescent Probes of Cell Signaling," *Ann. Rev. Neurosci.* (1989) 12:227–53.
Opitz, N. et al., Compact $CO_2$ Gas Analyzer with Favourable Signal–to–Noise Ratio and Resolution Using Special Fluorescence Sensors (Optodes) Illuminated by Blue LED's,' *Adv. Exp. Med. Biol.* (1984) 180:757.
Thompson, R.B. et al., "Enzyme–Based Fiber Optic Zinc Biosensor," *Anal. Chem.* (1993) 65:730–4.
Demas, J.N. et al., "Design and Applications of Highly Luminescent Transition Metal Complexes" in *Topics in Fluorescence Spectroscopy, vol. 4: Probe Design and Chemical Sensing*, Lakowicz, J.R. (Ed.) Plenum Press, NY (1994).
Lippitsch, M.E. et al., "Fibre–Optic Oxygen Sensor wih the Fluorescence Decay Time as the Information Carrier," *Anal. Chim. Acta* (1988) 205:1–6.
Keating, S.M. et al., "Nanosecond Fluorescence Microscopy," *Biophys. J.* (1991) 59:186–202.
Szmacinski, H. et al., "Optical Measurements of pH Using Fluorescence Lifetimes and Phase–Modulation Fluorometry," *Anal. Chem.* (1993) 65:1668–74.
Lakowicz, J.R., "Fluorescence Lifetime Sensing Generates Cellular Images," *Laser Focus World* (1992) 28(5):60–80.
Thompson, R.B. et al., "Fluorescence Lifetime–Based Sensing of Zinc in Solution," in *Proc. of the SPIE Conference on Chemical, Biochemical, and Environmental Fiber Optic Sensors V*, Lieberman, R.A. (Ed.) pp. 296–306 (1994) Bellingham, WA.
Ozinskas, A.J., et al., "Homogeneous Model Immunoassay of Thyroxine by Phase–Modulation Fluorescence Spectroscopy," *Anal. Biochem.* (1993) 213:264–270.
T.M. Eads et al., "Microsecond Rotational Motions of Eosin–labeled Myosin Measured by Time–resolved Anisotropy of Absorption and Phosphores–cence" *J. Mol. Biol* (1984) 179:55–81.
Thompson et al., "Performance Enhancement of Fluorescence Energy Transfer–Based Bio–sensors by Site–Directed Mutagenesis of the Transducer"*J. Biomed. Opt.* (1996), 1(1):131–7.
Lindskog, S. et al., "Carbonic Anhydrase," in *The Enzymes*, vol. 5, Third Ed. (P.D. Boyer, Ed.) pp. 587–665 (1971).
Thompson, R.B. et al., "Energy transfer–based fiber optic metal ion biosensor," *Proc. SPIE Conf. Advances in Fluorescence Sensing Technology* vol. 2388, (Lakowicz, J.R., ed.), pp. 138–147 (1995).
Thompson, R.B. et al., "Fiber optic biosensor for Co(II) and Cu(II) based on fluorescence energy transfer with an enzyme transducer," *Biosensors& Bioelectronics*, (1996) 11(6/7):557–64.

(List continued on next page.)

Primary Examiner—Arlen Soderquist
(74) Attorney, Agent, or Firm—Chalin A. Smith; David L. Marks

(57) ABSTRACT

The invention described in detail herein relates to the detection, determination, and quantitation of certain ions and small molecules in solution. The invention specifically relates to improvements in the area of photoluminescent sensors for use in a detection scheme involving the alteration of a photoluminescent label or moiety attached to or associated with an analyte binding macromolecule. One may use the changes in photoluminescence lifetime, changes in ratios of photoluminescence intensity or changes in photoluminescence polarization (anisotropy) to determine the analyte. The photoluminescence change measured correlates to the concentration of the ion or molecule in solution.

6 Claims, 44 Drawing Sheets

OTHER PUBLICATIONS

Thompson, R.B. et al., "Determination of Picomolar Concentrations of Metal Ions Using Fluorescence Anisotropy: Biosensing with a 'Reagentless' Enzyme Transducer," *Analytical Chemistry* (1998) 70:4717–23.

Nair, S.K. et al., "Unexpected pH–Dependent Conformation of His–64, the Proton Shuttle of Carbonic Anhydrase II," *JACS* (1991) 113:9455–8.

Kiefer,, L.L. et al., "Hydrogen Bond Network in the Metal Binding Site of Carbonic Anhydrase Enhances Zinc Affinity and Catalytic Efficiency," *JACS* (1995), 117:6831–7.

Hunt, J.B. et al., "A Rapid and Convenient Preparation of Apocarbonic Anhydrase," *Anal Biochem* (1997) 79:614–7.

Thompson, R.B. et al., "Selectivity and Sensitivity of Fluorescence Lifetime–Based Metal Ion Biosensing Using a Carbonic Anhydrase Transducer," *Analytical Bio–chemistry* (1999) 267:185–95.

J. D. Stewart et al, J. Am. Chem. Soc. 1994, 116, 415–416, Jan. 1994.*

R. B. Thompson et al, Anal. Biochem. 1995, 227, 123–128, 1995.*

D. Elbaum et al, J. Am. Chem. Soc. 1996, 118, 8381–8387, 1996.*

E. Kimura et al, Chem. Soc. Rev. 1998, 27, 179–184, 1998.*

Hunt, J.A. et al., "Metal Binding Specificity in Carbonic Anhydrase is Influenced by Conserved Hydrophobic Core Residues," *Biochemistry* 38:9054–62 (1999).

* cited by examiner-

STRUCTURE FOR O-6034

OREGON GREEN® 488 MALEIMIDE

MOLECULAR FORMULA: $C_{24}H_{11}F_2NO_7$

MOLECULAR WEIGHT: 463.35

PHOTOLUMINESCENT SENSORS OF CHEMICAL ANALYTES

CROSS-REFERENCE TO RELATED APPLICATIONS

This application claims priority to U.S. Provisional Application Serial No. 60/078,597 filed Mar. 19, 1998, and U.S. Provisional Application Serial No. 60/083,868 filed May 1, 1998, the contents of which are incorporated herein. In addition, this application is a continuation-in-part of U.S. patent application Ser. No. 09/071,351 filed Apr. 30, 1998 and U.S. patent application Ser. No. 08/736,904 filed Oct. 25, 1996, now U.S. Pat. No. 5,952,236, issued Sep. 14, 1999, the contents of which are incorporated herein.

ACKNOWLEDGEMENTS

The development of the present invention was supported by the University of Maryland, Baltimore, the Office of Naval Research under grant number N00014-91-1572 and the National Science Foundation under grant number BES-9613556. The United States Government has a non-exclusive, irrevocable, paid-up license to practice or have practiced for or on behalf of the United States the invention herein as provided for by the terms of the above mentioned contracts awarded by the United States Government.

FIELD OF THE INVENTION

The field of this invention generally relates to the detection, determination, and quantitation of certain ions and small molecules in solution. The field more specifically relates to improvements in the area of photoluminescent sensors for use in combination with a detection scheme involving changes in the photoluminescence of a photoluminescent moiety, said moiety either free in solution or associated with an analyte binding macromolecule. The change of photoluminescence may be manifested by changes in photoluminescence lifetime, changes in ratios of photoluminescence intensity or changes in photoluminescence polarization (anisotropy). The photoluminescence change measured correlates to the concentration of the ion or molecule in solution.

BACKGROUND OF THE INVENTION

For scientific, regulatory, or other applications, many persons, institutions, and agencies often require analyses of samples to determine whether such small molecule and ionic analytes are present. Examples of such analyses include the determination of metal ions in sea water to understand the processes of chemical oceanography; determination of toxic materials such as $Hg(II)$, $Ni(II)$, $CN^-$, or $HS^-$ in groundwater or wastewater; detection of the corrosion of metal alloys by the presence of $Co(II)$, $Zn(II)$, or $Cu(II)$ in condensates; or the presence of metals in lubricating oil as an indicator of machinery wear and incipient failure.

Many methods are known in the art for such analyses. For metal ions, such methods include graphite furnace atomic absorption spectrophotometry, inductively coupled plasma atomic emission spectroscopy and mass spectroscopy, various electrochemical means, and photoluminescence spectroscopy using metallo-photoluminescent indicators. For common anionic analytes there are fewer techniques available; they include ion chromatography, mass spectrometry, and electrochemical means.

Most of these techniques involve analysis of single or multiple discrete samples in a specialized instrument which may not be close to the sample. This is a particular drawback for analytical tasks that require a continuous or quasi-continuous determination of the analyte with real time readout of the result; require samples to be collected from remote, inaccessible, or hazardous environments; or require such extensive sampling that it is prohibitively costly. For many of these methods a sensor capable of remotely, continuously, and selectively monitoring the analyte of interest in situ is required, and subsequent reporting of the results of the analysis back to the operator in real time.

Improvements have been made in the development of photoluminescence-based sensors for a variety of applications (Thompson, R. B. (1991) in *Topics in Fluorescence Spectroscopy*, Vol. 2: *Principles*, Lakowicz, J. R. (Ed.) Plenum Press, NY; Wolfbeis, O. S. (Ed.) (1992) *Fiber Optic Chemical Sensors and Biosensors* Vols. I and II, CRC Press, Boca Raton, Fla.; Lakowicz, J. R., and Thompson, R. B. (Eds.) (1993) *Proc. of the SPIE Conference on Advances in Fluorescence Sensing Technology* Vol. 1885, Society of Photooptical Instrumentation Engineers, Bellingham, Wash.) A central issue in the development of such sensors has been the means of transduction, whereby the presence or relative amount of the chemical analyte is transduced as a change in the photoluminescence which may be quantitated. Thus, workers in the field have mainly transduced analyte levels as changes in photoluminescence intensity (Thompson (1991); Saari, L. A., and Seitz, W. R. (1982) *Anal. Chem.* 54, 821; Thompson, R. B. and Ligler, F. S. (1991) in *Biosensors with Fiber Optics.*, Wise, D., and Wingard, L. (Eds.) pp. 111–138, Humana Press, Clifton, N.J.), or ratios of photoluminescence intensity at two different wavelengths (wavelength ratiometric) (Tsien, R. Y. (1989) *Ann. Rev. Neurosci.* 12, 227; Opitz, N., and Lubbers, D. W. (1984) *Adv. Exp. Med. Biol.* 180, 757; Thompson, R. B. and Jones, E. R. (1993) *Anal. Chem.* 65, 730–4; and U.S. Pat. No. 5,545,517).

The ratio approach has proven particularly popular because it is robust in avoiding many of the artifacts which limit the accuracy and precision of simple intensity measurements. The major limitation of the ratio approach has been the limited number of ratiometric photoluminescent indicators (Haugland, R. P. (1992) *Handbook of Fluorescent Probes and Research Chemicals*, Molecular Probes, Eugene, Oreg.).

Intensity based methods, however, are sensitive to artifacts, as any change in photoluminescence intensity, regardless of its origin may be misinterpreted as a change in concentration. Changes in light scattering, or variations in excitation light intensity and/or photobleaching may easily be misinterpreted as a change in the concentration of the metal ion. Although the accuracy and precision of these methods may be improved through the use of internal photoluminescent standards, or with the monitoring of excitation intensity or with the use of kinetic methods of analysis, careful and even repeated calibration of reagents and instrumentation are required to minimize spurious variations in signal intensity.

Recently, many groups have shown that transducing the level of analyte as a change in photoluminescence lifetime is a robust and flexible approach to optical sensing (Demas, J. N., (1994) in *Topics in Fluorescence Spectroscopy*, Vol. 4: *Probe Design and Chemical Sensing*, Lakowicz, J. R. (Ed.) Plenum Press, NY; Lippitsch, M. E., Pusterhofer, J., Leiner, M. J. P. and Wolfbeis, O. S. (1988) *Anal. Chim. Acta* 205, 1–6; Keating, S. M., and Wensel, T. G. (1991) *Biophys. J.* 59, 186–202; Lakowicz, J. R., Szmacinski, H., and Karakelle, M. (1993) *Anal. Chim. Acta* 272, 179–186; Szmacinski, H., and Lakowicz, J. R. (1993) *Anal. Chem.* 65, 1668–74; Lakowicz, J. R. (1992) Laser Focus World 28(5) 60–80; Thompson, R. B. and Patchan, M. W. (1993) in *Proc. of the SPIE Conference on Chemical, Biochemical, and Environmental Fiber Optic Sensors V.* Lieberman, R. A. (Ed.) pp. 296–306. Society of Photooptical Instrumentation Engineers, Bellingham, Wash.; Ozinskas, A. J., Malak, H., Joshi, J., Szmacinski, H., Britz, J., Thompson, R. B., Koen, P. A., and Lakowicz, J. R. (1993) *Anal. Biochem.* 213, 264–270). Lifetime-based sensing can exhibit a dynamic range of greater than five orders of magnitude in analyte concentration (Szmacinski, H., and Lakowicz, J. R. (1993) *Anal. Chem.* 65, 1668–74; Thompson, R. B. and Patchan, M. W. (1993) in *Proc. of the SPIE Conference on Chemical, Biochemical, and Environmental Fiber Optic Sensors V.* Lieberman, R. A. (Ed.) pp. 296–306. Society of Photooptical Instrumentation Engineers, Bellingham, Wash.). Lifetime-based sensing has been adapted to and has particular advantages for fiber optic sensors.

Photoluminescence resonance energy transfer is a dipole-dipole interaction described by Förster (Förster, Th. (1948) *Ann. Physik* 2, 55–75) that is very useful for lifetime-based sensing. Förster's theory is very well-established, with thousands of examples in the literature of its predictive power. The rate of energy transfer $K_T$ is a function of the distance between donor and acceptor r, the refractive index of the medium n, the degree of energy overlap J between the emission spectrum of the donor and the absorbance spectrum of the acceptor, the emissive rate of the donor in the absence of acceptor $I_d$, and the relative orientation between the donor and acceptor dipoles $k^2$:

$$K_T = (r^{-6} J k^2 n^{-4} I_d) \times 8.71 \times 10^{23} \text{ sec}^{-1}$$

The rate of energy transfer can be simply expressed in terms of a Förster distance $R_0$, which is the distance at which the rates of emission and energy transfer are equal, and the lifetime of the donor τ (tau):

$$K_T = \frac{1}{\tau_D} \left( \frac{R_0}{r} \right)^6$$

Although, lifetime and ratiometric methods are qualitatively similar with respect to their freedom from spurious variations in photoluminescence intensity, the physical measurement of photoluminescence lifetime is costlier and technically more difficult than a simple intensity measurement, especially in the context of imaging applications. Regardless of these drawbacks, lifetime analysis has been preferred for reasons that include its broad dynamic test range in sample concentrations which may exceed five orders of magnitude in some cases. Lifetime-based analysis also minimizes errors associated with optics, fluorophore concentration and detector sensitivity.

In the '351 patent application identified above, we have introduced the use of photoluminescence polarization (anisotropy) for the detection and quantitative analysis of metal ions in aqueous solutions. It is simply predicated on the use of a photoluminescent indicator system that will emit polarized light in a measurably different manner on the formation of a macromolecule-metal ion complex. This complex may rely on either the metal dependent binding of a photoluminescent indicator to a macromolecule, or the binding of a metal ion to a macromolecule that has previously been labeled with a photoluminescent label. Thus, using the teachings described in our previous patent application, one can detect and quantitate metal ions in solution by a homogeneous photoluminescence polarization (anisotropy) assay based on proximity dependent quenching mechanisms and other means, and not simply to a change in the rotational correlation time of the fluorescent label.

A labeled macromolecule such as carbonic anhydrase, wherein the donor fluorophore is approximately at its Förster distance from a suitable metal in the active site, would exhibit a more rapid apparent decay of its photoluminescence due to energy transfer; energy transfer is thus a quenching mechanism, and a decrease in photoluminescence intensity should be observed as well. It is well known that by placing the donor much closer to the active site, essentially quantitative quenching results, whereas if the donor is much further away, the quenching is modest due to the sixth power dependence. Additionally, we have identified certain embodiments that exhibit metal-dependent fluorescence quenching which cannot be due to Förster transfer and which therefore quench by other proximity-dependent mechanisms. These embodiments, described in greater detail below, include but are not limited to photoluminescent sensors for lifetime sensing of cadmium and zinc comprised of the N67C variant of carbonic anhydrase variant labeled with ABD-T or ABD-F.

In the '904 application mentioned above, we first demonstrated that positioning of the photoluminescent donor moiety on the macromolecule at particular distances from a metal ion bound to the macromolecule or an inhibitor bound to the metal ion optimizes the response of the assay. Thus, a sensor, which we term "photoluminescence-based biosensor", can transduce the presence or level of the metal ion or ligand as a change in the photoluminescence of an indicator phase, which can be measured through a length of optical fiber with the indicator phase at the distal end in contact with a sample containing the metal ion or ligand at the proximal end. Our previous applications demonstrated that the determination of metal ions and ligands such as anions using a photoluminescent energy transfer mechanism employing a macromolecule. We also demonstrated the importance of controlling the proximity of the photoluminescent-donor-label to the metal ion or ligand in making the determinations.

The invention herein, described in detail below, is directed to new and improved photoluminescence-based biosensors for use in the photoluminescence detection methods described in co-pending patent applications recited above. These detection methods include change in intensity, wavelength, polarization, and lifetime (time-dependance) of the emission.

SUMMARY OF THE INVENTION

Accordingly, an object of the present invention is to provide improved photoluminescent sensors for determining the presence of and quantifying chemical analytes such as metal ions and ligands.

More particularly, it is an object of the present invention to provide a series of novel and improved photoluminescent molecules having superior properties, such as broad dynamic range and large intensity increase, for use as photoluminescent labels to be covalently or non-covalently bound to an analyte binding macromolecule, said labeled macromolecule having particular use as a photoluminescent sensor. The said labeled macromolecule may indicate the presence or amount of a ligand or metal ion analyte utilizing photoluminescence intensity lifetime, ratiometric, or anisotropy sensing techniques. In addition to those we have previously disclosed, such photoluminescent labels include non-covalent labels 7-fluorobenz-2-oxa-1,3,-diazole-4- sulfonamide+beta-mercaptoethanol adduct (ABD-M or ABD-S); 7-fluorobenz-2-oxa-1,3,-diazole-4-sulfonamide:ethanolamine adduct (ABD-N); Dapoxyl sulfonamide; benzothioazolyl coumarin sulfonamide (BTCS) as well as covalent labels 7-(5-maleimidyl)-pentylaminobenz-2-oxa-1,3,-diazole4-sulfonamide (ABD-T); PyMPO; and Oregon Green™ 488 maleimide (1-[[(2', 7'-difluoro-3',6'-dihydroxy-3-oxospiro[isobenzofuran-1 (3H), 9'-[9H]xanthen]-5-yl)carbonyl]oxy]-2,5-pyrrolidinedione, CA index name).

It is a further object of the present invention to provide a series of novel and improved macromolecules having superior properties, such as analyte specificity or selectivity or accelerated reactivity or stability, for use as analyte binding molecule having particular use as a photoluminescent sensors. The photoluminescence may stem from the inherent photoluminescence of the macromolecule itself or from a photoluminescent label bound thereto. The sensor may be used in a variety of sensing approaches utilizing photoluminescence lifetime, ratiometric, or anisotropy sensing techniques. Such analyte binding macromolecules include variants of human carbonic anhydrase II such as F131C, N67C, E117A, E117D, E117Q, and Q92A. Herein, we use the generally accepted nomenclature widely used in the art for the naming of variants. Specifically, we use the standard single letter code, wherein the first letter and number denote the identity and residue number (position) of the amino acid in the wild type carbonic anhydrase molecule and the last letter denotes the identity of the amino acid replacing it in the sequence.

DETAILED DESCRIPTION OF THE INVENTION

Figure 1:
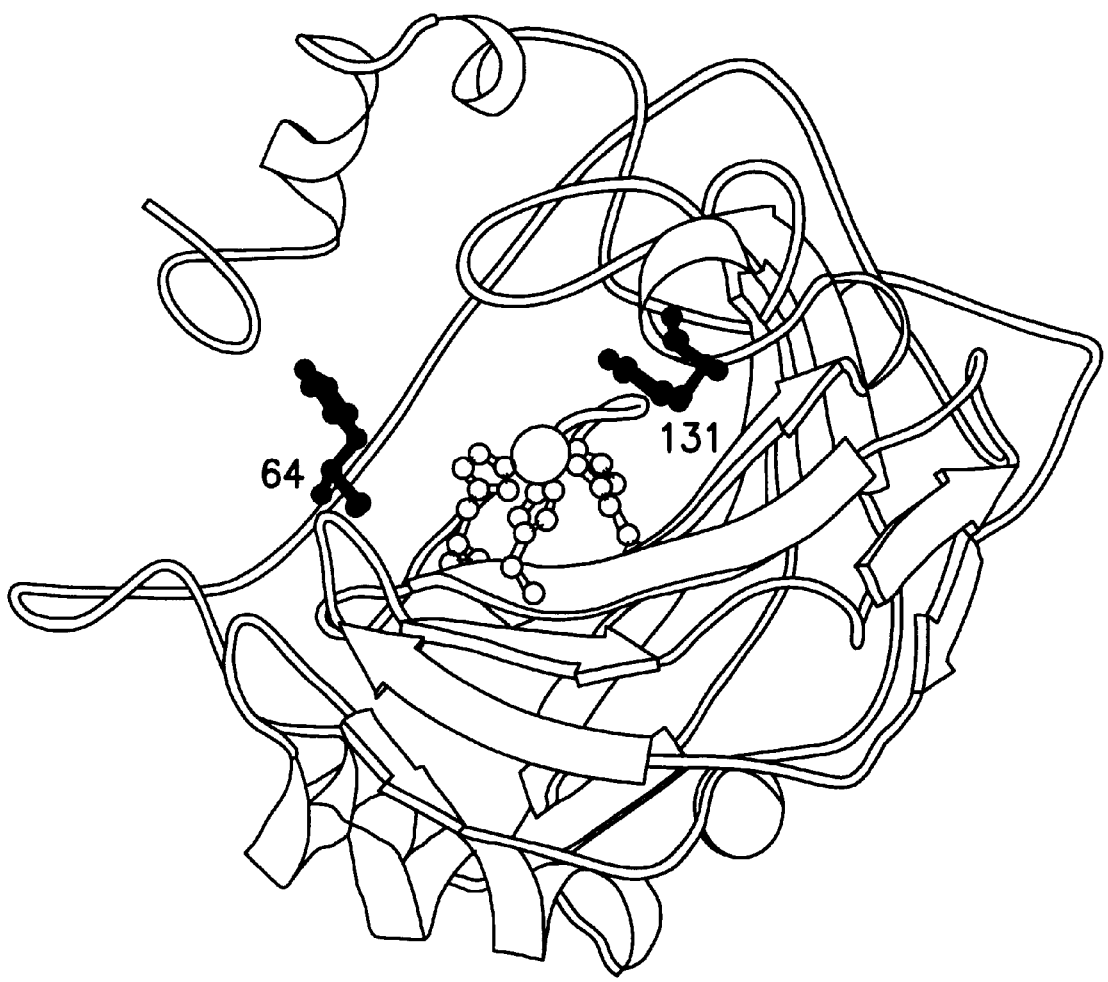
FIG. 1 shows human carbonic anhydrase II. Residues replaced with cysteine (F131C and H64C) and the active site Zn (II) (large ball) are highlighted.

For convenience, the meaning of certain terms and phrases employed in the specification, examples and appended claims are provided below.

"Ligand" broadly refers to molecules capable of binding to a macromolecule under certain conditions, such as in the presence of a metal ion bound to the same macromolecule. Such a ligand may be photoluminescent and/or it may be an inhibitor of the macromolecule if the macromolecule is an enzyme.

"Macromolecule" as used herein, is meant to refer to a composition which has a molecular weight typically of more than about 5 kD and is typically a polymer made of two or more monomeric units. Macromolecules can be polypeptides, proteins, nucleic acids, polysaccharides, carbohydrates, lipids or other organic (carbon containing) or inorganic molecules.

"Photoluminescence" is herein defined as the emission of light by a sample, molecule, label or a material upon illumination by light, specifically to include fluorescence and phosphorescence. A label may be attached to the macromolecule covalently or non-covalently, or the macromolecule may be intrinsically photoluminescent, as in the frequent case of a protein containing tyrosine or tryptophan. The term further refers to any of a group of processes whereby a material is excited by radiation such as light, raised to an excited electronic or vibronic state, and subsequently re-emits that excitation energy as a photon of light. These processes include fluorescence, which denotes emission accompanying descent from an excited state with paired electrons (a "singlet" state) or unpaired electrons (a "triplet" state) to a lower state with the same multiplicity; a quantum-mechanically "allowed" transition. Photoluminescence also includes phosphorescence, which denotes emission accompanying descent from an excited triplet or singlet state to a lower state of different multiplicity; a quantum mechanically "forbidden" transition. Compared to "allowed" transitions, "forbidden" transitions are associated with relatively longer excited state lifetimes. Additionally, photoluminescent processes include emission from metal to ligand charge transfer excited states; the multiplicity of which is ill-defined or unknown. However, for all these photoluminescent processes polarization (anisotropy) measurements are well known in the art (Lakowicz (1983) and Eads, T. M., D. D. Thomas and R. H. Austin (1984) J. Mol. Biol. 179, 55–81). Thus we construe measurements of photoluminescence anisotropy described herein specifically to include measurements of phosphorescence anisotropy, photoluminescence anisotropy and other photoluminescence from or to states of indeterminate multiplicity.

"Polarization," which is used interchangeably with "anisotropy," refers to measurements of the polarization of photoluminescence made according to the classic methods of Jablonski, Perrin, and Weber (see below for a fuller discussion). These two terms are simply related mathematically and measure the same phenomenon, but normalize the difference in light intensities measured through orthogonally oriented emission polarizers in a different fashion.

"Polarized light" refers to linearly polarized light, which is ideally what is employed in the art. However, as a practical matter elliptically-polarized light may also be used.

The particular macromolecule is not critical to the general practice of the invention, as long as a suitable photoluminescent label is bound either covalently or non-covalently, the photoluminescent label is optimally positioned with respect to the metal or ligand binding site, and a metal ion or ligand binding site is present. Macromolecules useful in the present invention include, but are not limited to, proteins. Examples include carbonic anhydrase II, alkaline phosphatase, leucine aminopeptidase, carboxypeptidase, laccase, azurin, and urease. Most preferable is carbonic anhydrase II. Specific variants of carbonic anhydrase described in our related applications include cysteine-substituted forms, such as serine-166, histidine-36, histidine-64, histidine-97, tyrosine-7, valine-143, and leucine-198. Such enzyme variants can be produced by well known methods. One of the advantages of using a binding site incorporated in a macromolecule scaffold such as carbonic anhydrase is that by the use of such site-directed mutagenesis approaches the donor may be placed an ideal distance from the acceptor in the active site. In general, this cannot be done with non-macromolecule binding materials. We have described quantitatively the approach for positioning such donors when utilizing as transduction means Förster energy transfer, (Thompson, et al. *J. Biomed. Opt.*, 1(1), 131–137 (1996)) and find that the preferable distance is about 0.75 times the $R_0$, the Förster distance where energy transfer is 50% efficient. For other proximity-dependent transduction means such as electron transfer, intersystem crossing promoted by spin-orbit coupling, and quenching by paramagnetic species, the optimal position of the label with respect to the metal ion means or ligand may be different, and is to a degree predictable on the basis of theories well known to the art.

While the use of wild type or variants of human carbonic anhydrase II is generally preferred, alternative embodiments within the scope of this invention include, but are not limited to other human carbonic anhydrase isozymes; carbonic anhydrases from other species such as cow and spinach; other metalloenzymes including alkaline phosphatases, leucine aminopeptidases, carboxypeptidases, laccases, azurins, and ureases from diverse species; other metallo-enzymes for which inhibitor binding is metal-dependent or which bind metals exhibiting charge transfer or d-d absorption bands, mutants and variants of the above enzymes; biological, biomimetic, organic and inorganic polymers; metal-binding reagents, nucleic acids, polysaccharides, carbohydrates and nonbiological polymers have been described in our previously filed patent applications.

Though the particular macromolecule is not critical to the performance of the general practice of the methods described previously, certain macromolecules have recently been determined to be unexpectedly superior, particularly in combination with particular photoluminescent labels or moieties or particular measurement techniques or a combination thereof. Specifically, the cysteine-substituted forms of carbonic anhydrase F131C and N67C have demonstrated superior properties in the area of reactivity and stability. Additionally, the carbonic anhydrase variants E117A, E117D, E117Q, and Q92A have demonstrated superior properties in the area of metal binding kinetics and have been dubbed "fast variants."

Many photoluminescent labels may be selected based upon the metal ion, ligand, and/or mechanism of quenching as set forth herein. Many photoluminescent labels are known in the art (R. P. Haugland and K. Larison, Handbook of Fluorescent Probes 1994–5, Molecular Probes, Eugene, Oreg.). Many other photoluminescent labels are disclosed in the literature, as well as the intrinsic tyrosyl and tryptophanyl photoluminescence of the protein, and phosphorescent labels are considered within the scope of this present invention. Photoluminescent ligand species previously disclosed include: 4-aminosulfonyl [1-(4-N-(5-fluoresceinylthioureido)butyl)]benzamide; 7-fluorobenz-2-oxa-1,3-diazole-4-sulfonamide(ABD-F); dansylamide; hydroxynapthalene-sulphonamide; 2-(3-methoxy-4-ethoxyphenyl)-4-chloroquinoline-6-sulfonamide; N-(1-anthracenyl)-4-sulfonamido-benzenesulfonamide; ethyl-2-(4-sulfonamidophenyl)-4-hydroxyquinoline-6-carboxylate; N-(N'-(4'-sulfamoylglutaranily-amidoethyl))-4-amino-3,6-disulfo-1,8-naphthalimide; fluorescein isothiocyanate; rhodamine iodoacetamide; CY3 iodoacetamide; Green Fluorescent Protein; morpholinorhodamine iodoacetamide; pyrene propylmaleimide; nitrobenzooxazolyl chloride; CY5-iodoacetamide, 4-sulfobenzoxazolyl fluoride; mono-bromobimane; bodipyiodoacetamide; dansyl aziridine; 4-chloro-7-sulfobenzofuran (SBF); and nitrobenzoxadiazolyl.

Though the particular photoluminescent molecule is not critical to the general practice of the methods described previously, certain molecules have recently been determined to be unexpectedly superior, particularly in combination with particular macromolecules or particular measurement techniques or a combination thereof. Such photoluminescent molecules include non-covalent labels 7-fluorobenz-2-oxa-1,3,-diazole-4-sulfonamide+beta-mercaptoethanol adduct (ABD-M or ABD-S), 7-fluorobenz-2-oxa-1,3,-diazole-4-sulfonamide: ethanolamine adduct (ABD-N), dapoxyl sulfonamide and benzothioazolyl coumarin sulfonamide (BTCS) as well as covalent labels 7-(5-maleimidyl)-pentylaminobenz-2-oxa-1,3,-diazole-4-sulfonamide (ABD-T), PyMPO, and Oregon Green™ 488 maleimide.

The ions to be detected by the present invention includes, but is not limited to Zn(II), Co(II), Cd(II), Ni(II), Hg(II), Fe(II), Mn(II), Pb(II), and Cu(II). Other metal ions are known by those skilled in the art which bind to macromolecules with greater or lesser affinity and which alter quench, or dequench or shift photoluminescence themselves or promote the binding of colored inhibitors which can quench the photoluminescence or promote binding of fluorescent ligands.

The measurement can be determined by techniques well known to those skilled in the art, including measuring the change in photoluminescence anisotropy, photoluminescence lifetime, photoluminescence intensity, excitation spectrum of the donor, photoluminescence dichroism, or phosphorescence intensity or lifetime.

Many techniques are known to the art for measuring the time dependence of photoluminescence emission, including streak cameras, time correlated single photon counting, direct measurement of the time resolved photoluminescence, frequency domain fluorometry, upconversion techniques, phase-sensitive detection, boxcar techniques, and the like.

Figure 35:
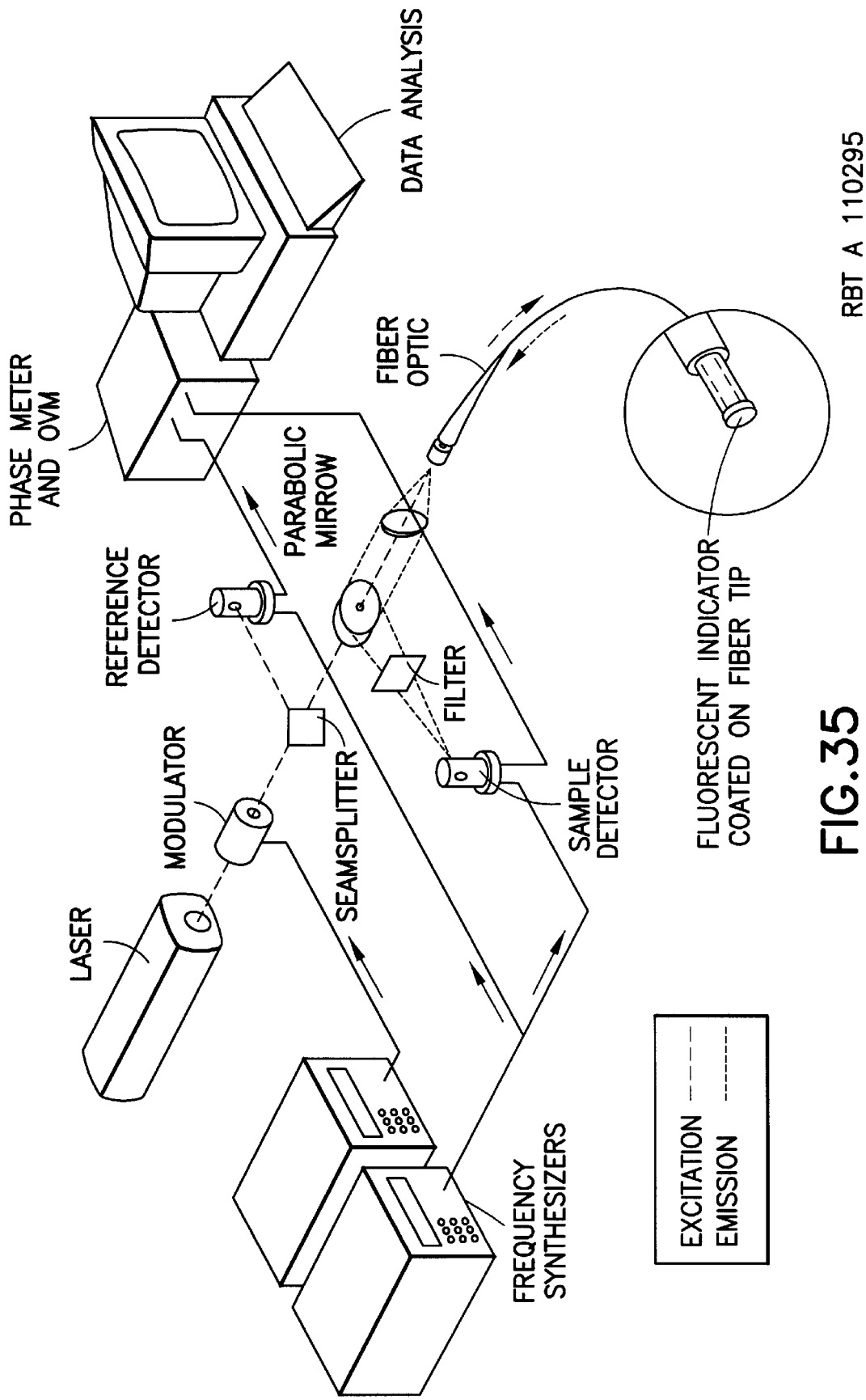
FIG. 35 depicts an apparatus for lifetime based fiber optic biosensors.

Similarly, while lasers as light sources and photomultiplier tubes as detectors have been used, for some applications adequate or improved performance may be achieved by the use of LED's, laser diodes, electroluminescent sources, arc lamps, spark gaps, xenon arc lamps, incandescent lamps, ionizing radiation or other sources. In the same fashion other light detectors may be used, including microchannel plate photomultiplier tubes, photodiodes, avalanche photodiodes, streak cameras, CCD's and other detectors known to the art may be used. The apparatus for lifetime-based fiber optic biosensing is depicted in FIG. 35. Fundamentally, this device is a phase fluorometer adapted for measurements through a length of optical fiber. Excitation from the laser (dashed line) is amplitude modulated at 1–250 MHz by an E-O modulator; a beam splitter takes 5% of the excitation to measure the phase and modulation. The excitation is launched into the fiber optic by the lens whence it excites the fluorophores in the tip coating; the photoluminescence is coupled back into the fiber and exits the proximal end (dotted line). The photoluminescence is reflected off the off-axis parabolic mirror into the detector, which measures its phase and modulation relative to the excitation.

In some embodiments of the present invention, quenching occurs due to proximity of the metal ion or ligand to the photoluminescent donor label or photoluminescent moiety associated with the macromolecule. In some embodiments, this proximity-dependent quenching is facilitated by the use of colored inhibitors. A subset of metal ions which bind to the active site of a macromolecule are transduced via the proximity of a bound colored inhibitor whose binding to the macromolecule they promote. Many inhibitors of the preferred macromolecule carbonic anhydrase are known to the art, including many aryl sulfonamides. These compounds are quantifiable by one of the methods described, and they can be made to exhibit some proximity-dependent photoluminescence quenching. Thus other colored aryl sulfonamide inhibitors known to the art such as 4-(4'dimethylaminophenyl)azophenyl sulfonamide and salicylazobenzensulfonamide are also workable in some circumstances discernable to one of ordinary skill in the art. The use of azosulfamide as a colored ligand bound to the macromolecule is the preferred embodiment when the metal ion to be measured is Co(II), Cd(II), or Zn(II).

Figure 3:
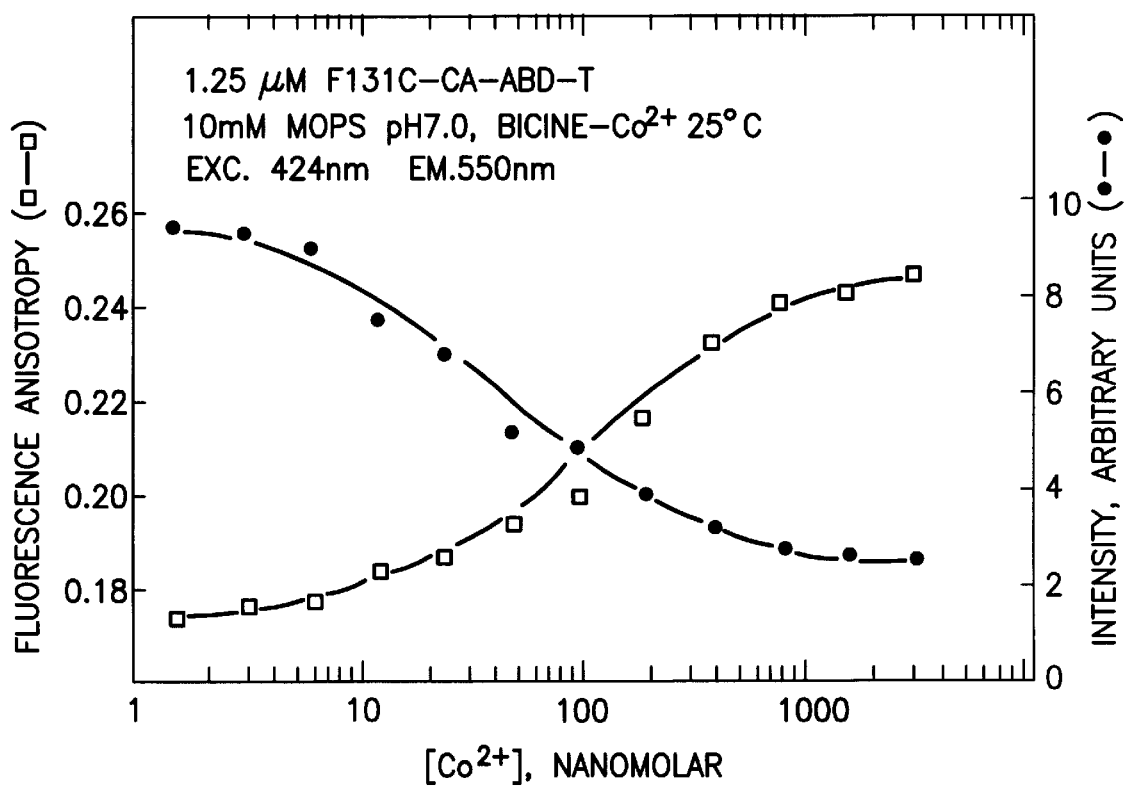
FIG. 3 shows differential polarized-phase fluorometry of ABD-T labelled apo-F131C carbonic anhydrase II in the absence of metal: differential phase angles (■) and modulation ratios (○) are depicted as a function of the frequency.

Other methods of proximity-dependent quenching are utilized depending on the metal ion or ligand to be transduced. Several metals exhibit weak d-d absorbance bands which can undergo characteristic changes upon binding to the active site of the macromolecule. Metals known to do this include Ni(II), Co(II), and Cu(II) (S. Lindskog, L. E. Henderson, K. K. Kannan, A. Liljas, P. O. Nyman, and B. Strandberg, "Carbonic Anhydrase," in *The Enzymes*, Vol. 5, Third Ed. (P. D. Boyer, Ed.) pp. 587–665 (1971)). Such absorbing species can serve as energy transfer acceptors for a photoluminescent donor with suitable position, orientation, and spectral overlap, and thus transduce their binding by the macromolecule as a change in photoluminescence intensity and lifetime of such a donor (FIG. 3). Demonstration of such sensing in solution and through a fiber optic is shown in R. B. Thompson, Z. Ge, M. W. Patchan, and C. A. Fierke, "Energy transfer-based fiber optic metal ion biosensor," Proc. SPIE Conf. Advances in Fluorescence Sensing Technology (SPIE Vol. 2388) (J. R. Lakowicz, ed.), pp. 138–147 (1995); R. B. Thompson, Z. Ge, M. W. Patchan, C.-C. Huang, and C. A. Fierke, Biosensors & Bioelectronics, 11(6/7), pp. 557–564 (1996). In this case no separate colored inhibitor is necessary.

Other metals that do not absorb light but bind to the active site of the macromolecule could also be transduced in this manner in a competition-type assay. Such assays are well known in the art. While the results obtained in the present invention are consistent with the well-established theory of Förster energy transfer, other proximity-dependent quenching processes creating the observed response are envisioned by the present invention and include but are not limited to electron transfer, quenching by paramagnetic species, quenching by intersystem crossing promoted by spin-orbit coupling of high Z atom, and other equivalent processes generally known to those skilled in the art.

While carbonic anhydrase exhibits intrinsic ultraviolet tryptophanyl photoluminescence (like nearly all other proteins), it does not ordinarily emit in the visible regime where the principal d-d absorbance bands are to be found, and there is no observation or measurement of energy transfer to the d-d absorbance band of a suitable metal ion bound to a protein. The lanthanides, Eu(III), Tb(III), Dy(III), Sm(III), can serve as energy transfer acceptors but they do not exhibit d-d absorbance bands perturbed by binding, and we know of no quantitation of lanthanides by this means.

The metallo-macromolecule of the present invention is used in the same manner as described above for the macromolecule. Such metallo-molecules include, but are not limited to, carbonic anhydrases with the d-d absorbing metal ions Cu(II), Co(II), or Ni(II) already bound to the active site. It is to this metallo-molecule that an unknown ligand to be detected is bound.

The ligands to be detected include, but are not limited to $OH^-$, $N_3^{--}$, $CN^-$, $CNO^-$, $NO_3^-$, acetate, formate, $HCO_3^-$, phenolate, dinitrophenolate, $HS^-$, or $NO_3^-$. It is well known to those skilled in the art that many anionic molecules are capable of binding (in some cases as a fourth ligand to the active site metal) to carbonic anhydrases such that they inhibit the activity of the holoenzyme. In the cases of Co(II), Ni(II), and Cu(II) (the latter of which has no activity), the characteristic d-d absorbance spectrum of the metal is perturbed to some degree when anions such as these become bound to the active site. This perturbation of absorbance can be significant, such that for a suitably chosen photoluminescent donor the energy transfer efficiency to the metal may be altered significantly.

Different anions will have different effects depending on their measured perturbations to the absorbance spectrum of the bound metal, which may be predicted on the basis of the well-known theory of Förster energy transfer and the known emission and absorbance spectra. Similarly, the spectral output of the donor can be chosen to maximize the perturbation of energy transfer upon anion binding.

Furthermore, other proximity-dependent quenching effects promoted by a ligand or metal-ion binding may be used and are considered within the scope of the present invention. Such proximity-dependent quenching processes include atom-based quenching, quenching by paramagnetic species, quenching by nitroxide spin labels and other free radicals, and quenching by electron transfer.

As discussed above, certain embodiments of the photoluminescent sensor and system do not function by metal quenching the photoluminescent moiety, either as a covalent label or free in solution, in a proximity dependent manner. Such embodiments, described in greater detail below, include ABD-M and ABD-N in reaction with zinc and ABD-F-N67C in reaction with zinc or cadmium In the subsequent examples, we discuss herein the four most widely used methods for photoluminescence measuring and sensing: lifetime (designated herein by the greek letter, tau or 'τ'); anisotropy or polarization (designated herein by the letter 'r'), intensity (designated herein by the letter 'I') and wavelength shift or ratiometric (designated herein by the letter 'w'). The experiments described below follow one of two distinct sensing techniques, both of which were first described in our co-pending patent applications mentioned at the outset to which this application claims the benefit. For clarity and organizational purposes, we will discuss each embodiment according to the particular scheme in which it is preferred.

Scheme 1: Photoluminescence Sensing with Non-Covalent Labels

In this scheme, the photoluminescence may be measured by any of the known techniques, particularly those described above (lifetime, anisotropy, intensity and wavelength ratiometric). We utilize a macromolecule specifically selected for its analyte binding site as described above. The sample containing an unknown quantity of analyte is placed in an aqueous solution containing a known amount of analyte binding macromolecule and photoluminescent non-covalent label, both free in solution. Typically, the analyte is a metal ion which promotes the binding of the non-covalent label, thereby altering its photoluminescence properties. The photoluminescent properties of the ligand vary from the bound and unbound state. Using such observed changes in photoluminescence, one can calculate the concentration of the analyte in the sample.

In our newly discovered improved embodiments, the preferred macromolecule is a human apocarbonic anhydrase, the most preferred being E117A, E117D, E117Q, and Q9A. These variants have very fast metal-binding kinetics, making them ideal for use in real time sensors. The most preferred moieties or ligands include aryl sulfonamides such as ABD-N, ABD-M, dapoxyl sulfonamide, and BTCS. We have observed that ABD-N and ABD-M are highly useful in combination with all four photoluminescence measuring techniques: lifetime, anisotropy, intensity and wavelength. ABD-M in particular exhibits a broad dynamic range of response. Dapoxyl sulfonamide is primarily useful in lifetime, intensity and wavelength though it has been used with moderate success in anisotropy assays. BTCS exhibits changes in both anisotropy and photoluminescence lifetime. The preferred analytes to be sensed are metal ions, most preferably zinc, with cadmium and cobalt being somewhat less preferred. Unexpectedly, we observed that ABD-N, ABD-M, and dapoxyl sulfonamide are not quenched by some metal ions. Rather, the fluorescence is enhanced or unchanged.

Scheme 2: Photoluminescence Sensing with Covalent Labels

In this scheme, we use changes in photoluminescence to assay for the concentration of a particular analyte, such as a metal ion. We utilize a macromolecule specifically selected for its analyte binding site as described above. The sample containing an unknown quantity of analyte is placed in an aqueous solution containing a known amount of analyte binding macromolecule, said macromolecule having a photoluminescent label covalently bound thereto. In most cases, the binding of the analyte causes the photoluminescence of the label to be quenched in a proximity dependent fashion. In such cases, the lifetime decreases while the anisotropy increases. However, in certain unusual exceptions, such as the case of ABD-F labelled N67C, the fluorescence is enhanced, the lifetime increased, and the anisotropy decreases to varying extents, depending upon the particular metal ion observed. Using observed changes in photoluminescence (lifetime, anisotropy, intensity or wavelength), one can calculate the concentration of the analyte in the sample.

In our newly discovered improved embodiments, the most preferred macromolecule is a human apocarbonic anhydrase, more specifically the variants F131C and N67C. In fact, unexpectedly, labels at F131C are insensitive to weaker binding sites to which N67C responds. The preferred photoluminescent labels include ABD-F, ABD-T ($\tau$, r, I, and w to a lesser extent), PyMPO ($\tau$ and I) and Oregon Green™ ($\tau$ and I). The latter two demonstrate highly useful responses in both lifetime and intensity based assays while the former also show utility as an anisotropy fluorophore. Thus, in the anisotropy technique, the most preferred photoluminescent label is ABD-T. Quite unexpectedly, we observed ABD-T to be quenched by zinc and cadmium as well as copper, cobalt, and nickel. The preferred analytes to be sensed are metal ions, most preferred being cobalt, copper and nickel using a Förster energy transfer quenching mechanism and cadmium and zinc using a non-Förster energy transfer quenching mechanism.

The following further examples detail the superior and unexpected properties of the photoluminescent biosensor components.

F131C Labeled with ABD-T

The embodiment herein reacts by scheme 2 described above. Although the specific results discussed below are directed to anisotropy sensing, it is important to note that F131C-ABD-T can also be utilized in lifetime, intensity, and to a lesser extent wavelength shift based sensing methods. These results are presented in our publication in Analytical Chemistry (volume 70, number 22, pp. 4717–4723, November 1998) which is specifically incorporated by reference in its entirety.

The variant of carbonic anhydrase herein was specifically engineered with a cysteine replacing a residue chosen near the active site. The presence of an exterior cysteine facilitates the attachment of a covalent label. The labeled variant exhibited changes in anisotropy up to 0.07 upon binding free Cu(II), Co(II), and Zn(II) with apparent Kd's close to the values observed with wild type apocarbonic anhydrase. The results demonstrate that free transition metal ions can be determined at trace levels in aqueous solution using inexpensive instruments.

An important advantage of fluorescent labeling the protein covalently as compared with using a diffusible fluorescent inhibitor is that the affinity of the inhibitor for the holoprotein is no longer a matter for concern. For example, the fluorescent aryl sulfonamide ABD-M exhibits a substantial increase in anisotropy upon binding to holocarbonic anhydrase, but its affinity for the holoprotein is rather modest ($K_D$=0.3 uM), whereas the apoenzyme's affinity for Zn(II) is rather high ($K_D$=10 pM). Consequently, at a zinc concentration of 1 nM, an equivalent total concentration of apoprotein would become saturated with zinc; however, only a tiny fraction of the protein would subsequently have ABD-M bound to it at a concentration more than two orders of magnitude below its binding constant.

The F131C variant (FIG. 1) was cloned, expressed, and isolated from *E. coli* strain BL21(DE3)pACA as previously described by Nair (JACS, 113, pp. 9455–9458, 1991) and Kiefer (JACS, 117, pp. 6831–6837, 1995) The variant was labeled in pH 8 borate buffer for 4 hours at room temperature using ABD-T (7-(5-maleimidylpentylamino)benz-2-oxa-1, 3-diazole-4-sulfonamide). Excess reagent was removed by repeated centrifugation in a Centriprep filtration device (Amicon) or passage over a Sephadex G-25 column. ABD-T was custom-synthesized by Molecular Probes. The average number of fluorophores conjugated per protein molecule was 1.0 or less, as determined by spectrophotometry using an extinction coefficient at 430 nanometers of 8000 $M^{-1}$ $cm^{-1}$ for the fluorescent labels and 49,000 $M^{-1}$ $cm^{-1}$ at 280 nanometers for the protein. Zn(II) was removed from some variants as previously described using dipicolinate at pH 6.2 [Hunt, Anal Biochem, 79:614–617, 1977].

All buffers were rendered metal-free by passage over a Chelex-100 column (Bio-RAD). Steady state spectra and anisotropies were measured with a Spectronics AB-2 fluorimeter; lifetimes were measured on an ISS K2 phase fluorimeter using the ultraviolet multiline output of a small frame Ar ion laser (Spectra Physics 2065) and dimethylPOPOP as a reference compound, or the 442 nm line of a Kimmon HeCd laser with Rose Bengal in ethanol as a standard, both as previously described by Thompson (1988). Differential polarized phase fluorometry was performed as described previously, using the HeCd or a frequency-doubled Spectra-Physics Tsunami picosecond laser at 390 nm [Mantulin, 1977] Zn(II) levels were buffered at the indicated levels by the use of NTA at pH 7.0 and 30 C, and Cu(II) levels were similarly buffered at pH 7.0 and 25 C. We note that H64C, especially when fluorescent-labeled in the apo-form, is significantly less stable than other variants we have used, and thus it is important not to expose it to extremes of temperature or concentrate it.

Figure 2:
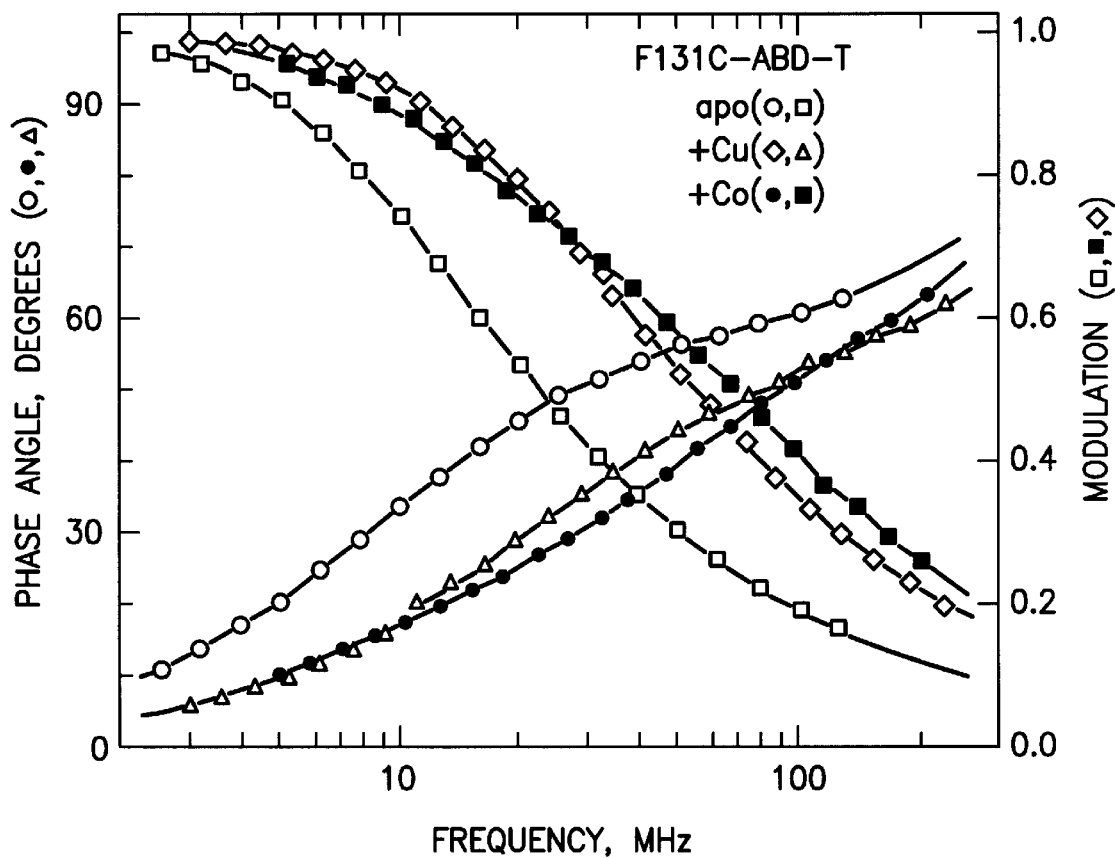
FIG. 2 shows phase shifts (●, ○, Δ) and demodulations (□, ■, ◇) measured for ABD-T labeled apocarbonic anhydrase variant F131C-ABD in the absence of metal (○, □) and in the presence of saturating amounts of copper [Cu(II)] (◇, Δ) and cobalt [Co(II)] (●, ■).

Since carbonic anhydrase has approximately a 15 nanosecond rotational correlation time (based on a rotational relaxation time, $\theta_c$, of 28.9 nsec determined using a Perrin-Weber plot) inspection of the Perrin equation suggests that label lifetimes comparable to the relevant rotational correlation time should result in maximal changes in anisotropy. Thus we sought a label with a lifetime in the 15 nanosecond range which was likely to be partially quenched upon binding to the metal. In fact a form of the sulfonamido benzoxadiazole label we had used previously modified to react selectively with sulfhydryl residues was satisfactory, exhibiting a complex decay with an average lifetime of 12.8 nsec (see Table 1, below) when coupled to position F131C on the protein (FIG. 2).

Figure 4:
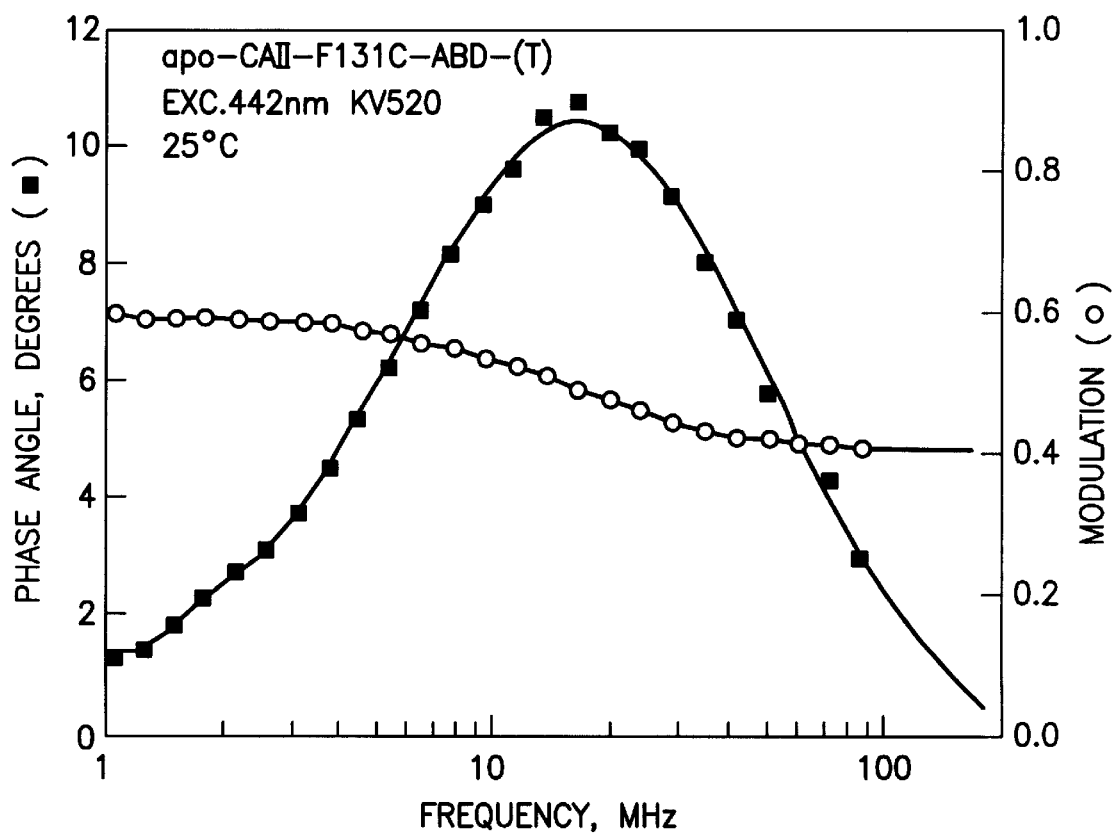
FIG. 4 shows fluorescence intensity (●) and anisotropy (□) of ABD-T labelled apo-F131C carbonic anhydrase II as a function of free copper [Cu(II)] concentration buffered with millimolar concentrations of Bicine. Excitation at 442 nm, emission at 550 nm.
Figure 5:
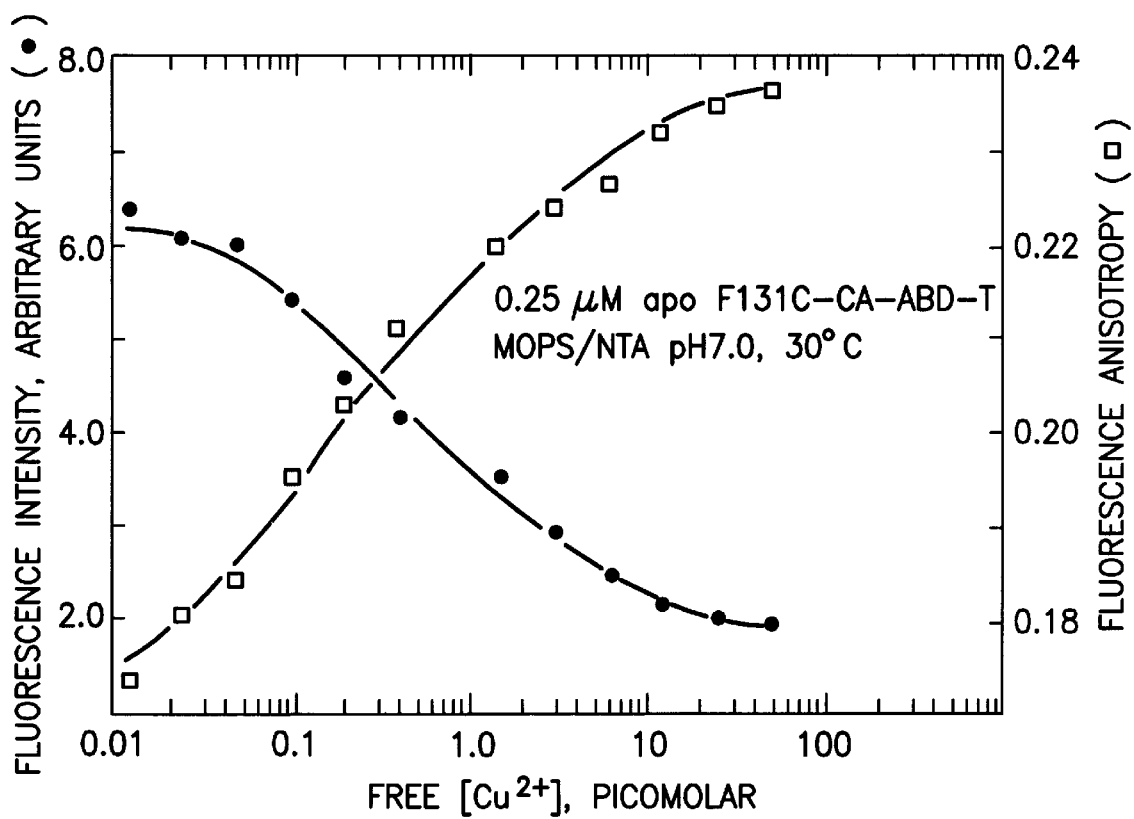
FIG. 5 shows fluorescence intensity (●) and anisotropy (□) of ABD-T labelled apo-F131C carbonic anhydrase II as a function of free cobalt [Co(II)] concentration buffered with NTA at pH of 7.0- by 10 mM MOPS. Excitation at 436 nm, emission at 550 nm.

Differential polarized phase fluorometry (a sensitive probe of rotational motion) of the apo-F131C-ABD(T) conjugate was performed in order to determine if the ABD-(T) label closely followed the rotational motion of the whole protein, or exhibited significant segmental motion independent of the protein. The data (FIG. 3) were well fit by a single rotational correlation time of 14.7 nsec ($x^2$=0.8), with no significant segmental motion. Addition of Co(II) to the apoprotein resulted in quenching of the ABD-T fluorescence intensity to the extent of 70%, which saturated in the micromolar range (FIG. 4). This behavior is consistent with binding of Co(II) to the active site of the enzyme, resulting in partial quenching; by comparison, collisional quenching would not be significant at Co(II) concentrations below micromolar according to the Stern-Volmer relation, nor would it result in saturating behavior. The lifetime of Co(II)-saturated apo-F131C-ABD-T was measured and well fit by three components; the decline in average lifetime (52%, Table 1) was somewhat less than the decline in intensity (70%; FIG. 5), suggesting a modest level of static quenching is present.

TABLE 1

| Variant[a] | $M^{2+}$[b] | $\tau_1$[c] | $f_1$[d] | $\tau_2$[c] | $f_2$[d] | $\tau_3$[c] | $f_3$[d] | $<\tau>$[e] | $x^{2}$[f] |
|---|---|---|---|---|---|---|---|---|---|
| F131C-ABD-T | — | 16.87 | 0.66 | 5.82 | 0.22 | 1.08 | 0.12 | 12.57 | 0.6 |
| | Co | 14.09 | 0.31 | 3.20 | 0.49 | 0.89 | 0.20 | 6.15 | 0.8 |
| | Cu | 8.07 | 0.56 | 2.85 | 0.31 | 0.61 | 0.14 | 5.44 | 0.7 |
| H64C-ABD | — | 10.18 | 0.40 | 2.44 | 0.42 | 0.42 | 0.19 | | 1.4 |
| | Zn | 9.73 | 0.30 | 1.64 | 0.36 | 0.36 | 0.34 | | 1.2 |

[a] "Variant" refers to the variant of labeled apocarbonic anhydrase measured;
[b] "$M^{2+}$" refers to the metal ion added;
[c] "$\tau_i$" and
[d] "$f_i$" refer to the lifetime in nanoseconds and fractional intensity of the $i^{th}$ component, respectively;
[e] $<\tau>$ is the average lifetime in nanoseconds; and
[f] "$x^2$" is the reduced $x^2$, the ordinary criterion for goodness of fit.

The saturation with the analyte resulting in quenching of between 50 and 75% should result in an increase of anisotropy from 0.20 to between 0.27 and 0.31. In the case of apo-F131C-ABD(T), saturation with Co(II) results in an increase in anisotropy from 0.175 to 0.245, a comparable increase (FIG. 4). While the lifetime and rotational correlation times do not exactly match those used in the simulation, nevertheless the agreement is remarkably close, and suggests that even simple simulations are useful in designing biosensor transducers.

Having previously noted that F131C-ABD-T exhibits Cu-dependent decreases in its fluorescence intensity like other carbonic anhydrase variants with fluorescent labels close to the active site, the corresponding fluorescence lifetimes and anisotropies were also measured as a function of free Cu(II) concentration; the results are depicted in FIGS. 2 and 5, respectively. It is apparent that as Cu(II) concentration is increased, the fluorescence lifetime (Table 1) and intensity both decline and the anisotropy increases (FIG. 5). In particular, the intensity declines approximately 75% and the average lifetime declines 60%, and the anisotropy increases from 0.17 to 0.245. No change was observed when the apoprotein was treated with Zn(II) (results not shown), and the decline in lifetime is too large to explain as resulting from trivial collisional quenching, due to the very low concentrations of free Cu(II) present. The anisotropy changes in FIG. 4 are quite usable, and the apparent $K_D$ of the apoprotein as determined by anisotropy (about 2 pM) is approximately 0.5 log unit higher than that previously observed (0.4 pM) in accord with the simulation. We note that care was taken to fully equilibrate the apoenzyme samples in the (very low) concentration of free copper ion present.

It is important to note that variants following fluorescent derivatization retain metal ion affinities comparable to the wild type apoprotein. In this instance, apo-F131C-ABD(T) exhibits affinities for Cu and Co of 0.3 pM and 100 nM, respectively, compared with wild type affinities of 0.4 pM and 50 nM, respectively. While some perturbation has occurred, clearly if the wild type binding site is intact the affinity and selectivity will be largely retained. However, it should be borne in mind that while apo-F131C-ABD(T) displays only modest changes in its fluorescence properties upon the binding of Zn or Cd, these ions nevertheless bind, and thus can interfere with the determination of Cu or Co by this method, if they are sufficiently plentiful.

N67C Labelled with ABD-F and PyMPO

The embodiment herein reacts by scheme 2 described above. Although the specific results discussed below are directed to lifetime sensing, it is important to note that N67C and ABD-F can be utilized in anisotropy, intensity and, to a lesser extent, wavelength shift measurement systems. As mentioned above, PyMPO is primarily useful in measuring by photoluminescence lifetime and intensity. These results are also discussed in our publication in Analytical Biochemistry (volume 267, pp. 185–195, 1999) which is specifically incorporated by reference in its entirety. A cysteine residue is inserted in the sequence replacing the asparagine at position 67 (N67C-CA).

The variant of human carbonic anhydrase II was constructed, cloned, expressed in *E. coli* strain BL21(DE3) pACA, isolated, and purified essentially as described above. N67C-CA protein was labeled with a 10-fold molar excess of ABD-F (7-fluorobenz-2-oxa-1,3-diazole-4-sulfonamide, Molecular Probes cat. No. F-6053, Eugene, Oreg.) dissolved in DMF (final proportion <1%) by incubation for four hours at room temperature in pH 8.0 borate buffer, followed by gel filtration on Sephadex G-10 to remove unreacted reagent.

Significant difficulty was encountered in removal of Zn(II) ion from ABD-labeled N67C (N67C-ABD) using dipicolinic acid, perhaps due to noncovalent binding of residual ABD-F to the Zn(II) ion, or interference with the dipicolinic acid binding to the enzyme. Although the apoenzyme could be labeled, it was considered prudent to label the enzyme with metal bound. In a second embodiment, N67C was labeled with 1-(2-maleimidylethyl)-4-(5-(4-methoxyphenyl) oxazol-2-yl) pyridinium methanesulfonate (PyMPO maleimide: Molecular Probes catalog no. M-6026) in DMF (<2.5% of the final reaction mixture) in borate buffer as above; the degree of conjugation was less than one PyMPO maleimide moiety per CA molecule by spectrophotometry ($\epsilon_{412\ nm}$=23,000 $M^{-1}$ $cm^{-1}$). Buffers were passed over Chelex-100 columns (Bio-Rad), stored in new or acid-washed polyethylene plastic bottles, and handled with metal-free pipet tips (Bio-Rad) to minimize metal ion contamination. Zn(II) and Cu(II) were incubated with apoenzyme for at least several hours to assure complete equilibration; equilibration is much faster with the other metals. Free metal ion concentrations in the nanomolar range and below are difficult to maintain in the absence of metal ion buffers. Thus, the following buffers were used with their respective metal ions: nitrilotriacetic acid (NTA) with Cu(II), Zn(II), and Cd(II); and Bicine with Co(II) and Ni(II). Buffer concentrations were calculated with a spreadsheet program developed by Keith McCall and C. A. F. at Duke University using the known pH-dependent stability constants [Smith, 1973 #14]. All buffers were maintained at pH 7.0 with 10 mM MOPS, which has very modest affinity for the metal ions.

Steady state emission spectra and intensities were measured on a Spectronics AB-2 spectrophotofluorimeter with 8 nm bandpasses, and are uncorrected. Fluorescence intensities were fit to a single binding isotherm using the program Kaleidagraph (Synergy Software). Fluorescence lifetime data were obtained on an ISS K2 multifrequency phase fluorometer using the ultraviolet lines of a Spectra-Physics 2065-7S argon ion laser (100 mW, all lines, for ABD) or a Kimmon He Cd laser for PyMPO-labeled CA (35 mW at 442 nm) for excitation, KV-470 and KV-520 bandpass emission filters for the ultraviolet and blue excitation, respectively and dimethylPOPOP in ethanol or Rose Bengal in ethanol as references. Frequency-dependent phase and modulation data were analyzed using ISS proprietary software.

Figure 6:
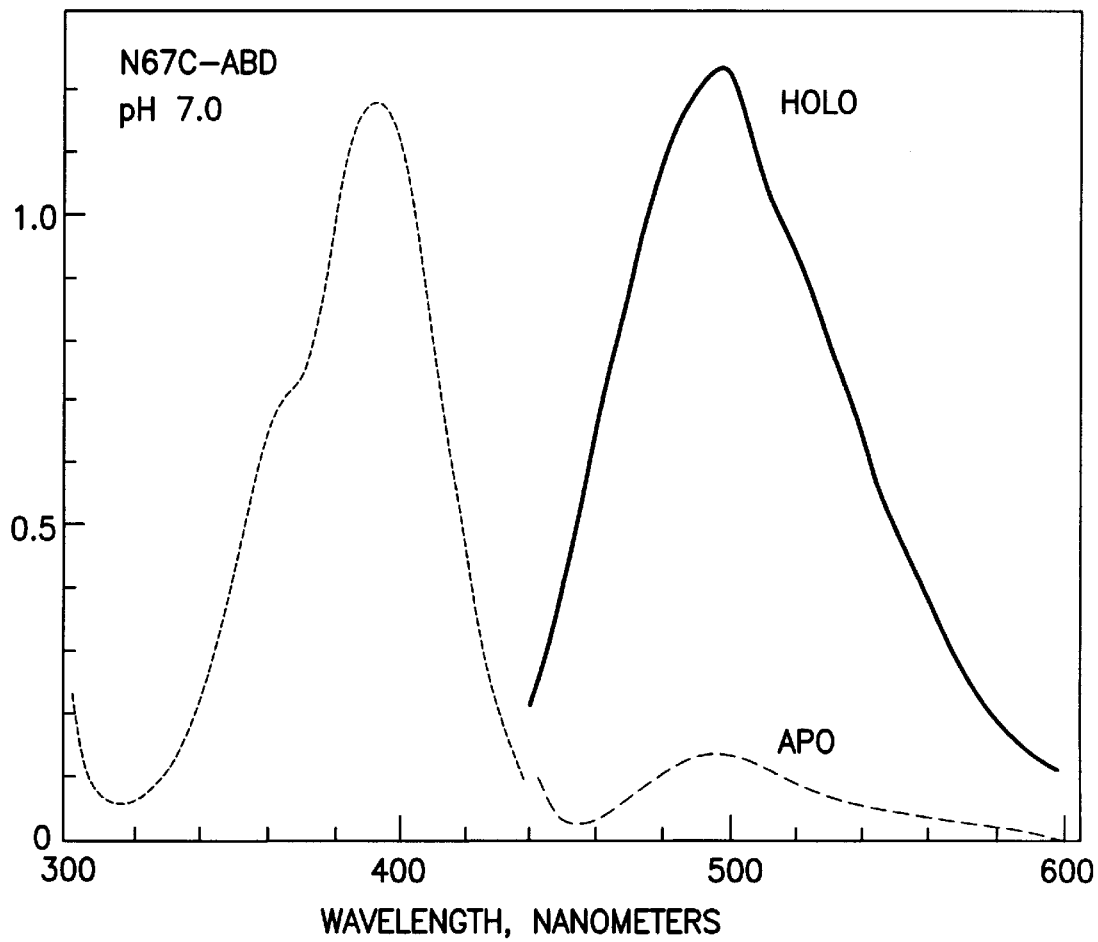
FIG. 6 shows fluorescence excitation (- - -) and emission spectra of ABD labelled N67C variant in the holo (___) and apo (_ _) forms.
Figure 7:
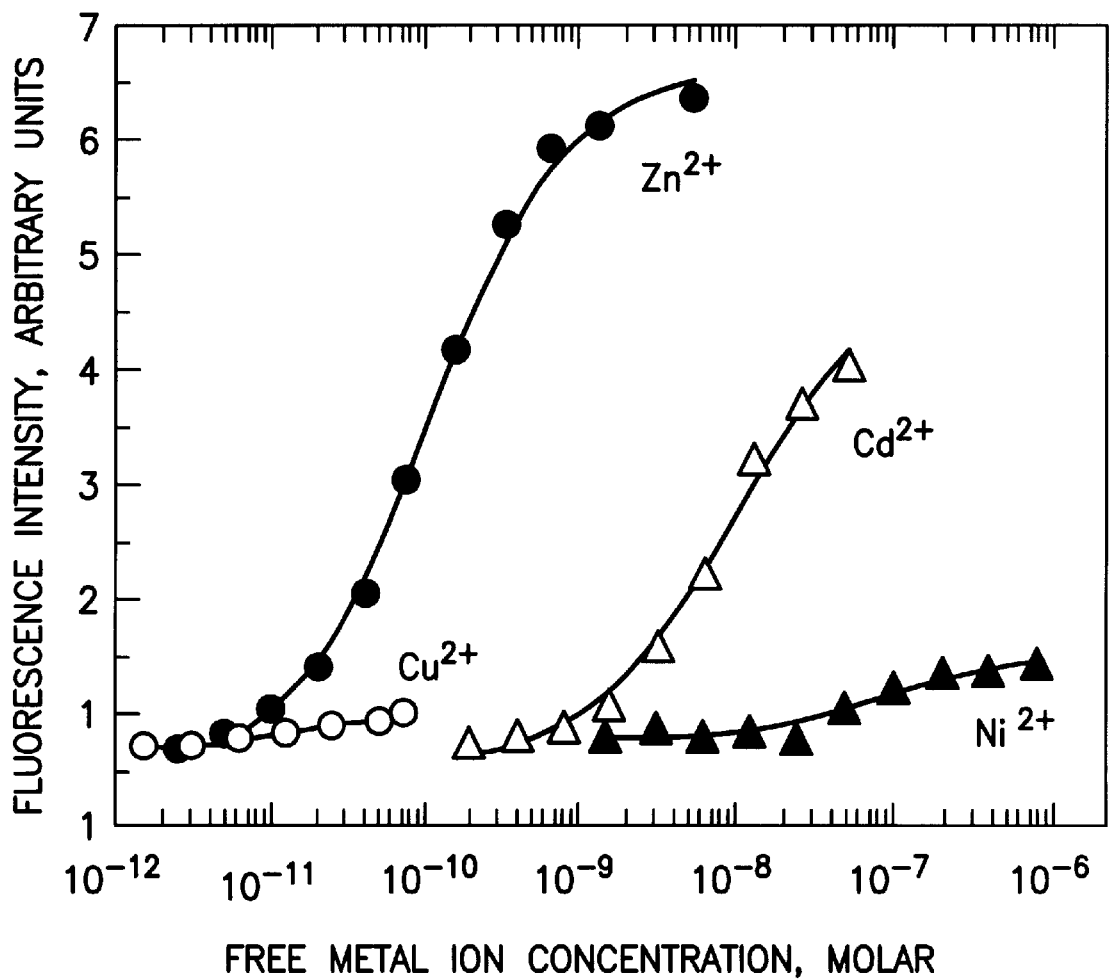
FIG. 7 shows fluorescence intensity (arbitrary units) as a function of metal ion concentration for apo-N67C-ABD in the presence of zinc [Zn(II)] (●), copper [Cu(II)] (○), cadmium [Cd(II)] (Δ), and nickel [Ni(II)] (▲).

Labeling of apo-N67C CA with ABD-F produced a yellow-orange conjugate ($\epsilon_{max}$=397 nm) which fluoresced maximally in the green (FIG. 6). Addition of Zn(II) ion to the fluorescent-labeled apoprotein caused a dramatic ten-fold increase in fluorescence intensity; addition of Cu(II), Cd(II), or Ni(II) caused less dramatic increases in intensity. Titrating the ABD-N67C with each of the metal ions in buffered solutions demonstrated a concentration dependence of the fluorescence intensity for each metal ion (FIG. 7). The data are well-fit in each case by single binding isotherms with $K_D$=17±4 pM (Cu(II)), 110±10 pM (Zn(II)), 9±2 nM (Cd(II)) and 80±30 nM (Ni(II)). The affinity of apoABD-N67C for cadmium and nickel ions is thus relatively close to that of the wild type apoenzyme (9 nM and 15 nM, respectively) (K. McCall and C. A. F., unpublished data). However, the affinity for Cu(II) and Zn(II) is decreased significantly compared to the wild type $K_D$'s of 0.1 pM and 1.0 pM, respectively. The decreased metal affinity taken together with the large dequenching effect of Zn(II) suggests that the ABD fluorophore must be near enough to interact with the metal site, which is unsurprising given that residue 67 is less than 10° from the metal. However, we note that the sulfonamide moiety of the ABD fluorophore conjugated to this residue is not properly positioned to bind as a sulfonamide anion as is typically the case with aryl sulfonamide inhibitors. This is further borne out by the lack of any excitation or emission shift (FIG. 6) upon binding of the Zn(II), as is seen with dansylamide, ABD-M or ABD-N (described in our previous patent applications mentioned above). The relatively close proximity of the ABD moiety to the active site suggests that it may have perturbed the binding of the various metals; thus there is no reason to believe the apparent affinities derivable from the intensities in FIG. 7 are inaccurate. Finally, we note that the low free metal ion concentrations and the modest fluorescence lifetime of the ABD label (see below) are inconsistent with the intensity changes being due to classical collisional quenching as described by Stern-Volmer theory.

Figure 8:
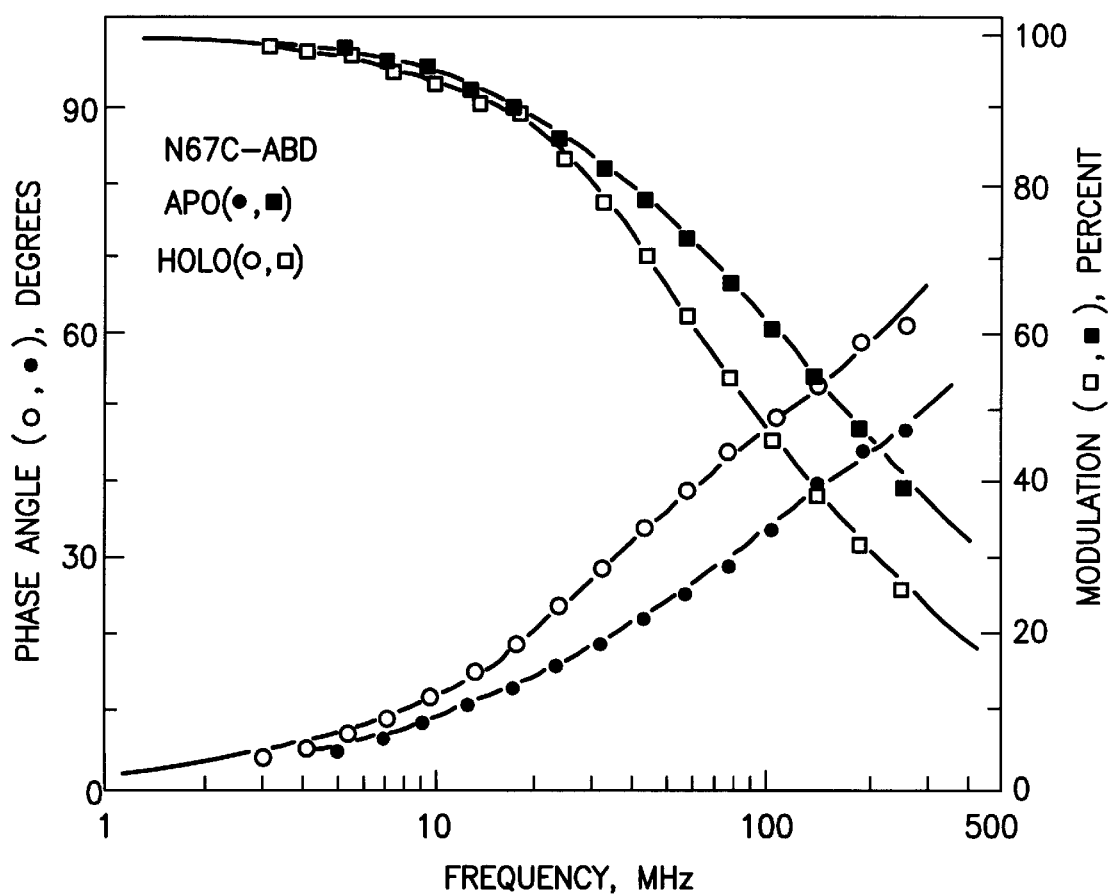
FIG. 8 shows frequency dependent phase shifts (●, ○) and modulations (■, □) for apo-N67C-ABD in the absence (●, ■) and presence (○, □) of a saturating concentration of zinc [Zn(II)].
Figure 9:
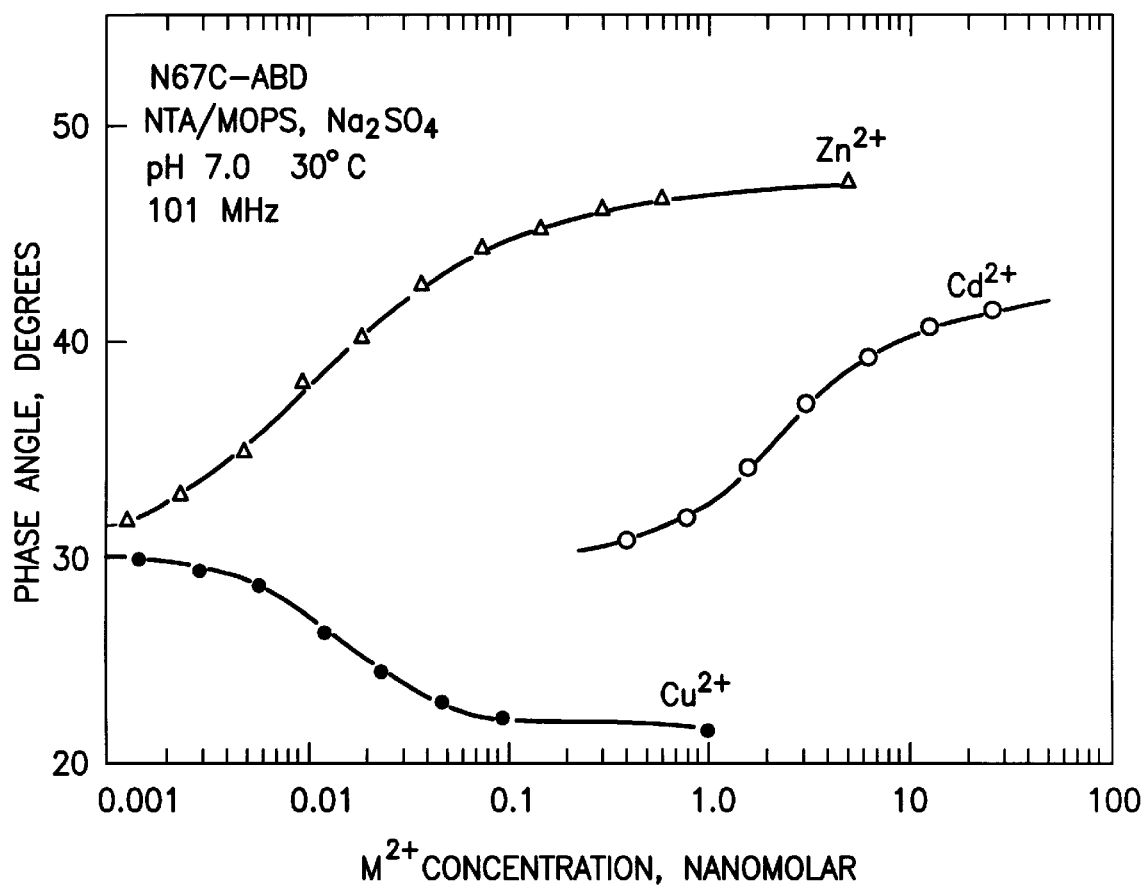
FIG. 9 shows phase angles at 101 MHz modulation frequency for apo-N67C-ABD measured as a function of copper [Cu(II)] (●), cadmium [Cd(II)] (○), or zinc [Zn(II)] (Δ) concentrations.
Figure 10:
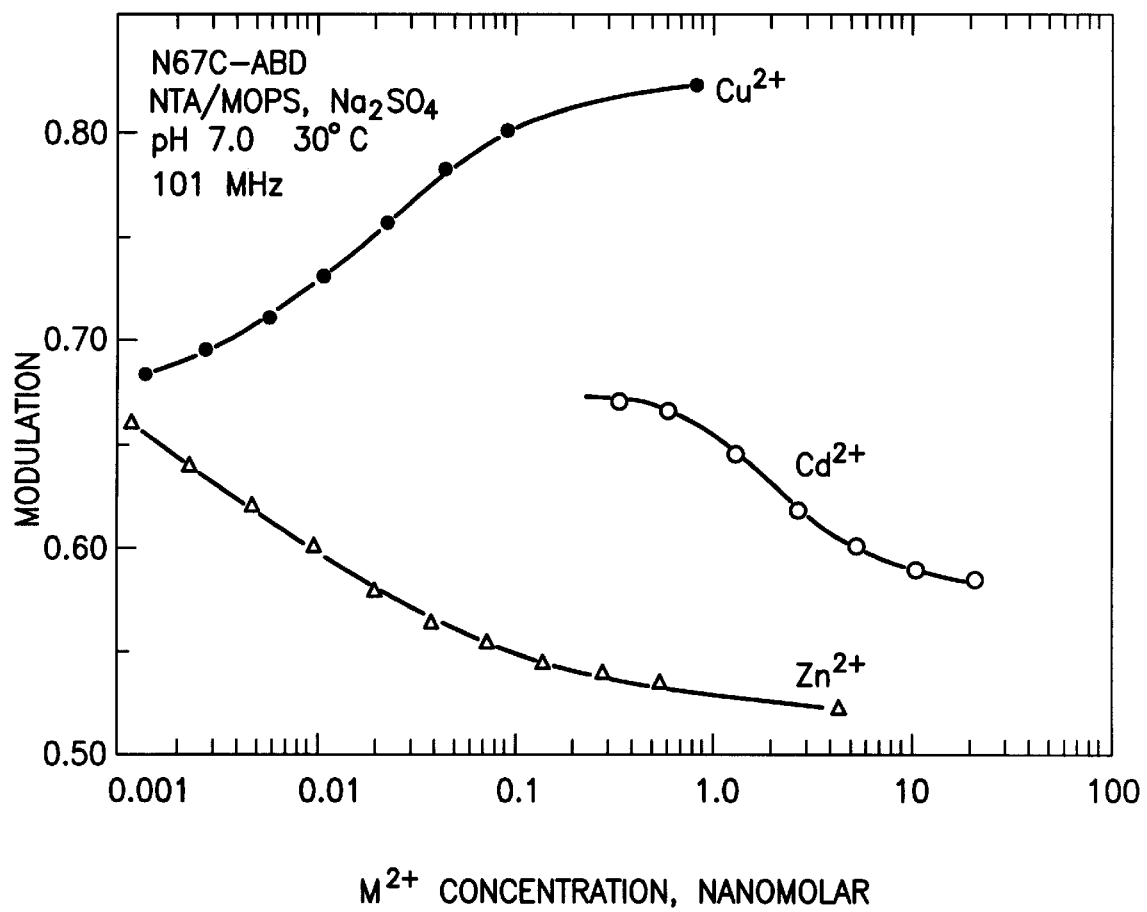
FIG. 10 shows modulation at 101 MHz modulation frequency for apo-N67C-ABD measured as a function of copper [Cu(II)] (●), cadmium [Cd(II)] (○), or zinc [Zn(II)] (Δ)concentrations.

The fluorescence lifetimes of N67C-ABD carbonic anhydrase in the apo-form and with metal ions bound were also measured using multifrequency phase fluorometry. In the absence of metal ions the apo-form exhibited a complex decay (FIG. 8) which could be fit ($x^2$=7.0) by three components: a 7.8 nsec component with fractional intensity of 27%, a 1.3 nsec component with 56%, and a 0.16 nsec component with 17%. Binding of Zn(II) to the apoprotein increased the average lifetime, but not as much as the intensity increased, suggesting that some static quenching occurs in the apo form. In particular, the frequency-dependent phase and modulation data were well fit by a three component decay ($x^2$=1.2) with the main components being 5.7 nsec (46%), 1.8 nsec (45%) and 0.36 nsec (9%). If the phase angle and modulation are measured at a suitable modulation frequency, significant changes may be observed as a function of analyte (metal ion) concentration if the lifetimes are different enough, as is evidently the case. Thus phase shifts and modulations were measured at 101 MHz for apoN67C-ABD as a function of free metal ion concentration for Zn(II), Cu(II) and Cd(II) FIGS. 9 and 10. The phase angle of the apo-N67C-ABD is 30 degrees; addition of Zn(II) increases the lifetime substantially, creating an increase in phase angle of sixteen degrees (FIG. 9). The modulation change is equally dramatic, resulting in a decline from 68% to 52% (FIG. 10). In view of the facts that the ordinary accuracy and precision of phase and modulation measurements are roughly a few parts per thousand, it is clear that the Zn(II) concentration can be determined with some precision by this method. In contrast, the binding of Cu(II) causes a decrease in lifetime which results in a decline in phase angle by eight degrees and an increase in modulation by 14%. This is at odds with the slight increase in intensity that accompanies the binding of copper ion, which we attribute to the sum of a decrease of a static quenching process (which increases the intensity without changing the lifetime) with a metal-dependent quenching process which decreases the lifetime and intensity. The behavior of Cd(II) in this respect mirrors that of Zn(II), but at lower concentrations. The apparent affinities taken from the phase angle and modulation data are approximately 10 pM for Cu(II), 20 pM for Zn(II), and 3 nM for Cd(II). Again, these figures are similar to the wild type binding affinities; we note that the nonlinear way in which the phase angles and modulations of the bound and free forms contribute to the observed values makes it difficult to accurately determine the $K_D$ solely from data of this kind without separate calibration. Nevertheless, it is apparent that apo-N67C-ABD responds well to the binding of Cd(II), Cu(II), and Zn(II).

Figure 11:
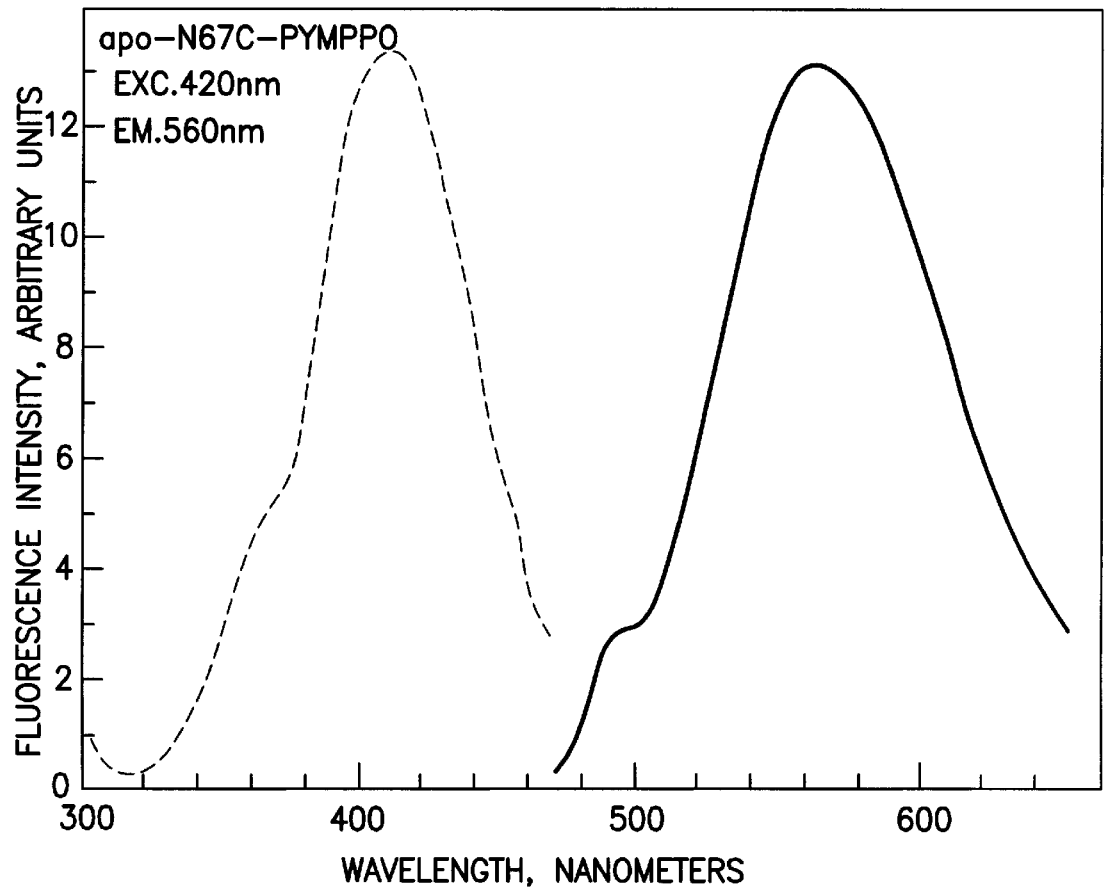
FIG. 11 shows fluorescence excitation (- - -, emission at 560 nm) and emission (___, excitation at 420 nm) spectra of apo-N67C-PyMPO.
Figure 12:
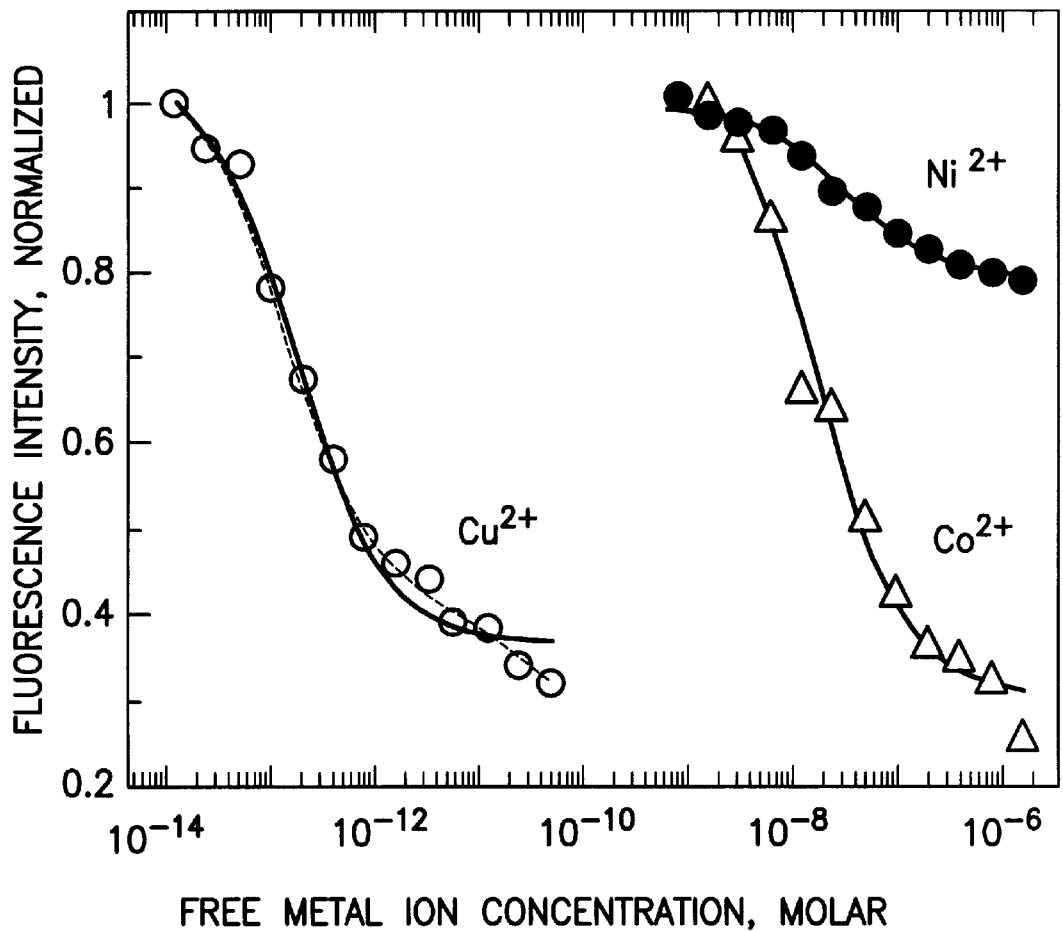
FIG. 12 shows normalized fluorescence intensities of apo-N67C-PyMPO (excitation at 410 nm, emission at 550 nm) as a function of copper [Cu(II)] (□), cobalt [Co(II)] (Δ), or nickel [Ni(II)] (●) concentrations.

The significantly higher extinction coefficient of PyMPO makes it a brighter fluorophore than ABD. When conjugated to N67C-CA, it exhibits a large Stokes' shift with broad emission at 550 nm (FIG. 11), whereas the emission is somewhat to the red when conjugated at F131C-CA (maximum at 565 nm)(results not shown); absorbance and excitation maxima for both labeled variants are at 412 nm, and they can be readily excited by the 442 nm line of the HeCd laser FIG. 11. Addition of saturating concentrations of Zn(II) or Cd(II) have a negligible effect on the fluorescence intensity of PyMPO-labeled apo-N67C-CA, but addition of Ni(II), Co(II) or Cu(II) induces decreases in intensity of approximately 25%, 75% and 70%, respectively. Measurement of intensities of PyMPO-labeled apoN67C-CA as a function of free Ni(II), Co(II), and Cu(II) yielded the expected binding isotherms for cobalt and nickel (FIG. 12), but not for copper ion (see below). The fitted values for nickel and cobalt are 30±3 nM and 16±3 nM, which are respectively comparable to and eight-fold higher than the wild type affinities. Fit to a single isotherm, the Cu(II) data yielded 0.17±0.02 pM, which is also close to the wild type value. However, while the cobalt and nickel isotherms showed the usual range of ten to ninety percent intensity change over approximately 1.9 log units in metal ion concentration, the copper isotherm extended over a broader concentration range. The data in FIG. 12 are perhaps best explained by binding of a second mole of copper ion in addition to the active site Cu(II); the apparent affinities of these two sites are about 0.13 pM and 30 pM, respectively. We have observed binding of Co(II) apparently to an additional site on other variants of CA, and binding of transition metals to polypeptides is well known. Furthermore, Cu(II) has been observed by x-ray crystallography to bind to a second site on wild type human CA II by Hakansson and his colleagues (Acta Crystallogr, D50:93–100, 1994). They found that the second Cu(II) was bound by two histidines (4 and 64) near the active site, which would account for the apparent quenching of the PyMPO by the second Cu(II), and its apparently weaker affinity.

Figure 13:
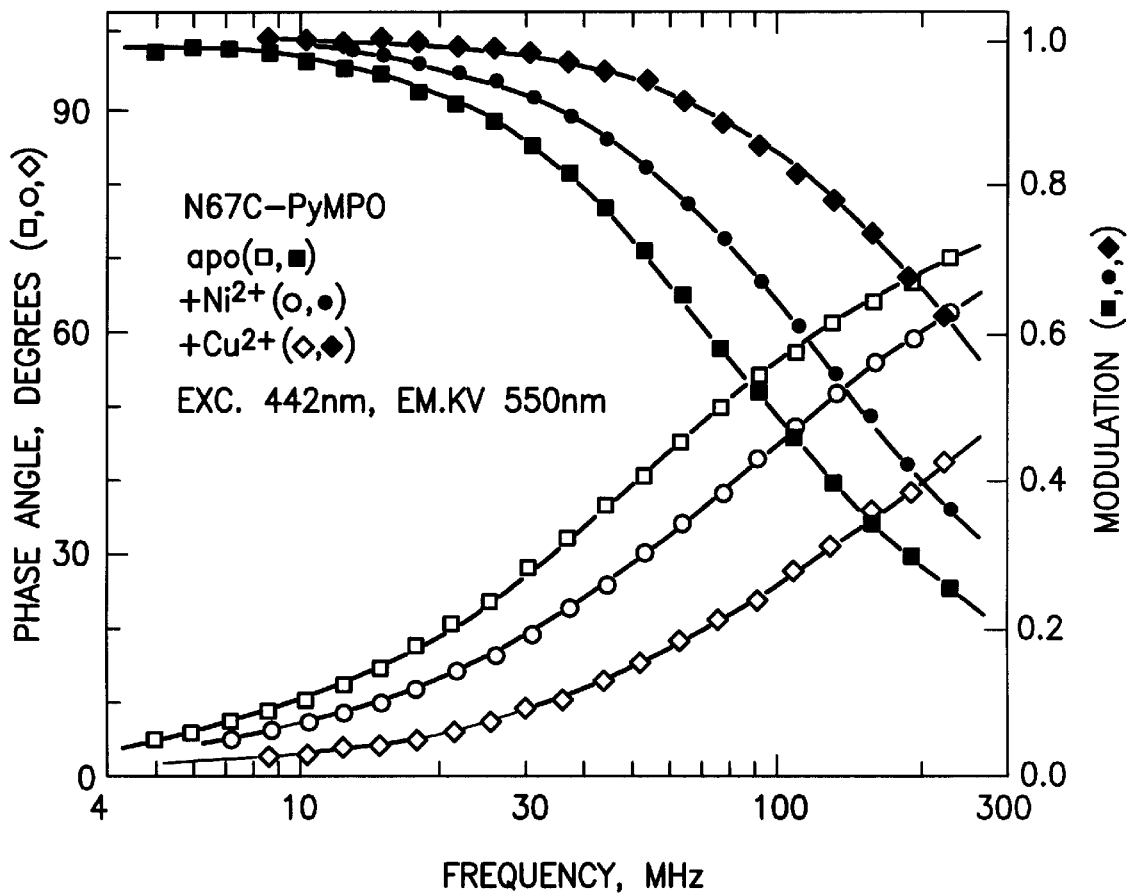
FIG. 13 shows frequency dependent phase shifts (□, ◇, ○) and modulations (■, ●, ♦) or apo-N67C-ABD in the absence (□, ■) and presence of a saturating concentration of copper [Cu(II)] (◇, ♦) and nickel [Ni(II)] (○, ●).
Figure 14:
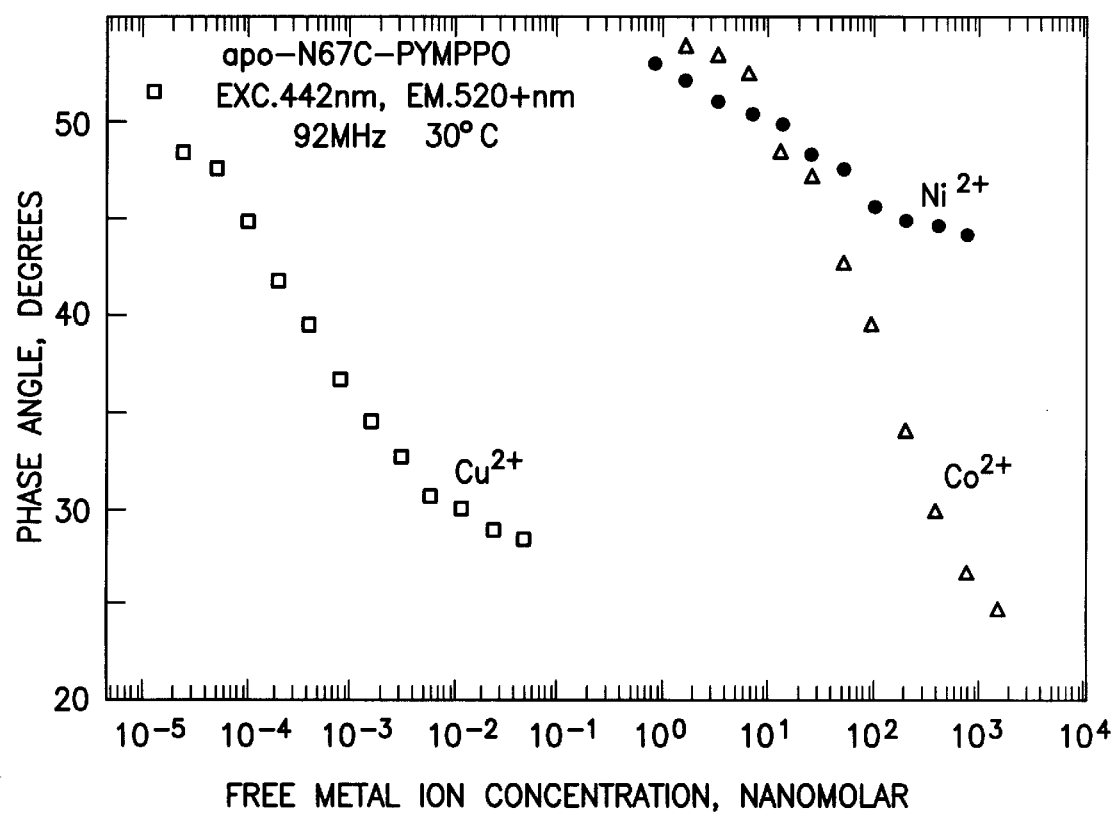
FIG. 14 shows phase angles at 92 MHZ for apo-N67C-PyMPO as function of copper [Cu(II)] (□), cobalt [Co(II)] (Δ), or nickel [Ni(II)] (●) concentrations.
Figure 15:
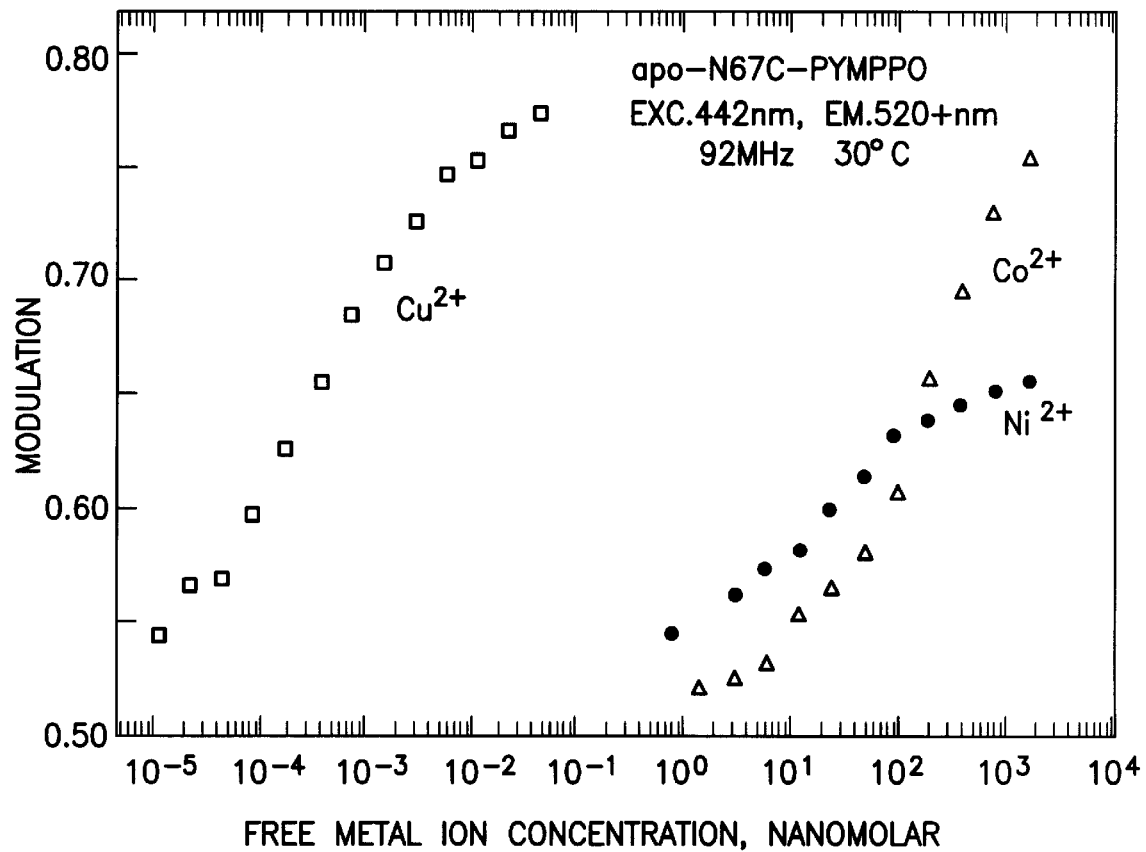
FIG. 15 shows modulation at 92 MHZ for apo-N67C-PyMPO as a function of copper [Cu(II)] (□), cobalt [Co(II)] (Δ), or nickel [Ni(II)] (●) concentrations.

We measured the fluorescence decays of the PyMPO-labeled apo-N67C-CA variant in the absence of metal and in the presence of saturating concentrations of Ni(II), Co(II), and Cu(II). The decays were complex FIG. 13 and best fit by three components Table 2, below. As is apparent from FIG. 13 and Table 2, the fluorescence decays in the presence of Ni(II), Co(II) and Cu(II) are markedly different from that of the apoprotein, as judged by the frequency-dependent phase shifts and demodulations. The large apparent differences in phase angle and modulation in the range of 90 MHz suggests that PyMPO-labeled CA variants could be successfully used for lifetime-based sensing of Cu(II), Co(II), and Ni(II). In particular, we note that the phase angle differences at 90.9 MHz between PyMPO-labeled N67C-CA in the apo form and with Cu(II), Co(II), and Ni(II) are 30.3, 19.4, and 11.6 degrees, respectively, with commensurate differences in modulation FIGS. 13 and 14. These differences are more than adequate for lifetime-based sensing of these metal ions. The very short average lifetimes compared to the approximately 15 nsec rotational correlation time of the protein result in any differences in anisotropy between apo and metal-bound forms being negligible (results not shown), and thus these labeled forms of CA are not very useful for anisotropy-based sensing.

TABLE 2

Best 3-component fits to apo-N67C-PyMPO phase and modulation data

| Metal[a] | $\tau_1$ | $f_1$ | $\tau_2$ | $f_2$ | $\tau_3$ | $f_3$ | $x^2$ | $<\tau>$ |
|---|---|---|---|---|---|---|---|---|
| None | 5.00 | .155 | 2.69 | .780 | 0.63 | .065 | 1.2 | 2.92 |
| $Cu^{2+}$ | 1.56 | .279 | 0.72 | .613 | 0.05 | .108 | 1.9 | 0.88 |
| $Co^{2+}$ | 2.63 | .392 | 0.85 | .435 | 0.10 | .172 | 0.6 | 1.42 |
| $Ni^{2+}$ | 3.56 | .207 | 1.595 | .753 | 0.20 | .040 | 1.3 | 1.95 |

[a]Abbreviations include: "metal" refers to the presence of a saturating concentration of the indicated metal ion; $\tau_i$ and $f_i$ refer to the lifetime in nanoseconds and fractional intensity of component i; $0^2$ is the sum of the squares of the differences between measured and fitted values of phase and modulation, normalized to the average standard deviations; and $<\tau>$ is the average lifetime in nanoseconds. Precisions of the derived lifetimes and fractional intensities were typically ± 20 picoseconds and ± .003, respectively.

ABD-M

The embodiment described herein utilizes scheme I described above. Although the specific results discussed below are directed to anisotropy sensing, it is important to note that ABD-M can be utilized in lifetime, intensity and wavelength shift measurement systems. These results are also discussed in our publication in the Proceedings of the SPIE Conference on Advances in Optical Biophysics (volume 3256, March 1998) which is specifically incorporated by reference in its entirety.

We describe a biosensor employing wild type human apocarbonic anhydrase II and a fluorescent ligand, ABD-M. We can determine free metal ions, such as zinc, in solution at concentrations in the picomolar range with good accuracy by fluorescence anisotropy. In particular, by judicious choice of excitation and emission wavelengths, the concentration range over which Zn(II) may be determined accurately can be increased by approximately two orders of magnitude. As ABD-M also exhibits significant changes in excitation and emission spectra as well as lifetime upon binding to the active site Zn(II) in holocarbonic anhydrase, it should also be useful for wavelength ratiometric and lifetime-based determinations.

Figure 16:
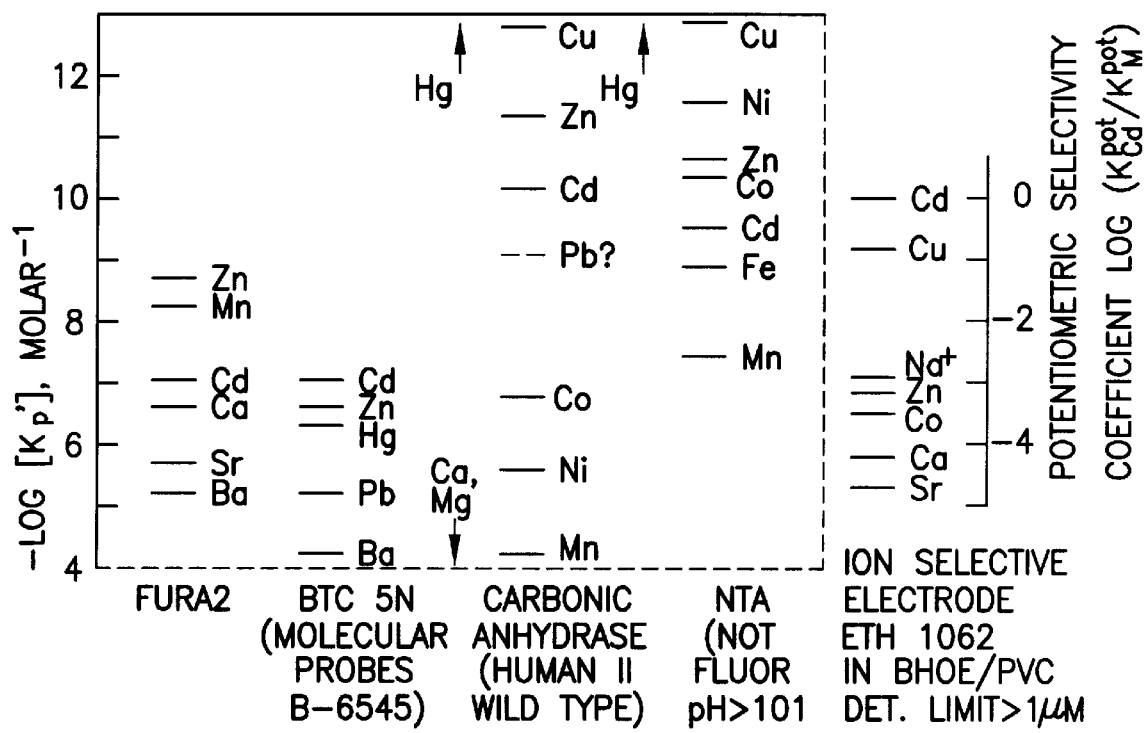
FIG. 16 shows relative transition metal ion affinities (note log scale) of fluorescent indicators Fura-2 and BTD-5N, apocarbonic anhydrase II, nitrilotracetic acid, and an ion-selective electrode. The selectivity scale for the ISE is given in different units according to Simon. The actual detection limit is approximately 1 micromolar.
Figure 17:
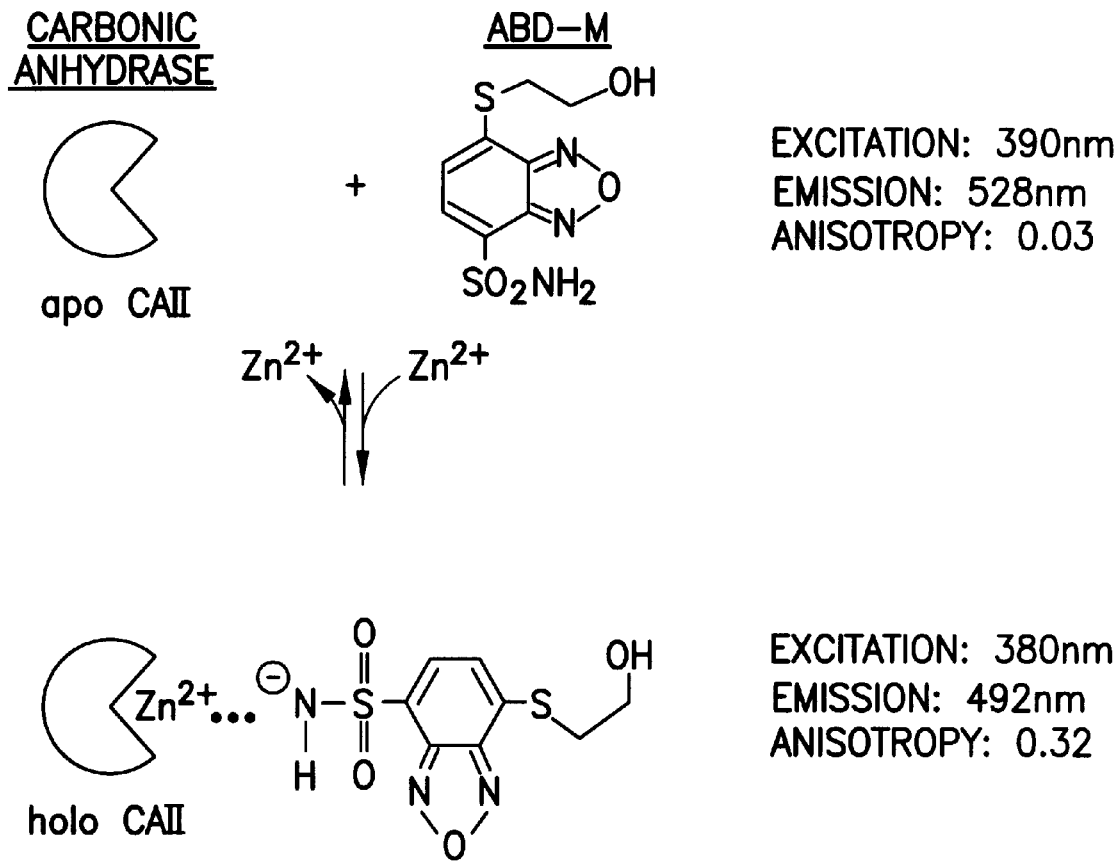
FIG. 17 shows the principles of fluorescence anisotropy based determination of zinc ion using ABD-M.

Our approach for determining metal ions by fluorescence anisotropy is diagrammed in FIG. 16. The chemical synthesis and structure of ABD-M is shown in FIG. 17. ABD-M was synthesized by coupling ABD-F (7-fluoro-benz-2-oxa-1,3-diazole-4-sulfonamide; Molecular Probes Cat. No.F-6053) with excess beta-mercaptoethanol in dimethylformamide overnight at room temperature (FIG. 17). Coupling resulted in the appearance of a pale yellow color, greenish fluorescence under UV illumination, and appearance of a greenish fluorescent spot on silica gel thin layer chromatography ($r_f$=0.68; 20% methanol in methylene chloride). The solvent and thiol were removed under vacuum; the product ABD-M had an approximate extinction coefficient of 8000

$M^{-1}$ $cm^{-1}$ at 376 nm in methanol. Recombinant human carbonic anhydrase II was expressed, isolated, and purified; and its Zn(II) removed by treatment with dipicolinate all as previously described. In view of the well-known difficulty of reproducibly preparing solutions with low concentrations of free zinc ion, we prepared a series of metal ion buffers using nitrilotriacetic acid (NTA) and MOPS. NTA has relatively high affinity for Zn(II) near neutral pH and consequently a very high proportion of added Zn(II) will be bound by the NTA; variations in the free zinc concentration due to binding by other ligands or contamination from other sources are counteracted by the release or uptake of Zn(II) by the NTA, thereby buffering the metal ion concentration. The concentration of Zn(II) unbound at a particular pH is readily calculable from the known stability constants of the NTA and the pKa's of NTA's ionizable groups (19). For instance, at pH 7.0 a millimolar NTA solution that is 4.007 uM in total Zn(II) concentration will exhibit a free Zn(II) concentration of 2.44 pM, or $5\times10^{-5}$% of the total. MOPS (10 mM) was chosen to buffer the pH as its affinity for Zn(II) is very low. Other reagents, buffers and solvents were of the highest purity available; buffers were passed over Chelex-100 columns (Bio-Rad), handled with metal-free pipet tips (Bio-Rad), and never exposed to glass surfaces thereafter, all to minimize metal contamination. Metal ion buffers were formulated for a desired pH and free metal ion concentration using a computer spreadsheet program developed at Duke University by Keith McCall and C. A. Fierke. Samples containing Zn, apoenzyme, and ABD-M were incubated for four hours or more at 30 C. to assure that the Zn(II) binding to the apoenzyme had achieved equilibrium, based on the known kinetics of Zn(II) ion binding by the wild type enzyme.

Fluorescence spectra, intensities and anisotropies were measured on a Spectronics AB-2 fluorimeter using film polarizers and 4 nm bandpasses. Frequency-dependent phase shifts and demodulations were measured on an ISS K2 phase fluorometer using the UV lines of a Spectra-Physics 2065 argon ion laser for excitation, dimethylPOPOP in ethanol as a reference compound as previously described, and bandpass filters as indicated in the figure legends. The phase and modulation data were fit to multicomponent decay laws using proprietary software from ISS (Champaign, Ill.).

Figure 18:
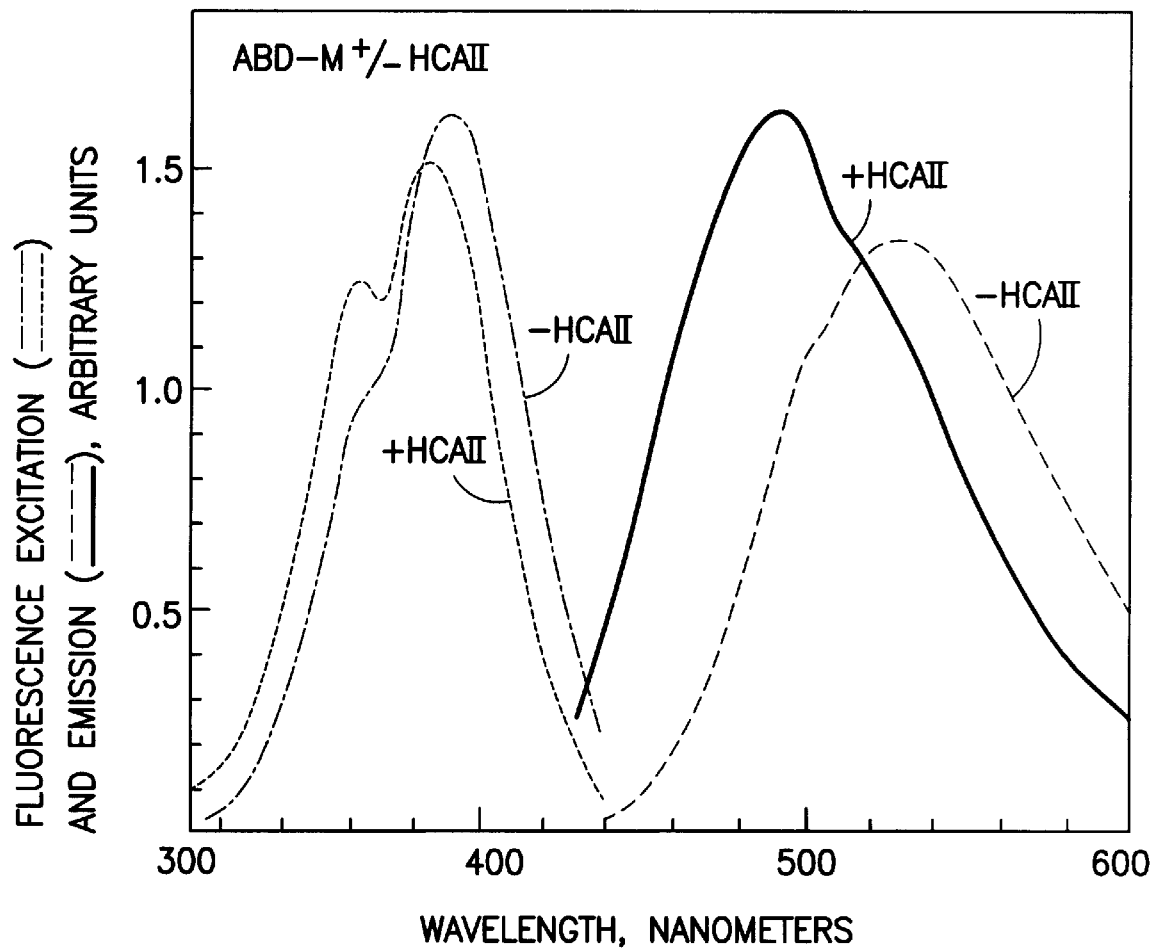
FIG. 18 shows emission and excitation spectra of ABD-M. Uncorrected excitation spectra are depicted for ABD-M in the absence (_._, emission at 524 nanometers) and presence ( . . . . . , emission at 496 nanometers) of holoenzyme. Uncorrected emission spectra (excitation at 368 nanometers) are depicted for ABD-M free in solution (_ _, emission at 524 nanometers) and bound to the holoenzyme (___).

In pH 7.0 10 mM MOPS, 0.5 mM nitrilotriacetic acid ABD-M absorbs maximally at 390 nanometers and emits maximally at 520 nanometers FIG. 18. Upon addition of holo-CA in micromolar amounts, there is a shift in the absorbance maximum to 380 nanometers and emission to 495 nanometers. The blue shifts in excitation and emission are consistent with ABD-M's binding in an hydrophobic site and/or becoming deprotonated to form the anion. The affinity of ABD-M for holo-CA could be determined by changes in fluorescence intensity or anisotropy in the usual manner; at pH 7.0 in MOPS buffer we measured an affinity of 0.3±0.05 uM (results not shown). This affinity is somewhat greater than that of dansylamide (0.8 um). ABD-M does not appear to bind significantly to the apoprotein or to Zn(II), Cu(II), Cd(II), or Ni(II) free in solution as judged by lack of change in the fluorescence emission. The changes in absorbance, excitation, and emission spectra, taken together with the dramatically reduced affinity for the apoprotein, are readily explained by binding of ABD-M to the holoprotein as a sulfonamide anion, as has been seen for many inhibitors of carbonic anhydrases, including dansylamide and azosulfamide. Thus it seems likely that ABD-M will also serve as an inhibitor of CA's enzyme activity.

Figure 19:
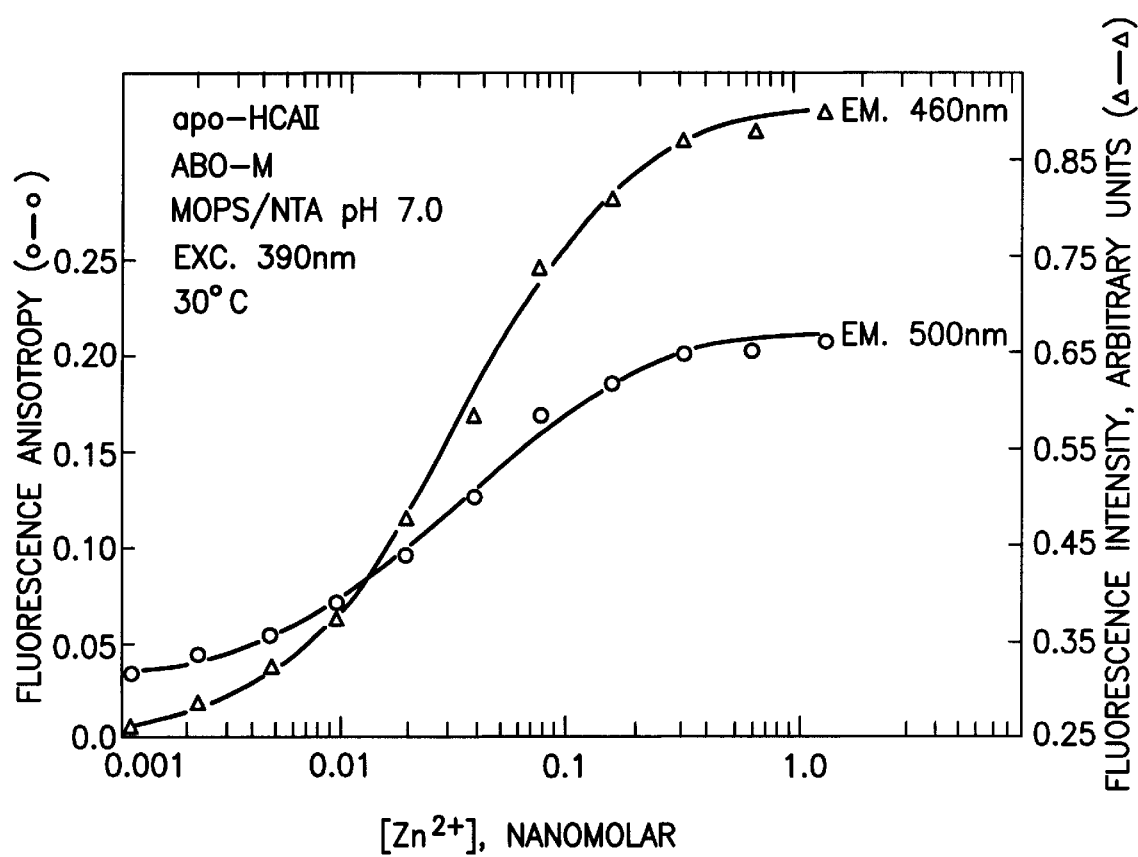
FIG. 19 shows fluorescence intensity (○) and anisotropy (▲) of ABD-M labelled apocarbonic anhydrase II as a function of free zinc [Zn(II)] concentration in pH 7.0 MOPS/NTA buffer.

The modest shifts in fluorescence emission upon binding to holo-CA exhibited by ABD-M may be used in a wavelength ratiometric fashion to quantitate the fraction of the enzyme with Zn(II) bound in the active site as we have previously described for dansylamide, but the effect is less dramatic for ABD-M. ABD-M exhibits an apparent 50% increase in fluorescence intensity at 500 nm (excitation=390 nm) upon binding to holoprotein; this effect may be exaggerated to a three-fold change by shifting the wavelength of emission observed to 460 nanometers (FIG. 19). The fluorescence lifetime of ABD-M determined by phase fluorometry changes modestly and in a complex manner upon binding to the enzyme (data not shown), suggesting that this system would respond modestly for lifetime-based sensing. In particular, free ABD-M in buffer exhibits a predominant component of 0.8 nsec with evidence of a significant excited state reaction ($x^2=1.2$), whereas when bound to the holoprotein ABD-M exhibits a 0.9 nsec component (55% fractional intensity) and a 2.3 nsec component (45%), with no apparent excited state reaction ($x^2=0.7$). Since the modulations differ by less than 0.17 at any frequency and the phase angles differ by less than seven degrees at any frequency, the system responds modestly for lifetime-based sensing.

The most interesting property of ABD-M from the standpoint of Zn(II) determination is the change in fluorescence anisotropy observed upon binding of ABD-M to the holoprotein. ABD-M exhibits a low anisotropy (0.019) when free in aqueous solution, but quite high anisotropy (up to 0.32) when bound to the holoprotein. The measured anisotropy thus reflects the fraction of protein with metal bound and therefore the metal ion concentration by the Law of Mass Action. This is a significantly greater response than we had observed with another inhibitor. Using metal ion buffers to accurately maintain low concentrations of free Zn(II), we were able to measure the resulting anisotropy for fractionally bound enzyme (FIG. 19). We note that at these buffer (5 mM NTA) and enzyme (2–3 micromolar) concentrations, the enzyme does not perturb the free metal ion concentrations. To conveniently formulate either higher or lower free concentrations of Zn(II), other buffers such as EDTA, citrate, or Bicine might be used.

Figure 20:
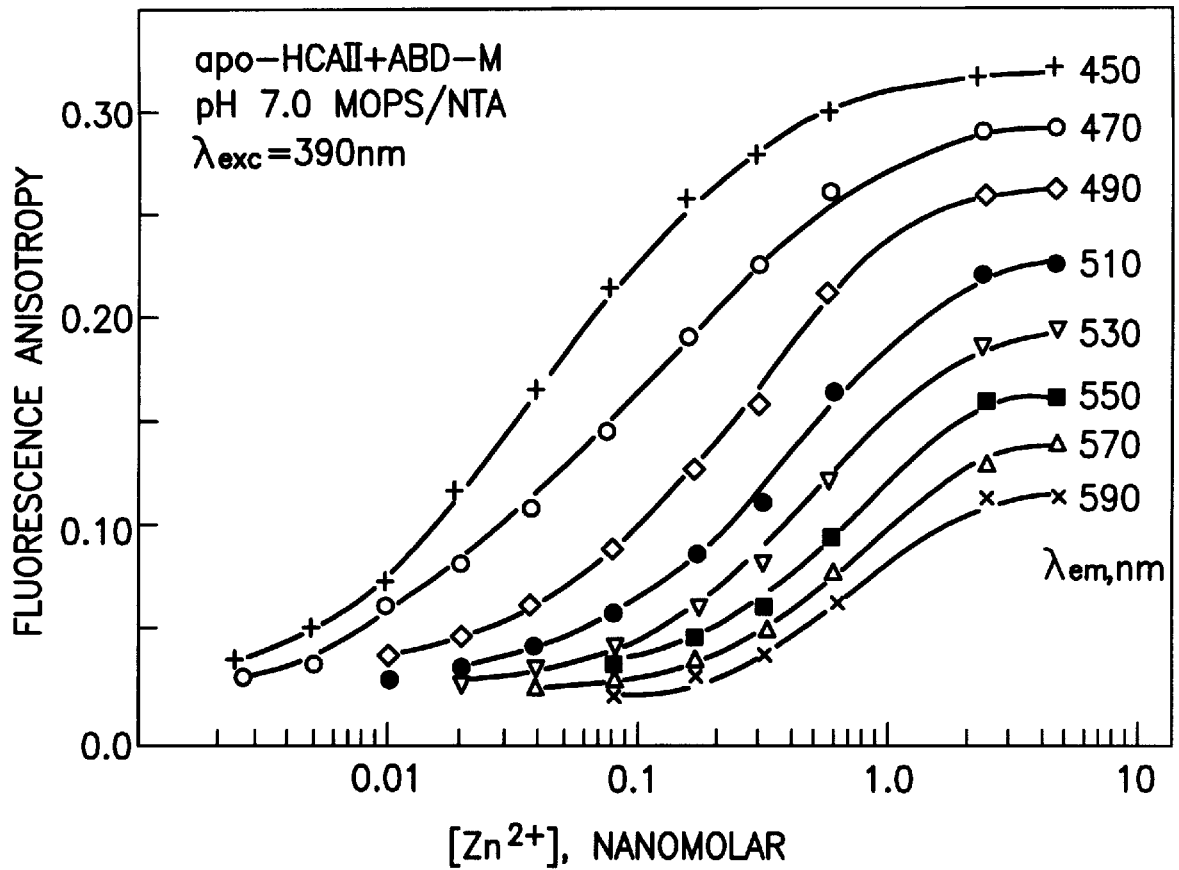
FIG. 20 shows fluorescence anisotropy of ABD-M plus apoCA as function of free zinc [Zn(II)] concentration measured at emission wavelengths of 450 nm (+), 470 nm (○), 490 nm (◇), 510 nm (●), 530 nm (▽), 550 nm (■), 570 nm (Δ) and 590 nm (x).

The fact that the excitation and emission both shift to the blue dictates that we can preferentially observe fluorescence from the bound or free forms of ABD-M by judicious choice of excitation and emission wavelengths. In the same fashion as it does for lifetime-based determinations, this phenomenon permits us to expand the dynamic range of Zn(II) determination by fluorescence anisotropy. For an observable exhibiting a linear response with fractional occupancy of the binding site, the ordinary span between 10% and 90% bound is an 80-fold span in ligand concentration. In general it is difficult to accurately measure the fractional saturation below 10% or above 90%, which roughly establishes the dynamic range. In this case, circumstances permit us to more accurately measure at the extremes of the binding curve. For instance, on the blue side of the emission band, one can preferentially observe the bound form of ABD-M, even in a large excess of the free form. This may be observed in FIG. 20, which depicts the anisotropy measured at several different wavelengths as a function of Zn(II) concentration. At the blue side of the emission, where emission from the bound form predominates, the apparent $K_D$ is approximately 50 pM; whereas on the red side of the emission where the free form predominates it is approximately 1000 pM. Of course, the binding constant does not change with wavelength. The virtue of this technique is that Zn(II) may be accurately quantitated over a relatively broad range by simply changing the emission (and/or excitation) wavelength employed. Ordinarily, it is difficult to accurately quantitate fractions bound of less than 10% or greater than 90%; by use of this approach, very low or high fractional occupancies may be quantitated. At the current state of the art, this is not an attribute of ratiometric determinations.

The large dynamic range demonstrated with the technique offers some advantages. First, because switching the sensitivity range is as easy as changing a filter, serial dilutions are less necessary to achieve an accurate measurement. For unknown samples, this simplifies rangefinding and eliminates errors and artifacts introduced by dilution. Minimizing the need for resampling and/or dilution of samples is particularly important in field work where these may be costly, difficult, or impossible. Second, calibration is improved because anisotropy measurements can be made at several different emission bands and compared with the calibration model. Finally, development of additional aryl sulfonamides may permit broadening of the dynamic range.

Similarly, the high sensitivity of the technique offers advantages beyond low detection limits. In particular, when Zn(II) is present at higher levels, the deleterious effects of potential interferents such as fluorescent impurities, dissolved organic carbon, and scatterers may be minimized by diluting the sample. Zn(II) is an ion of emerging importance in the understanding of various disease states. The technique determines so-called "free" Zn(II) in aqueous solution rather than total Zn(II), which includes that held by various ligands likely to be present in natural waters and serum. Consequently, free levels of Zn(II) (and most other metal ions) in natural waters are generally believed to be orders of magnitude lower than total Zn(II). This is of interest because the chelation state of Zn(II) is likely to have an impact on its bioavailability, and therefore its effective levels as a nutrient in the ocean.

Dapoxyl Sulfonamide and BTCS

The embodiment described herein utilizes scheme 1 as described above. Although the specific results discussed below are directed to specific sensing mechanisms, it is important to note that Dapoxyl sulfonamide can be utilized in anisotropy, lifetime, intensity, and wavelength shift based sensing methods. BTCS finds utility in anisotropy and lifetime based systems.

Here, we describe the synthesis and properties of two new probes, Dapoxyl™ sulfonamide and BTCS, and their use in zinc biosensing. Dapoxyl sulfonamide exhibits a dramatic increase and blue shift in its emission upon binding to holo-carbonic anhydrase II, as well as a twenty-fold increase in lifetime: it is thus well suited for quantitating free Zn(II) down to picomolar ranges. The anisotropy of BTCS increases five-fold upon binding to the holoprotein, making this probe well suited for anisotrpy-based determination of zinc. The particular fluorescent aryl sulfonamides have enhanced absorbance and shorter lifetimes as compared to other probes described in the art, particularly with a view to their use for imaging zinc fluxes in cell and tissue specimens.

Figure 21:
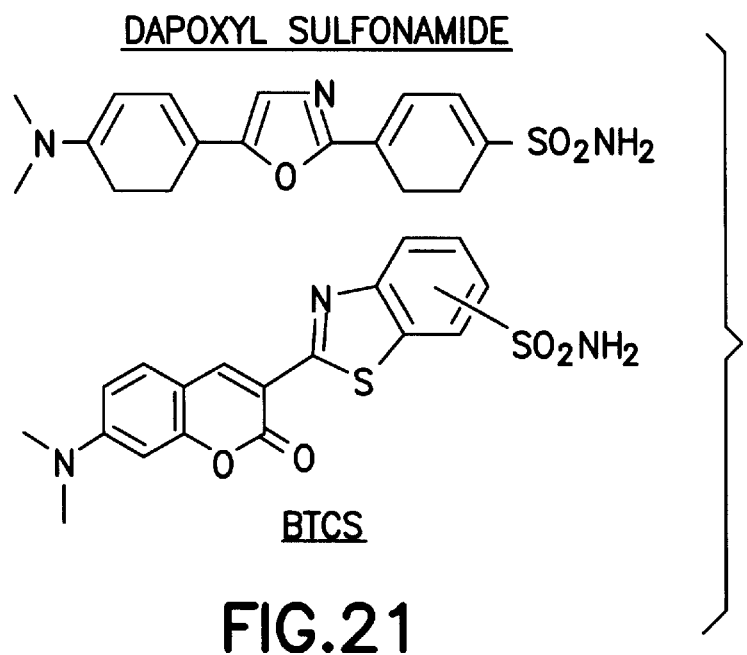
FIG. 21 shows the chemical structure of benzothioazolyl coumarin sulfonamide (BTCS) and dapoxyl sulfonamide.

Dapoxyl™ sulfonyl chloride is a product of Molecular Probes, Eugene, Oreg. (cat no. D-10160) and was used without further purification. Dapoxyl sulfonamide FIG. 21 was synthesized from the sulfonyl chloride and a ten-fold molar excess of aqueous ammonium hydroxide in DMF for one hour. The product precipitated from the neutralized aqueous phase and was collected by centrifugation. Absorbance ($\epsilon_{365}$=22,000 $M^{-1}$ $cm^{-1}$), excitation, and emission spectra FIG. 22 were similar to those published on Molecular Probes' website (<http://www.probes.com>) for the ethylamine adduct. BTCS (FIG. 21, 3-(2-benzothiazoyl)-7 -diethylaminocoumarin sulfonamide) was synthesized similarly from the analogous sulfonyl chloride (Lambda Fluorescence, Pleasant Gap, Pa., Catalog no. D-015). The sulfonyl chloride has recently been unavailable in the U.S.; it may be possible to obtain it from the parent firm, Lambda Probes and Diagnostics, Graz, Austria. The reaction product was further purified by reverse-phase HPLC on a $C_4$-silica gel column eluted with 10 mM ammonium acetate and a gradient of 0–90% acetonitrile. The excitation and emission spectra of BTCS ($\epsilon_{466}$=36,000 $M^{-1}$ $cm^{-1}$) in the presence and absence of holo-CA are depicted in FIG. 23. Both Dapoxyl sulfonamide and BTCS are only sparingly soluble in aqueous solutions near neutrality, and typically they were introduced to aqueous samples in small volumes of DMF.

The recombinant human carbonic anhydrase II was obtained by the means previously discussed herein. Fluorescence spectra and anisotropies were determined on a Spectronics AB-2 spectrophotofluorometer; the former are uncorrected. Fluorescence lifetimes were determined on an ISS K2 multifrequency phase fluorometer using the 442 nm line (30 mW) of a Kimmon HeCd laser (for BTCS) or the ultraviolet lines (100 mW) of a Spectra-Physics model 2065-7S argon ion laser (for dapoxyl sulfonamide) essentially as previously described. Two-photon excitation was obtained from a Spectra-Physics Tsunami modelocked titanium:sapphire laser which produced 880 mW average power at 800 nm with pulses emitted at 80 MHZ with duration of 1.5 psec. Other reagents were reagent grade or better and used without further purification.

Figure 22:
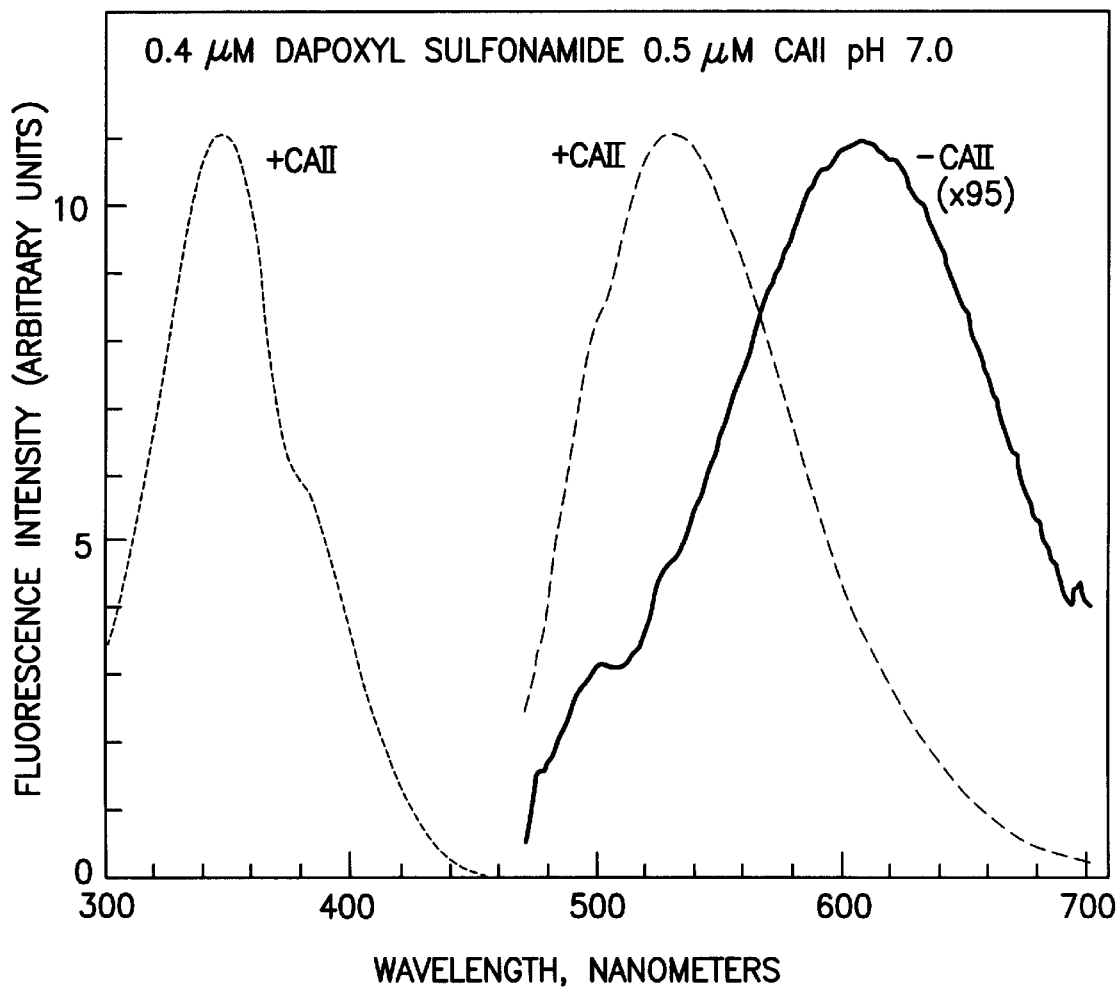
FIG. 22 shows normalized emission and excitation spectra of dapoxyl sulfonamide in the absence (___) and presence (- - - - -) of holocarbonic anhydrase II.
Figure 23:
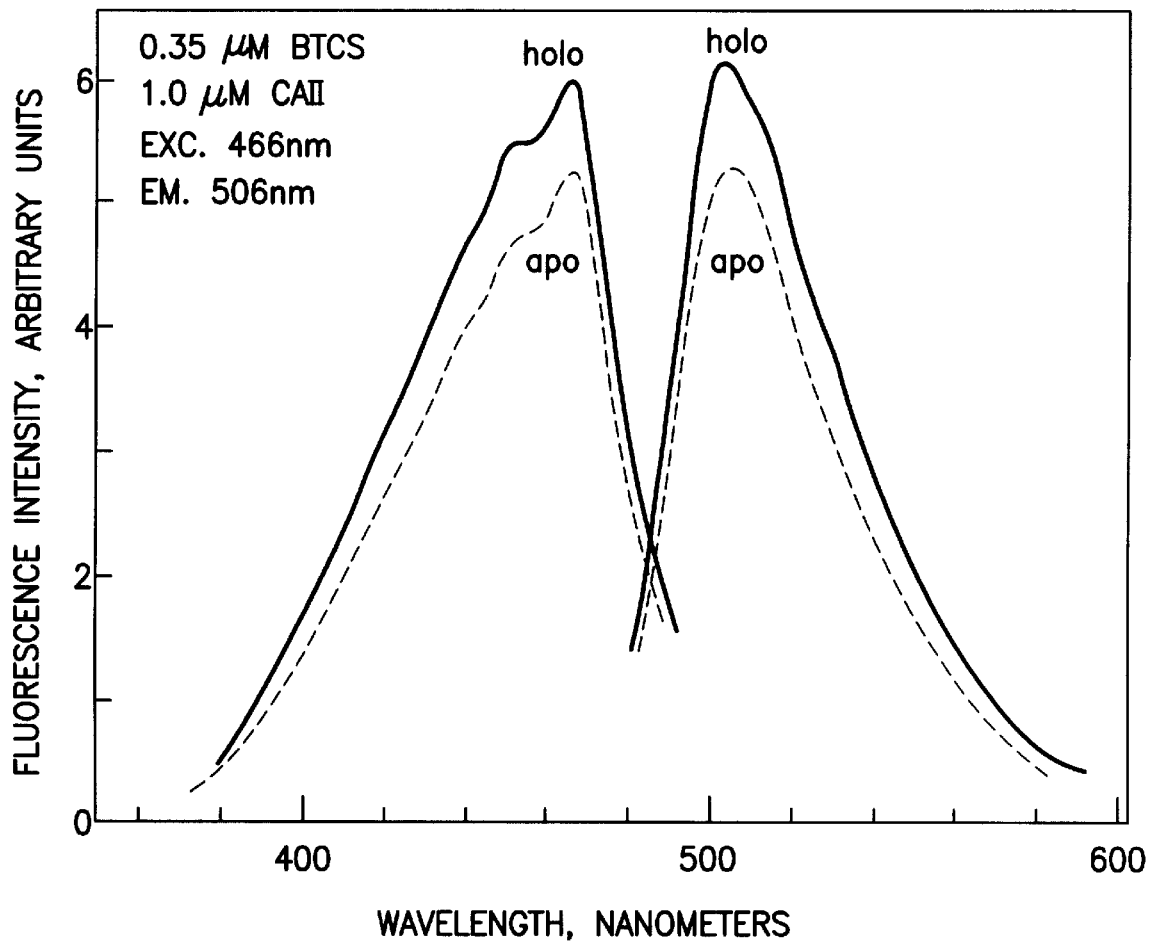
FIG. 23 shows normalized emission (peak at 504 nm) and excitation (peak at 466 nm) spectra of BTCS in the presence of apo- (- - - - -) and holocarbonic anhydrase II (___).
Figure 24:
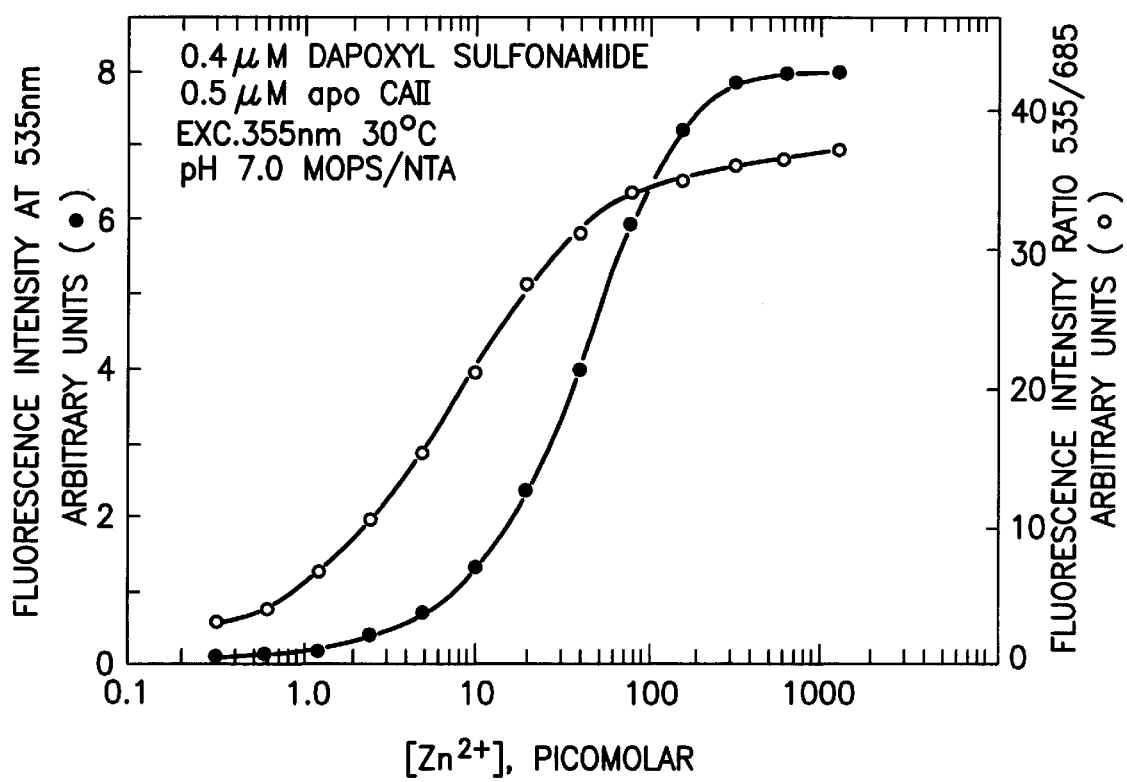
FIG. 24 shows fluorescence emission intensities for dapoxyl sulfonamide labeled apocarbonic anhydrase II at 535 nm (●) and intensity ratios (535 nm/685 nm) (○) as a function of zinc [Zn(II)] concentration.
Figure 25:
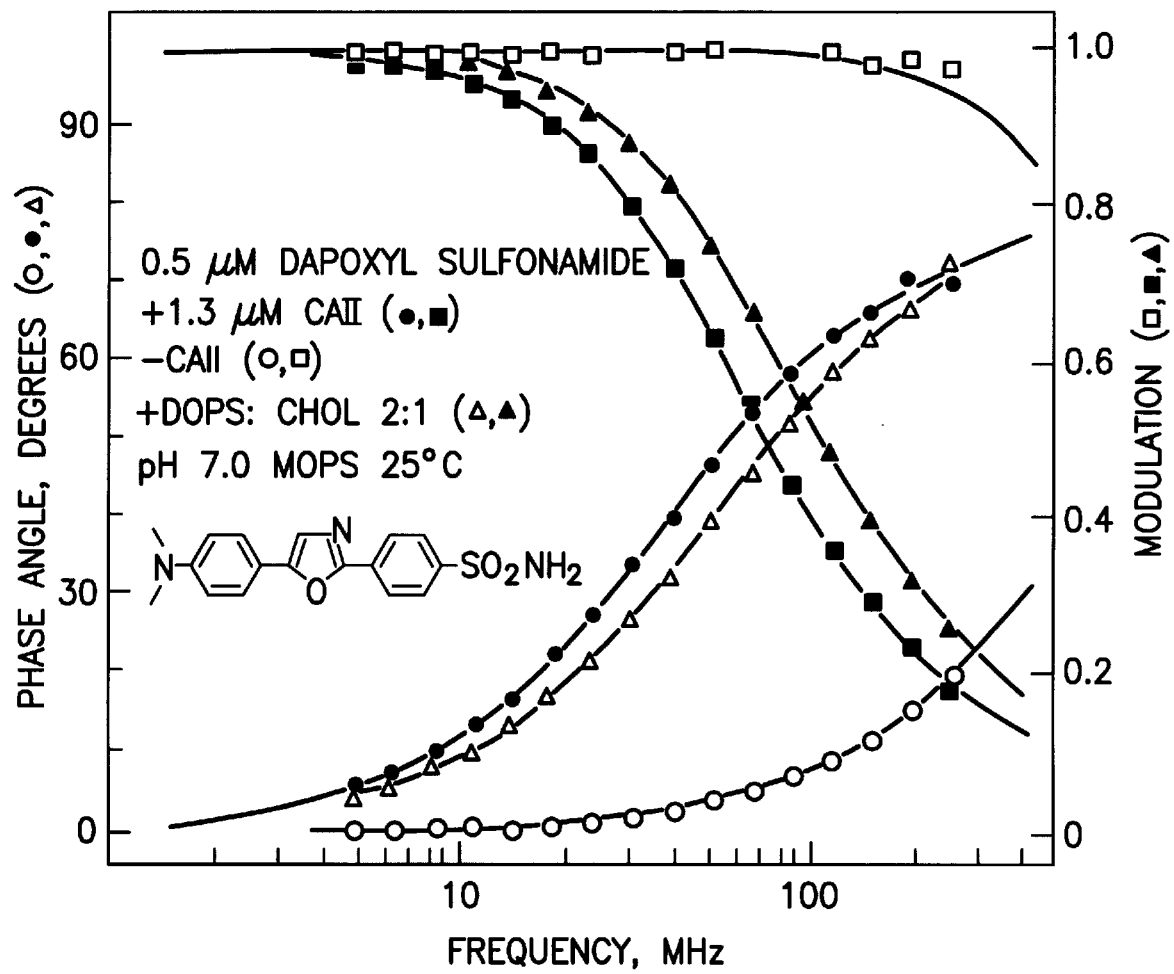
FIG. 25 shows frequency dependent phase shifts (Δ, ●, ○) and modulations (■, □, ▲) for dapoxyl sulfonamide free in solution (○, □), bound to DOPC: cholesterol vesicles (▲, △), and bound to holocarbonic anhydrase (●, ■).
Figure 26:
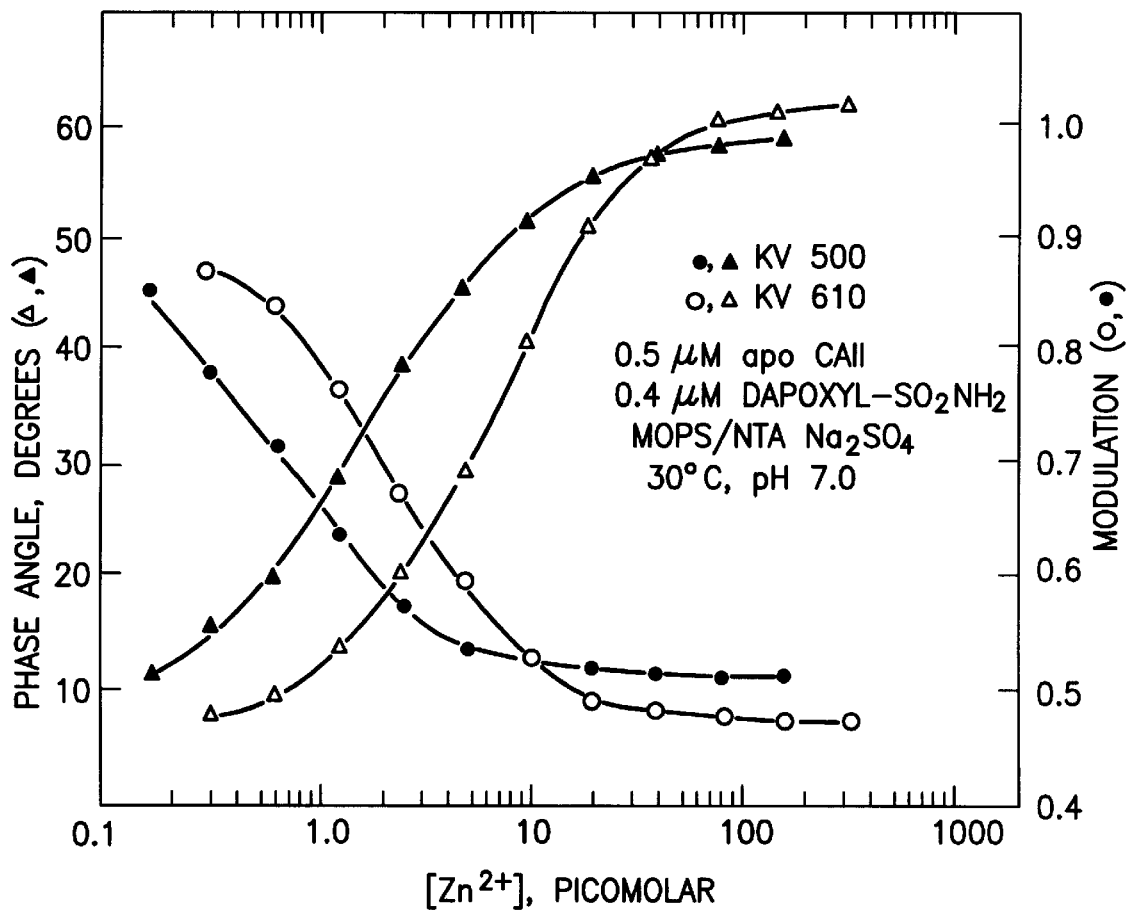
FIG. 26 shows frequency dependent phase shifts (△, ▲) and modulations (●, ○) for dapoxyl sulfonamide as a function of zinc [Zn(II)] concentration, with emission observed through KV 500 (●, ▲) or KV 610 (△, ○) barrier filters.

Dapoxyl sulfonamide, like dansylamide, exhibits a dramatic increase and blue shift in its fluorescence intensity upon binding to holocarbonic anhydrase, in comparison to its emission free in solution FIG. 22. In particular, emission of the bound form shifts from a peak at 605 nm to 530 nm, and increases about 90-fold, compared to the free form. The increase and large shift suggest that the fractions of Dapoxyl sulfonamide in the free and bound forms (determined by the zinc concentration) can be deduced by measuring the intensity, or the ratio of fluorescence intensities on the blue and red sides of the emission band. This is in fact the case: zinc-dependent intensity and intensity ratios are depicted in FIG. 24. The dramatic increase in intensity at 535 nm is apparent, as well as the ten-fold increase in 535 nm/685 nm intensity ratio. The advantages of intensity ratios for accuracy in quantitating concentrations of metal ions such as calcium are by now widely appreciated. These intensity changes permit the affinity of holocarbonic anhydrase for Dapoxyl sulfonamide to be determined as 0.3 M (data not shown). The intensity increase of dapoxyl sulfonamide is also accompanied by a large increase in fluorescence lifetime. We measured the frequency-dependent phase angles and demodulation of dapoxyl sulfonamide free in solution, in the presence of holocarbonic anhydrase II, and in the presence of sonicated unilamellar vesicles of DOPC/ cholesterol 3:1 (0.1 M). The results of these experiments are depicted in FIG. 25; the values of lifetime and fractional intensity derived from fitting these data are listed in Table 3 below. The twenty-fold increase in fluorescence lifetime accompanying Dapoxyl sulfonamide binding to the protein is unsurprising in view of the intensity increase, since we do not anticipate static quenching of the free probe per se. As we, Lakowicz, Wolfbeis, and others have shown, quantitating analytes by changes in fluorescence lifetime offers several advantages. Thus, we measured the zinc dependence of phase and modulation at 100 MHz as a function of free zinc concentration; the results are depicted in FIG. 26. The changes in phase and modulation are large enough to be very useful: the phase increases from 7 to 62 degrees on the red side of the emission band, with the modulation change being commensurate. These large changes make it readily apparent that Dapoxyl sulfonamide can easily be used for lifetime-based sensing.

The hydrophobic nature of Dapoxyl sulfonamide suggested that it might bind to phospholipid bilayers such as that in the cell membrane. In fact it does, exhibiting fluorescence in the presence of DOPC/cholesterol unilamellar vesicles which closely mimics its emission bound to carbonic anhydrase in color and lifetime (Table 3 and FIG. 25). When added to a rat brain hippocampal slice (results not shown) the dye stained a variety of cell membranes. Our preliminary results suggest that Dapoxyl sulfonamide partitions into membranes reversibly, as it will desorb from the membrane to bind to holocarbonic anhydrase. This suggests that Dapoxyl sulfonamide will bind to holocarbonic anhydrase present in the cell. This behavior would be different from that of ABD-N, which does not apparently penetrate the cell.

Figure 27:
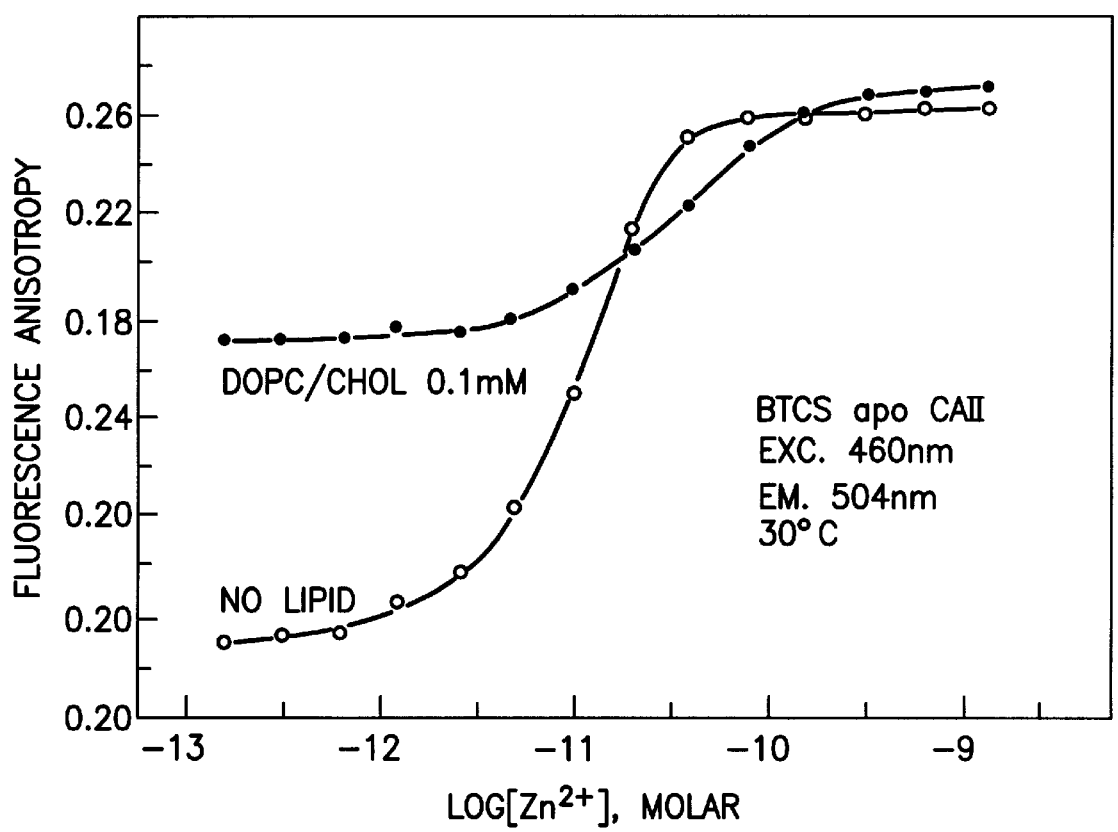
FIG. 27 shows fluorescence anisotropies of BTCS plus apocarbonic anhydrase as a function of free zinc in the absence (○) and presence (●) of 0.1 mM DOPC/cholesterol vesicles.
Figure 28:
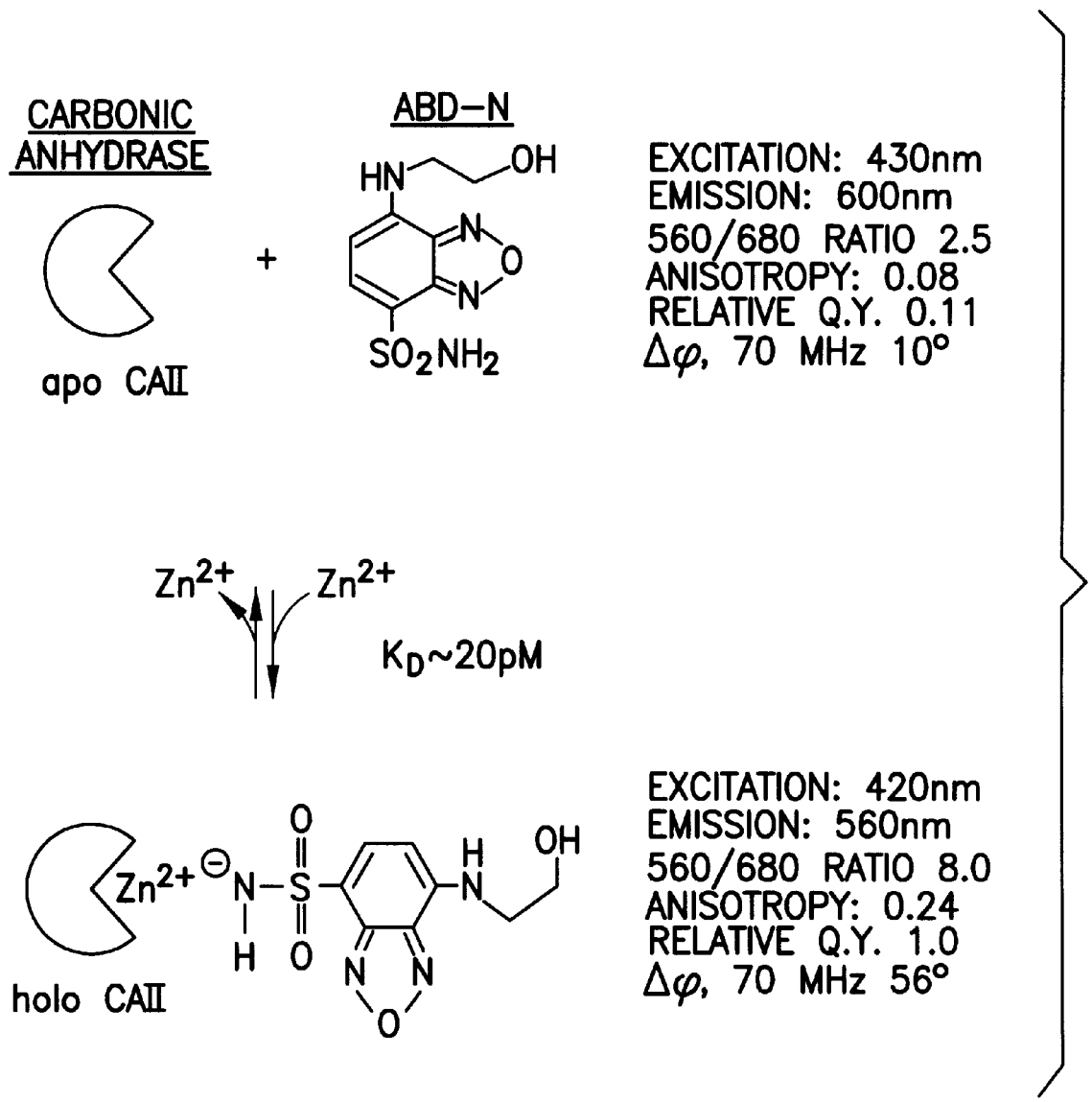
FIG. 28 shows fluorescence properties of ABD-N free in solution, and bound to holocarbonic anhydrase.
Figure 29:
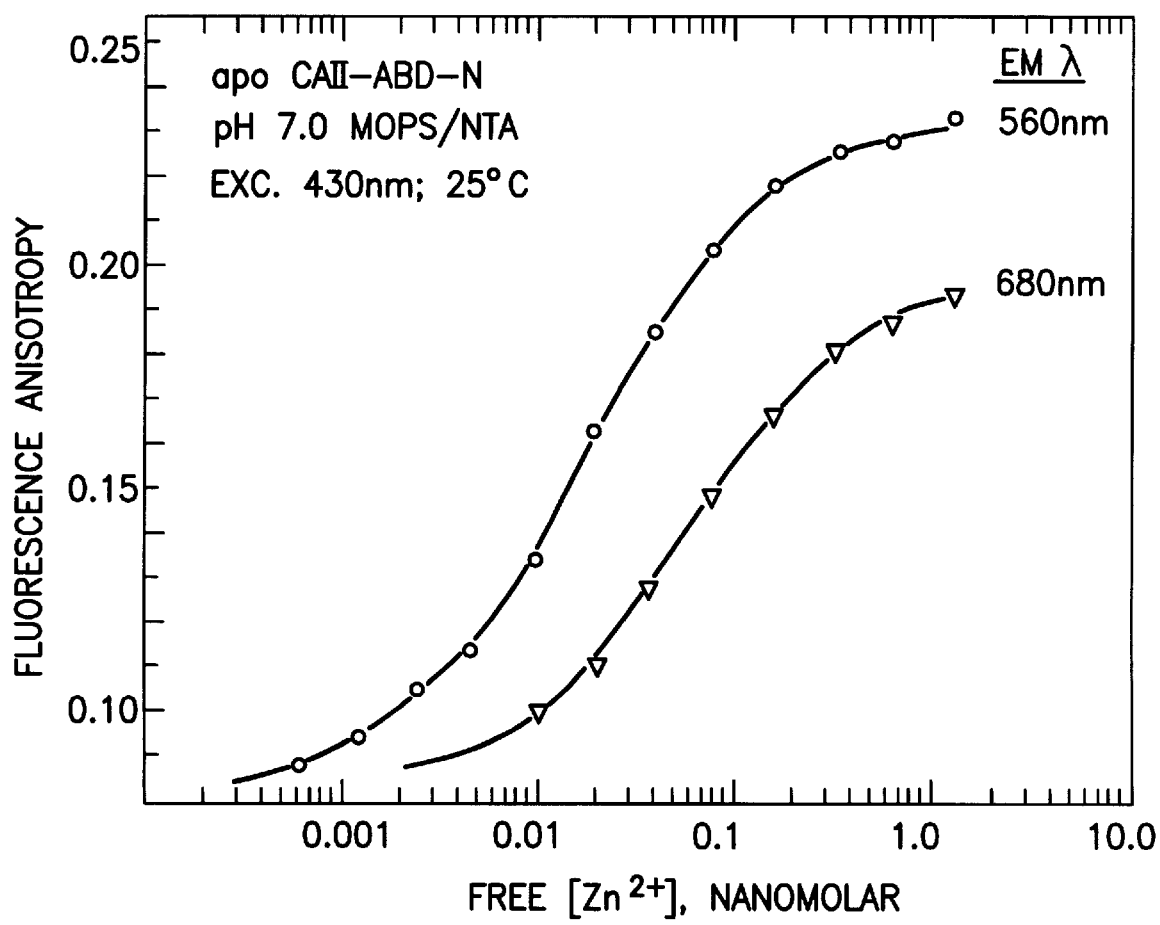
FIG. 29 shows fluorescence anisotropy of ABD-N labelled apo-carbonic anhydrase II as a function of free zinc [Zn(II)] concentration at emission wavelengths of 560 nm (○) and 680 nm (△), zinc concentrations buffered with 5–15 nM NTA at pH 7.0 with 10 mM MOPS.
Figure 30:
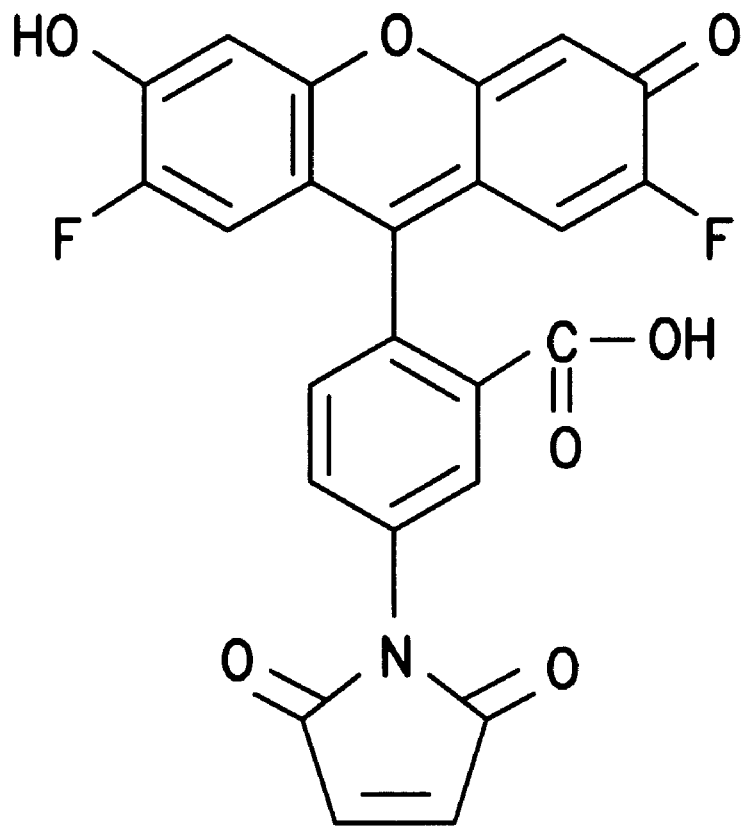
FIG. 30 shows the structure of Oregon Green™.
Figure 31:
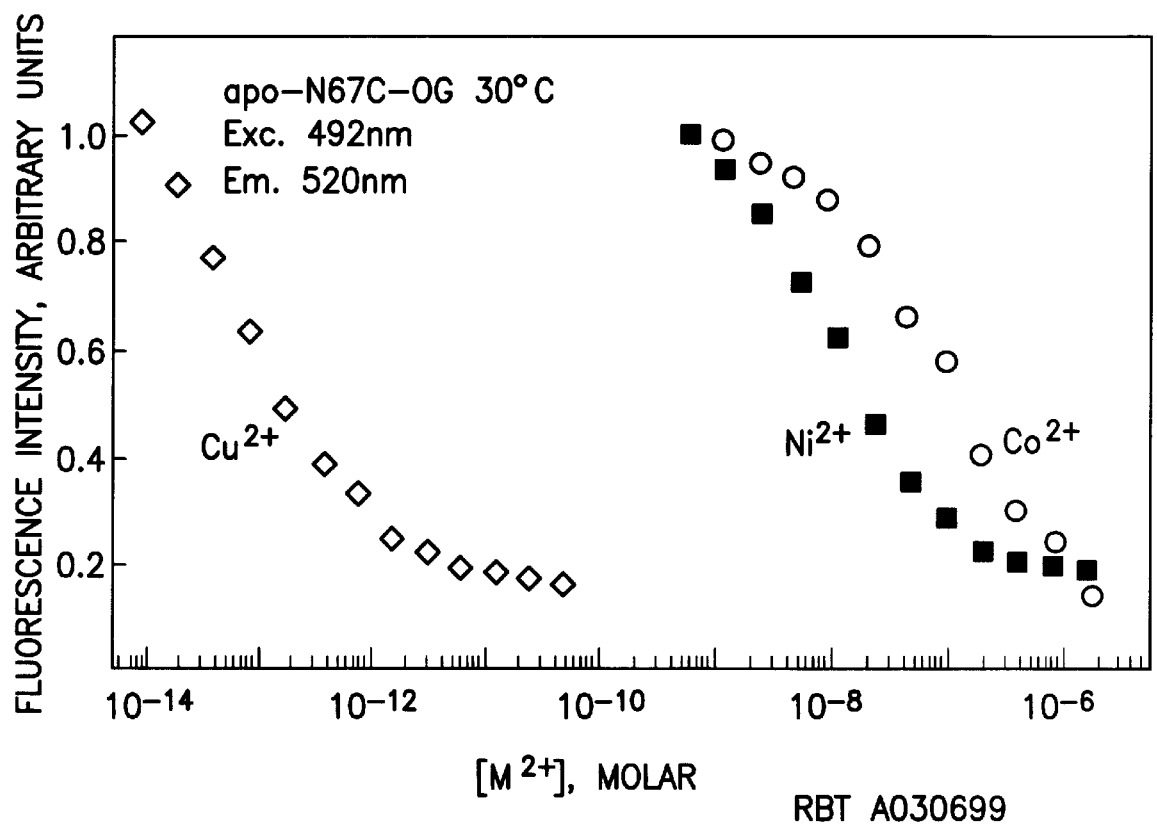
FIG. 31 depicts the fluorescence intensity (excitation 492 nm, emission 520 nm) of APO-N67C-Oregon Green™ as a Function of Cu(II) (◇), Ni(II) (■) or Co(II) (○) concentration.
Figure 32:
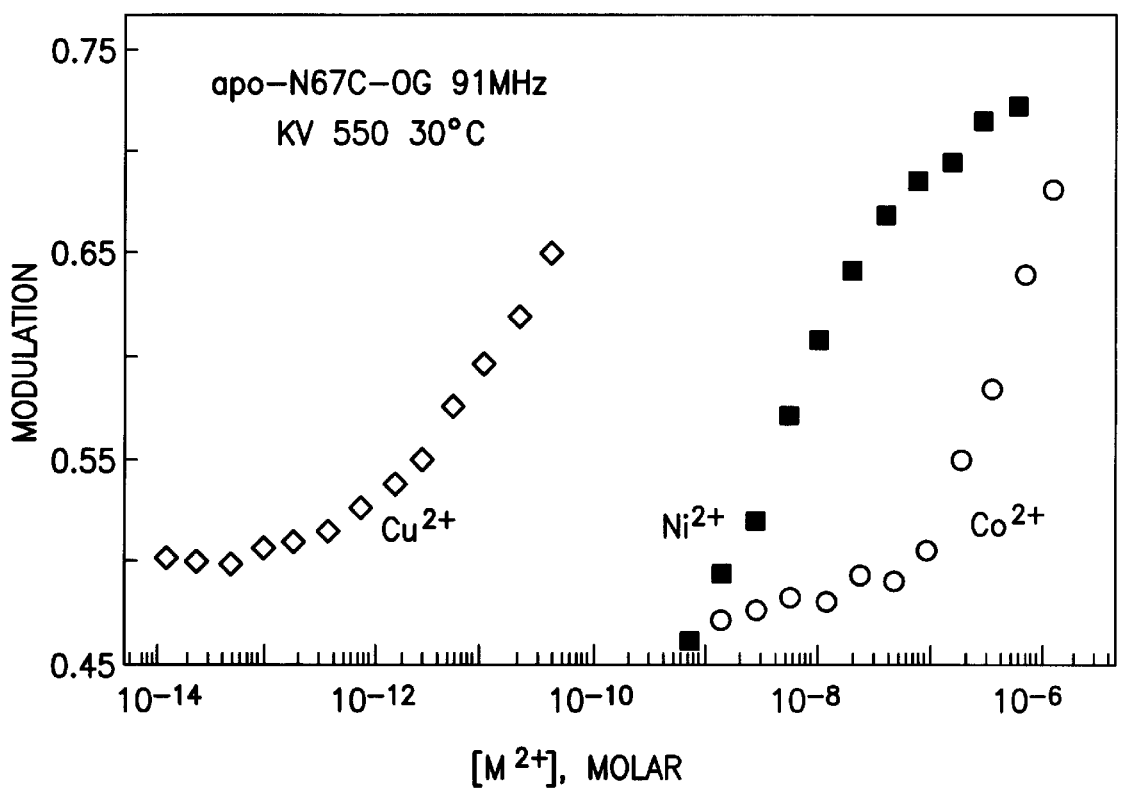
FIG. 32 depicts the modulation at 91 mHz of apo-N67C-Oregon Green™ as a function of Cu(II) (◇), Ni(II) (■) or Co(II) (○) concentration.
Figure 33:
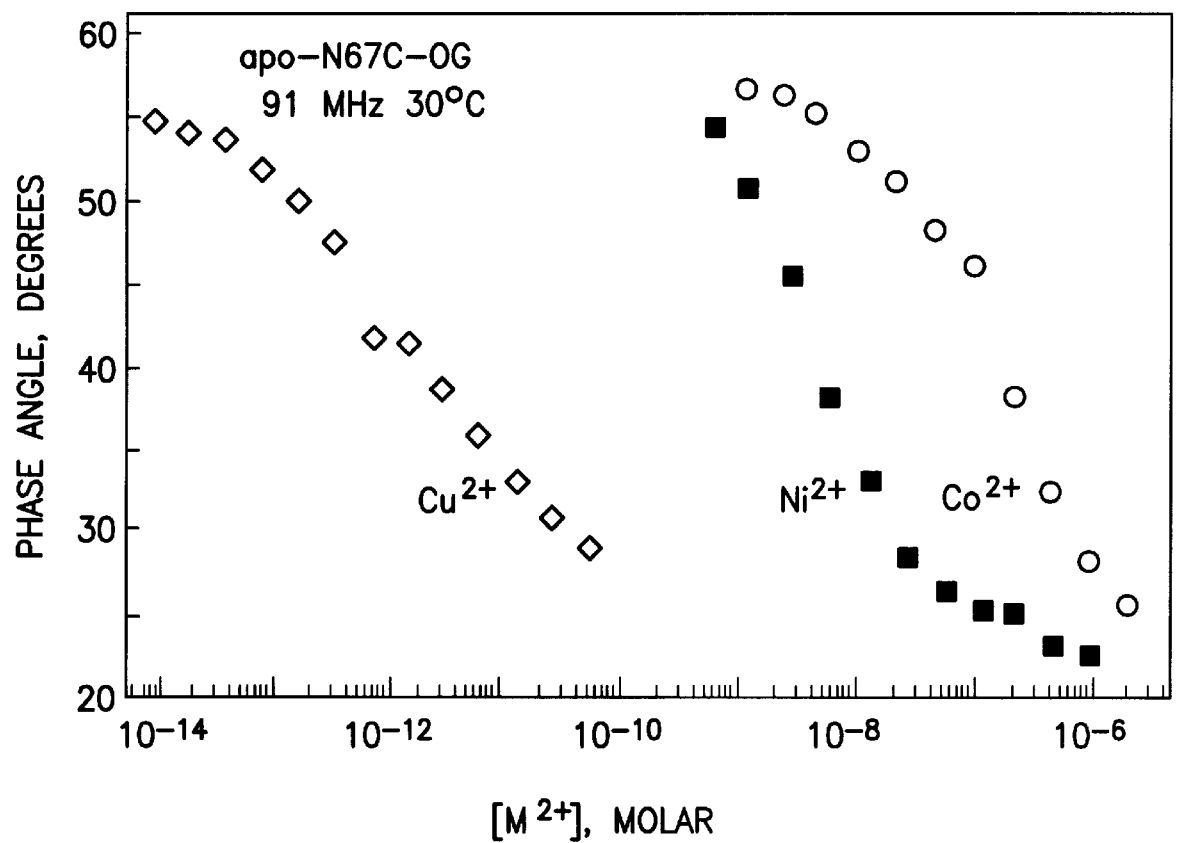
FIG. 33 depicts the phase angle at 91 mHz of apo-N67C-Oregon Green™ as a function of Cu(II) (◇), Ni(II) (■) or Co(II) (○) concentration.
Figure 34:
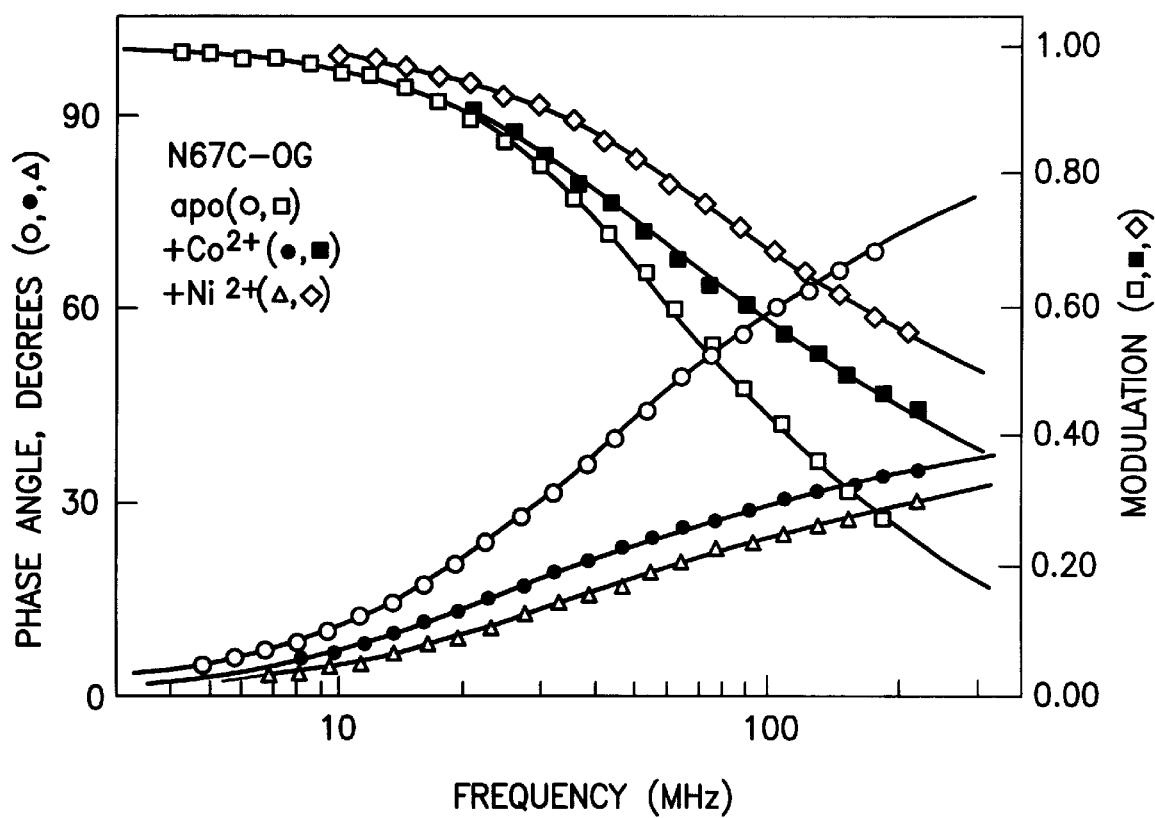
FIG. 34 depicts frequency-dependent phase shifts (○, ●, △) and demodulations (□, ■, ◇) of N67C-Oregon Green™ in the absence of metal (○, □), and saturated with Co(II) (●, ■) or Ni(II) (△, ◇). The lines indicate the best fit of the data.

Unlike Dapoxyl sulfonamide, BTCS exhibits little change in its fluorescence spectrum, intensity (FIG. 23), or lifetime Table 3 in the presence of holocarbonic anhydrase compared with free in solution. Thus it is modestly useful as an intensity, intensity ratio, or lifetime probe. However, the negligible change in lifetime (Table 3) makes BTCS an excellent anisotropy probe. In particular, the fluorescence anisotropy of BTCS in the presence of apocarbonic anhydrase exhibits a five-fold increase (from 0.05 to 0.25) as the binding site is saturated by increasing concentrations of free zinc ion in the picomolar range (FIG. 27). Moreover, BTCS also reversibly binds to phospholipid bilayers with a small change in lifetime (Table 3), but a substantial jump in anisotropy. We believe this binding is in fact a partitioning into the bilayer, as exhibited by many other non-polar molecules. An important feature of the anisotropy is that the anisotropy of BTCS bound to holocarbonic anhydrase is 50% higher than that of BTCS bound to the membrane (FIG. 27), suggesting that emission from BTCS bound to carbonic anhydrase inside cells could be resolved from that bound to the cell membrane. Moreover, this difference might be imaged by fluorescence anisotropy microscopy. Experiments are ongoing to test this proposition.

TABLE 3

| Sample[@] | $\tau_1$ | $f_{1-}$ | $\tau_2$ | $f_2$ | $x^2$ |
|---|---|---|---|---|---|
| Dapoxyl sulfonamide + holoCA | 3.80 ± 0.05 | 0.94 | 0.49 ± 0.04 | 0.06 | 10 |
| Dapoxyl sulfonamide | 0.22 ± 0.01 | 1.00 | | | 4.0 |
| BTCS + holoCA | 2.81 ± 0.05 | 0.93 | 1.35 ± 0.29 | 0.07 | 0.9 |
| BTCS | 2.63 ± 0.11 | 0.90 | 1.65 ± 0.56 | 0.10 | 1.3 |
| BTCS + DOPC/Cholesterol 3:1 | 2.56 | 1.00 | | | 0.9 |

[@]"Sample" refers to the experimental sample, $*_i$ is the lifetime of the component i in the nanoseconds, $f_i$ is the fractional intensity of the component i, and $0^2$ is the reduced chi-squared, a measure of the goodness of fit.

ABD-N

The embodiment herein reacts by scheme 1 described above. Although the results discussed below are directed to specific sensing methods, it is important to note that ABD-N can be utilized in lifetime, intensity, and wavelength shift based sensing methods.

Genes for wild type human carbonic anhydrase II and variants were isolated, constructed, and expressed in *E. coli* as previously described. ABD-N was synthesized by coupling ABD-F (Molecular Probes, Eugene, Oreg.) with excess ethanolamine in DMF at room temperature for 4 hours and lyophilizing. Zn(II) was removed from holo-CA to make apo-CA by treatment with dipicolinate as previously described. Fluorescence anisotropy measurements were obtained on an SLM AB-2 spectrophotofluorimeter according to the manufacturer's recommendations, under the spectral conditions given in the figures. Low free metal ion concentrations were maintained with the metal ion buffers listed in the figures.

Figure 36:
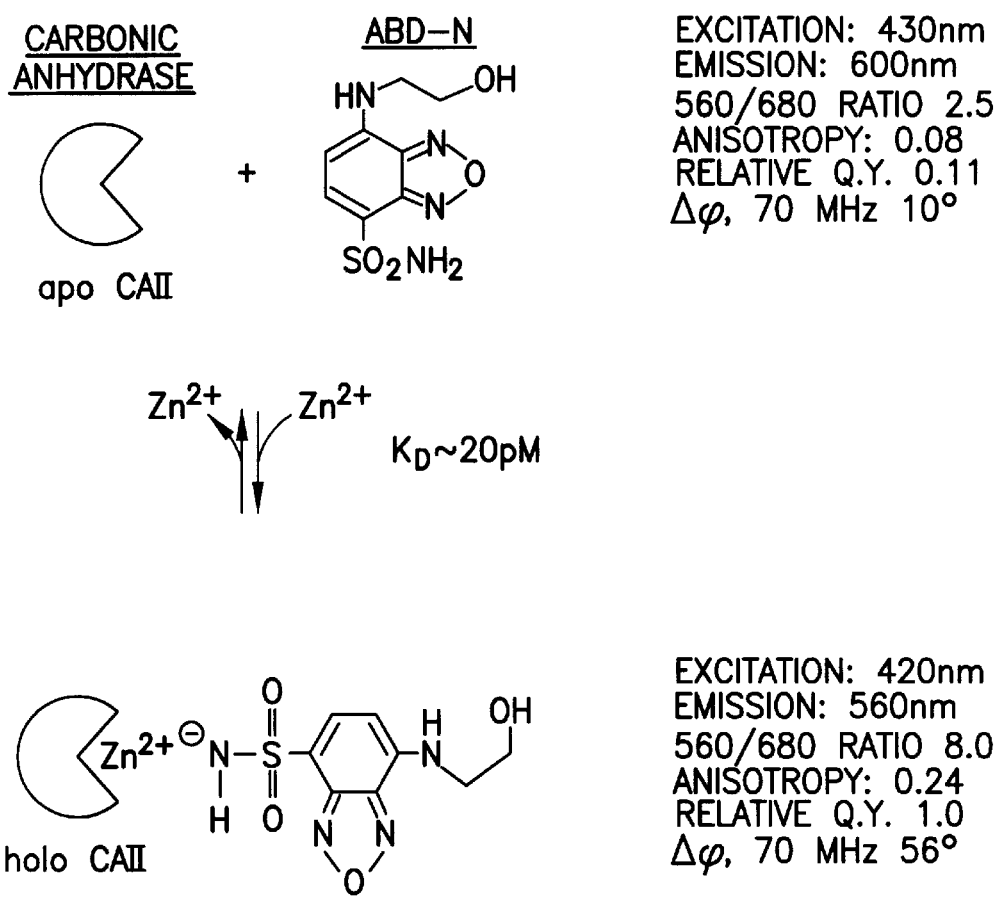
FIG. 36 shows fluorescence properties of ABD-N free in solution, and bound to holocarbonic anhydrase.
Figure 37:
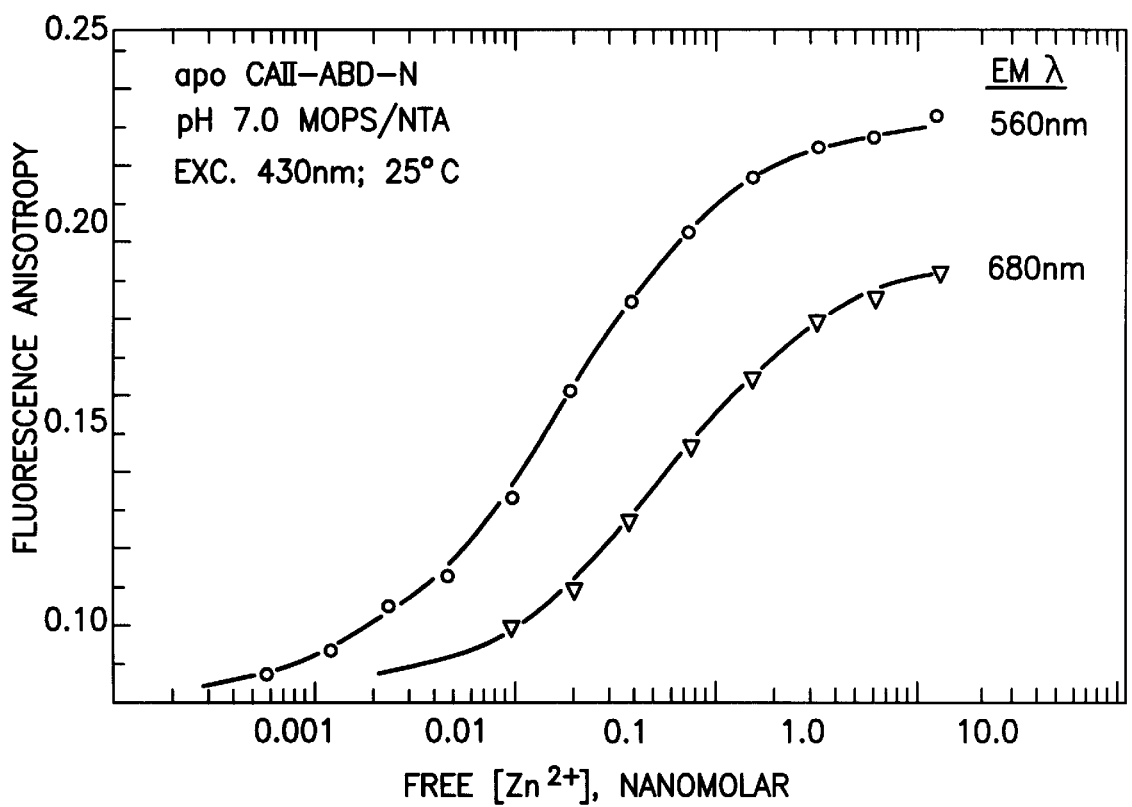
FIG. 37 depicts fluorescence anisotropy of ABD-N plus apocarbonic anhydrase as a function of free Zn(II) concentration at emission wavelengths of 560 nm (○) and 680 nm (△). Free Zn concentration was buffered with 5–15 mM nitrilotriacetic acid, pH at 7.0 with 10 mM MOPS.

ABD-N was originally selected because we sought a new fluorescent aryl sulfonamide which would be excitable in the visible (unlike dansylamide), but which would be closely coupled with the overall rotational motion of CA when it was bound, to exhibit the maximum anisotropy change. In fact, ABD-N performs rather well in this regard, exhibiting a ten-fold increase in intensity and a significant shift in excitation and emission spectra upon binding to the holo-CA [FIG. 36], but no apparent change in the presence of the apoprotein. The changes in anisotropy are also dramatic, going from 0.08 to 0.23 as the apoprotein becomes saturated with Zn(II) (FIG. 37); the ordinary accuracy and precision of such measurements is ±0.003. The apparent $K_D$ of the enzyme for Zn(II) under these conditions is about 20 picomolar, which is somewhat higher than published values obtained under slightly different conditions. Thus the present system exhibits sensitivity for free Zn(II) about one hundredfold better than previous fluorescence methods.

Figure 38:
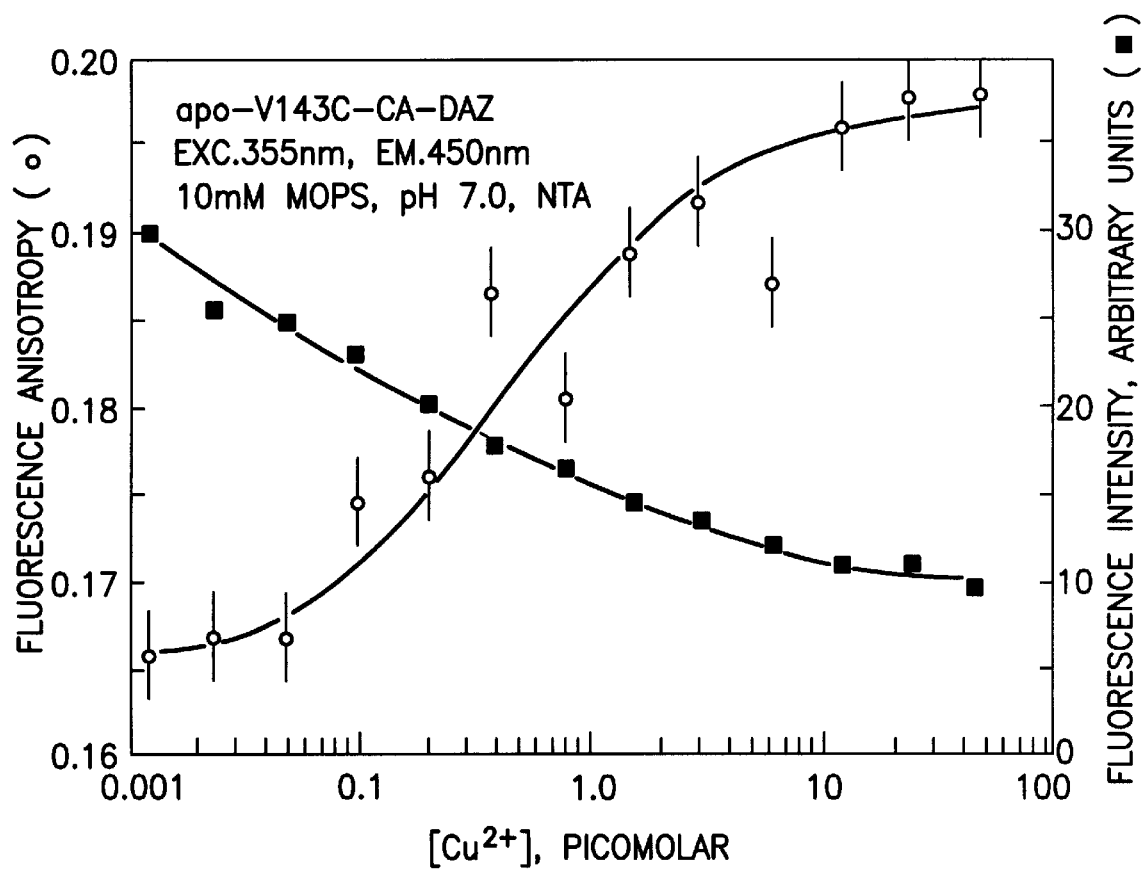
FIG. 38 shows fluorescence intensity (■) and anisotropy (○) of apo-V143C-CA labeled with danzsylaziridine as a function of free Cu(II) concentration. Free copper ion concentration was buffered with 5–15 mM nitrilotriacetic acid, pH at 7.0 with 10 mM MOPS.

The use of a separate, diffusible inhibitor like ABD-N can create difficulties, however. The concentrations of inhibitor and apo-CA must be low enough so that the least possible amount of Zn(II) creates significant saturation, but high enough over the $K_D$ of the inhibitor for the holoprotein (about 0.3 uM) to assure that the inhibitor binds. This may not be easy to achieve, and consequently we sought to attach the inhibitor to the CA molecule to avoid this problem. We had found previously that some fluorescent labels exhibit energy transfer with a concomitant diminution of the lifetime when placed in reasonable proximity to the CA active site when it contained bound Cu(II) instead of Zn(II). CA binds Cu(II) about ten-fold more tightly ($K_D$=0.1 pM) than Zn(II) (K. McCall and C. A. Fierke, unpublished results). In a fairly predictable fashion, declines in fluorescence lifetime result in increases in anisotropy which can be significant if the unquenched lifetime is reasonably comparable to the rotational correlation time of the enzyme (20 nsec). In this case we have site-specifically labeled CA at a residue close to the active site (V143C) with a relatively small dye, dansyl aziridine. We demonstrated that this labeled CA was sensitive to very low concentrations of free Cu(II) as judged by changes in its fluorescence intensity and anisotropy to picomolar and subpicomolar concentrations (FIG. 38). In particular, the apoV143C-CA-DAZ exhibited a significant decline in intensity and a modest increase in fluorescence anisotropy, both centered at a concentration close to its known affinity constant. The slight increase in anisotropy upon Cu(II) binding is not fully comparable with the decline in intensity (and lifetime, results not shown), and suggests some alteration in probe mobility upon binding. This Cu(II) determination, while clearly representing a modest response, cannot be due to simple collisional quenching by the Cu(II) at these low concentrations, and furthermore is more than one thousand-fold more sensitive than previous fluorescence-based determinations of Cu(II). The rapid decay (average lifetime about 4 nsec) exhibited by the dansyl aziridine in this example is shorter than desirable for this determination; a three-fold greater lifetime would have been preferable given the rotational correlation time of the carbonic anhydrase.

Figure 39:
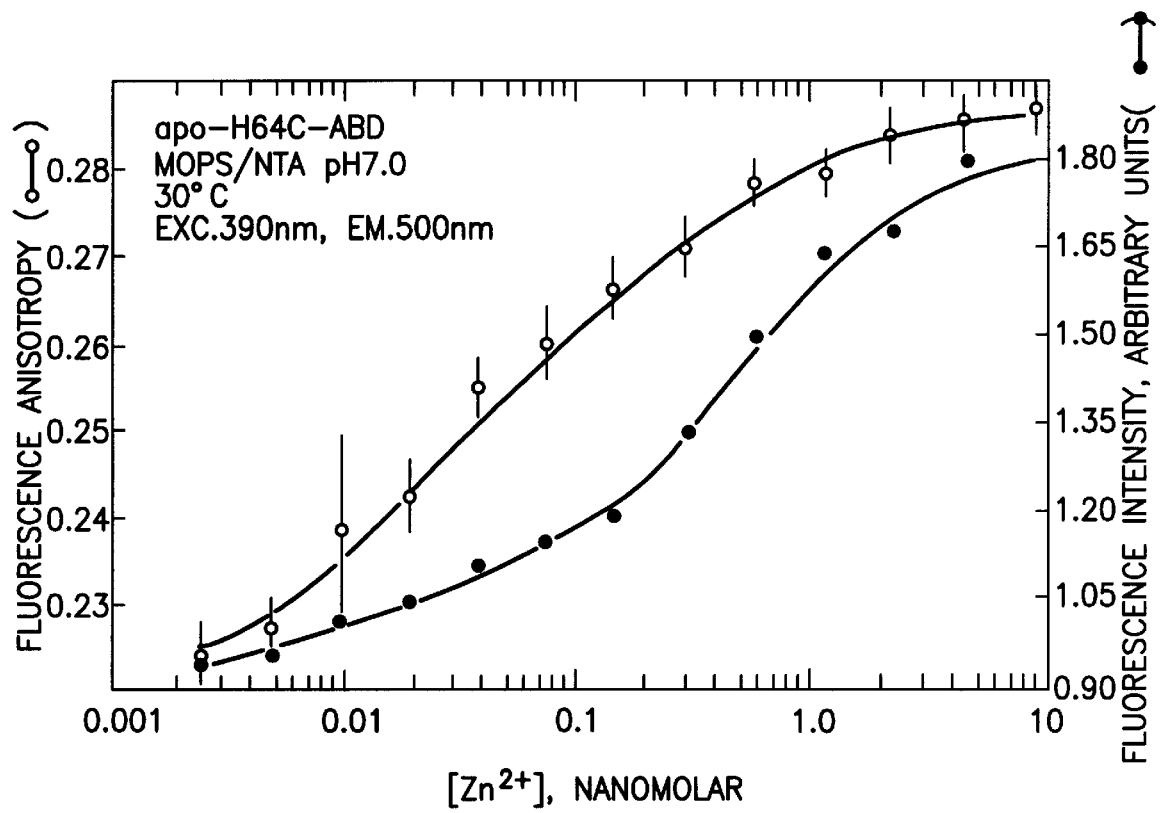
FIG. 39 depicts fluorescence intensity (●) and anisotropy (○) of apo-H64C-CA labeled with ABD-F as a function of free Zn(II) concentration; free Zn(II) buffered with nitrilotriacetic acid.

Finally, we also attached the reagent ABD-F to a slightly different variant, H64C, in the hope that the sulfonamide moiety of the label would be in close enough proximity to the zinc (when it is present in the active site) to become ionized and consequently exhibit a spectral shift. In this case, no shift was observed upon binding of zinc to apo-H64C-ABD, suggesting that the sulfonamide did not ionize. Interestingly, the binding of zinc was accompanied by an increase in intensity and average lifetime, but also with an increase in fluorescence anisotropy [FIG. 39]. This is not the expected result according to Perrin's equation, and we attribute the change in anisotropy to a substantial change in the mobility of the probe in the presence of the zinc; the probe is positioned on the edge of the active site cleft, within 10 angstroms of the Zn(II). In this example, the fluorescence anisotropy change is large enough to be readily measured with good accuracy. We also note that ABD can be excited at low concentrations and near the peak of its excitation polarization spectrum by the HeCd laser at 442 nm. The apparent Kd for zinc evident in FIG. 39 is about 40 picomolar, about forty-fold higher than the Kd for zinc of the wild type enzyme. However, those determinations were made under slightly different conditions, using an unmodified enzyme, and thus small differences are to be expected. The apparent detection limit is 4 picomolar, which is about two orders of magnitude less than that achievable using other fluorescence methods, and comparable to detection limits using other methods.

ABD-F and ABD-T

The embodiment herein reacts by scheme 2 described above. Although the results discussed below are directed to anisotropy methods, it is important to note that ABD-T can be utilized in lifetime, intensity, and, to a lesser extent, wavelength shift based sensing methods.

We have demonstrated that free metal ions such as Zn(II) can be determined by fluorescence anisotropy (polarization) using an apometalloenzyme, carbonic anhydrase II, and a fluorescent aryl sulfonamide inhibitor of the enzyme whose affinity for the enzyme is metal-dependent. We postulated that attaching the fluorescent aryl sulfonamide to the protein would provide a similar response, while avoiding problems of disproportionation of the inhibitor and protein. In fact a tethered aryl sulfonamide ABD-T gave very good results: Zn(II) and Cu(II) at picomolar levels and Co(II), Cd(II), and Ni(II) at nanomolar levels can all be determined by changes in fluorescence intensity, anisotropy, and lifetime using visible excitation sources.

Figure 40:
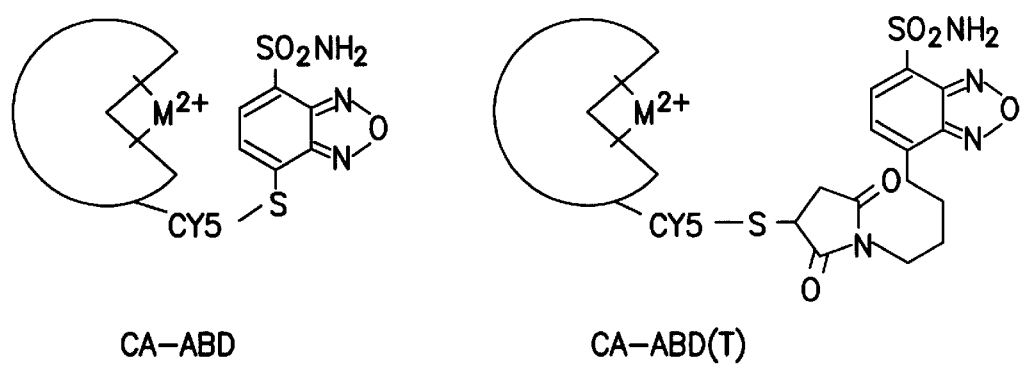
FIG. 40 shows the structure of ABD-F (left) and ABD-T (right) conjugated to cysteine residues on carbonic anhydrase.

The structure and synthesis of ABD-F and ABD-T are shown in FIG. 40. While ABD-F is available commercially, ABD-T was custom synthesized because molecular modeling strongly suggested that no matter where ABD-F was attached to the CA polypeptide chain, it could not be properly oriented for its aryl sulfonamide to serve as a fourth ligand to the protein-bound zinc, and thereby exhibit the spectroscopy of the sulfonamide anion. By comparison, the six-carbon tether in ABD-T should permit the probe to orient as a fourth ligand. The responses of fluorescent-labeled CA's incorporating the ABD-T label are described below.

Figure 41:
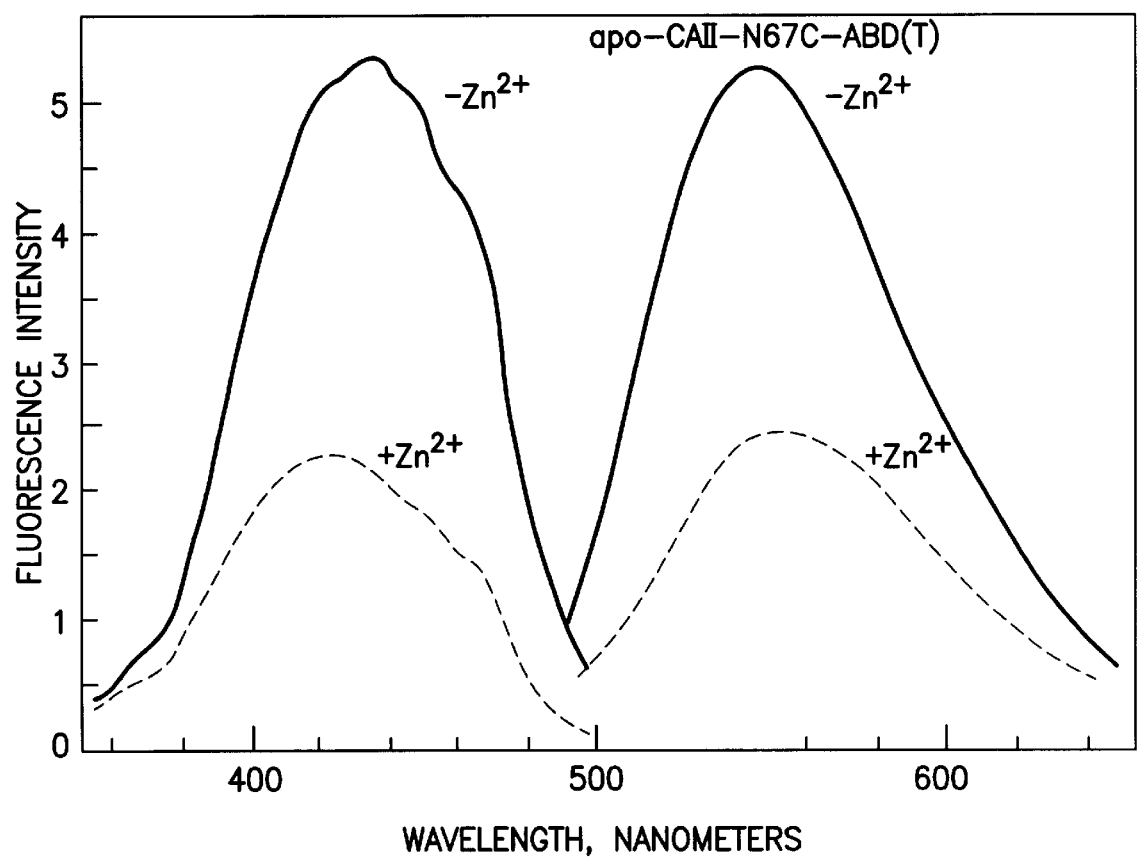
FIG. 41 shows fluorescence excitation (emission at 560 nm) and emission (excitation at 440 nm) spectra of apo-N67C-ABD-T in the presence (- - - -) and absence (___) of Zn (II).
Figure 42:
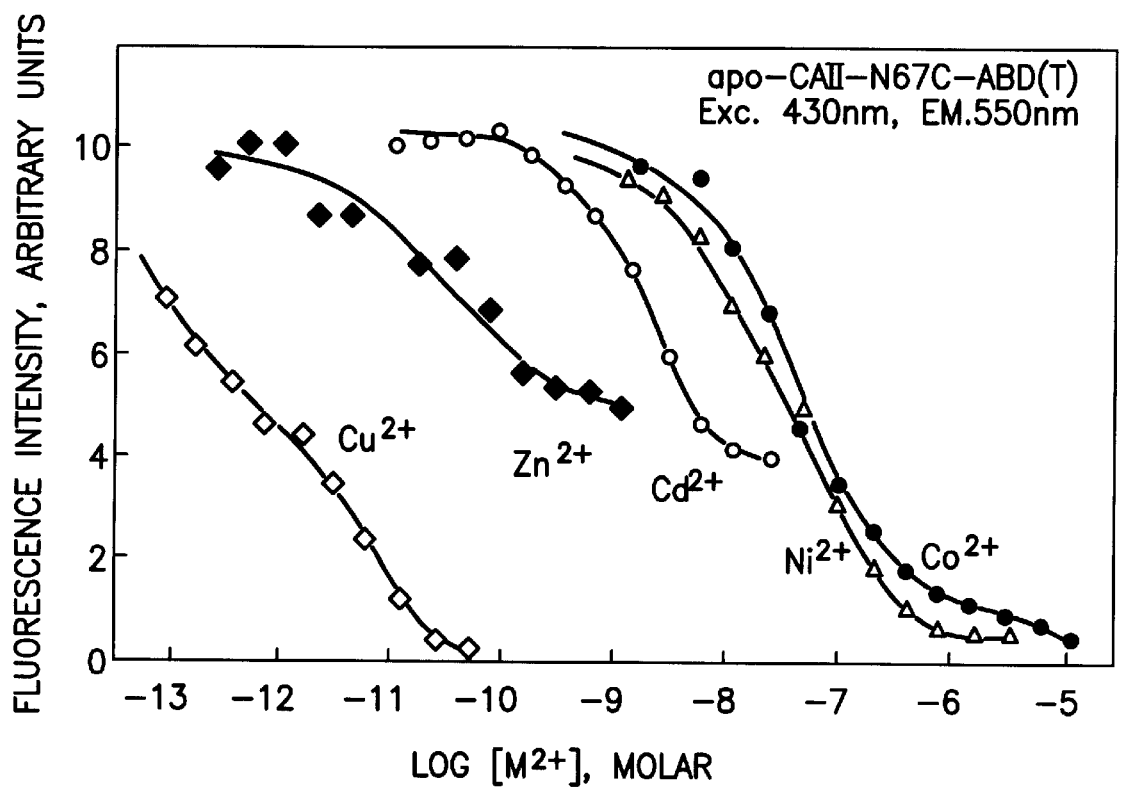
FIG. 42 shows fluorescence intensities of apo-N67C-ABD-T (excitation at 430 nm, emission at 550 nm) as a function of free Cu(II) (◇), Zn(II) (♦), Cd(II) (○), Ni (II) (△), and Co(II) (●) concentrations.
Figure 43:
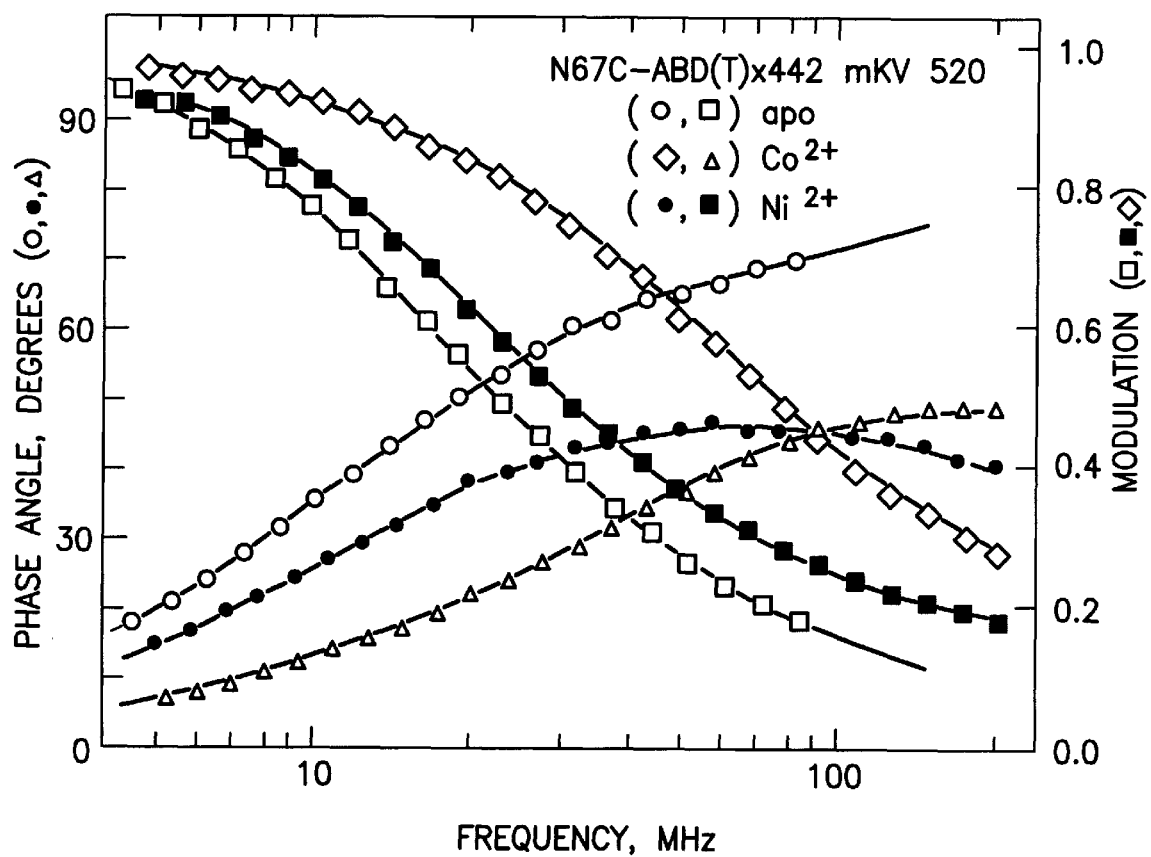
FIG. 43 shows frequency dependent phase shifts (●, ○, △) and demodulations (□, ■, ◇) of N67C-ABD-T (excitation at 442 nm, emission at 520+ nm) in the absence of metal (□, ○) and saturated with Co(II) (△, ◇) or Ni (II) (●, ■).

Site-directed mutants of carbonic anhydrase were prepared, conjugated to fluorophores, and the in vivo Zn(II) ion removed as previously described. ABD-F (7-fluorobenz-2-oxa-1,3-diazole-4-sulfonamide) was a product of Molecular Probes (catalog no. F-6053) and ABD-T (7-(5-maleimidyl)-pentylaminobenz-2-oxa-1,3-diazole-4-sulfonamide) was custom synthesized by them. Fluorescence spectra and anisotropies were measured on a Spectronics Instruments AB-2, and fluorescence lifetime data were obtained on an ISS K-2 frequency domain instruments using Rose Bengal in ethanol as a reference, essentially as previously described. Low free concentrations of metals ions were reproducibly made with the use of Bicine or nitrilotriacetic acid as metal ion buffers and the low metal affinity MOPS as pH buffer as will be described elsewhere (C. A. Fierke and K. McCall, unpublished results). When conjugated to a suitable site-directed mutant of CA such as N67C, ABD-T exhibits significant intensity changes upon binding of certain transition metal ions. The excitation and emission spectra of the labeled protein in the presence and absence of Zn(II) are depicted in FIG. 41. The excitation at 440 nm and emission at 540 nm both undergo slight shifts and the apparent intensity declines about 55% upon binding zinc ion. The fluorophore is almost ideally excited by the 442 nm line of the HeCd laser, with the 457 nm Ar line being nearly as good. In fact the intensity declines upon binding of any of several different metal ions, as depicted in FIG. 42. The apparent $K_D$'s, as judged from the concentrations corresponding to the steepest portions of the sigmoidal curves, are in quite good agreement with the known binding affinities of these metals to wild type apo-CA, although some slight variation is observed and may be attributed to the ABD-T label perturbing the affinity to a minor extent. Unlike ABD-T, ABD-F when conjugated to N67C exhibits increases in intensity upon metal ion binding which we attribute to a decrease in a static quenching mechanism when the binding site is filled. In a manner consonant with the observed intensity changes ABD-T exhibits substantial changes in its fluorescence lifetime(s) upon binding metals. We measured the frequency-dependent phase shifts and modulations of apo-N67C-ABD-T in the absence and presence of various metals, and used those data to infer the decay properties of the sample using a fitting process; those data are shown for the apoprotein, and in the presence of Co(II) and Ni(II) (FIG. 43). Clearly there are dramatic changes in the lifetime as judged from the data and the lines indicating the best fits to those data; the best fit parameters are collected in Table 4.

TABLE 4

| Sample@ | $\tau_1$ | $f_1$ | $\tau_2$ | $f_2$ | $\tau_3$ | $f_3$ | $<\tau>$ | $x^2$ |
|---|---|---|---|---|---|---|---|---|
| apo-N67C-ABD-T | 15.80 ± .20 | 0.38 | 10.56 ± .08 | 0.56 | 1.18 | 0.06 | 11.98 | 0.6 |
| apo + Zn(II) | 14.35 ± .75 | 0.15 | 6.48 ± .05 | 0.84 | 0.82 | 0.01 | 7.54 | 1.3 |
| apo + Cd(II) | 10.53 ± .15 | 0.35 | 5.48 ± .04 | 0.56 | 0.83 | 0.09 | 6.82 | 0.6 |
| apo + Ni(II) | 13.89 ± .70 | 0.27 | 5.82 ± ND | 0.41 | 0.71 | 0.33 | 6.30 | 1.7 |

TABLE 4-continued

| Sample@ | $\tau_1$ | $f_1$ | $\tau_2$ | $f_2$ | $\tau_3$ | $f_3$ | $<\tau>$ | $x^2$ |
|---|---|---|---|---|---|---|---|---|
| apo + Cu(II) | 10.56 ± .25 | 0.35 | 4.05 ± .05 | 0.57 | 0.58 | 0.10 | 5.89 | 2.1 |
| Apo + Co(II) | 13.14 ± .32 | 0.24 | 3.59 ± ND | 0.68 | 0.80 | 0.08 | 5.68 | 0.6 |

@"Sample" refers to the experimental sample, $\tau_i$ is the lifetime of the component i in nanoseconds, $f_i$ is the fractional intensity of the component i, $<\tau>$ is the average lifetime, and $x^2$ is the reduced chi-squared, a measure of the goodness of fit.

Figure 44:
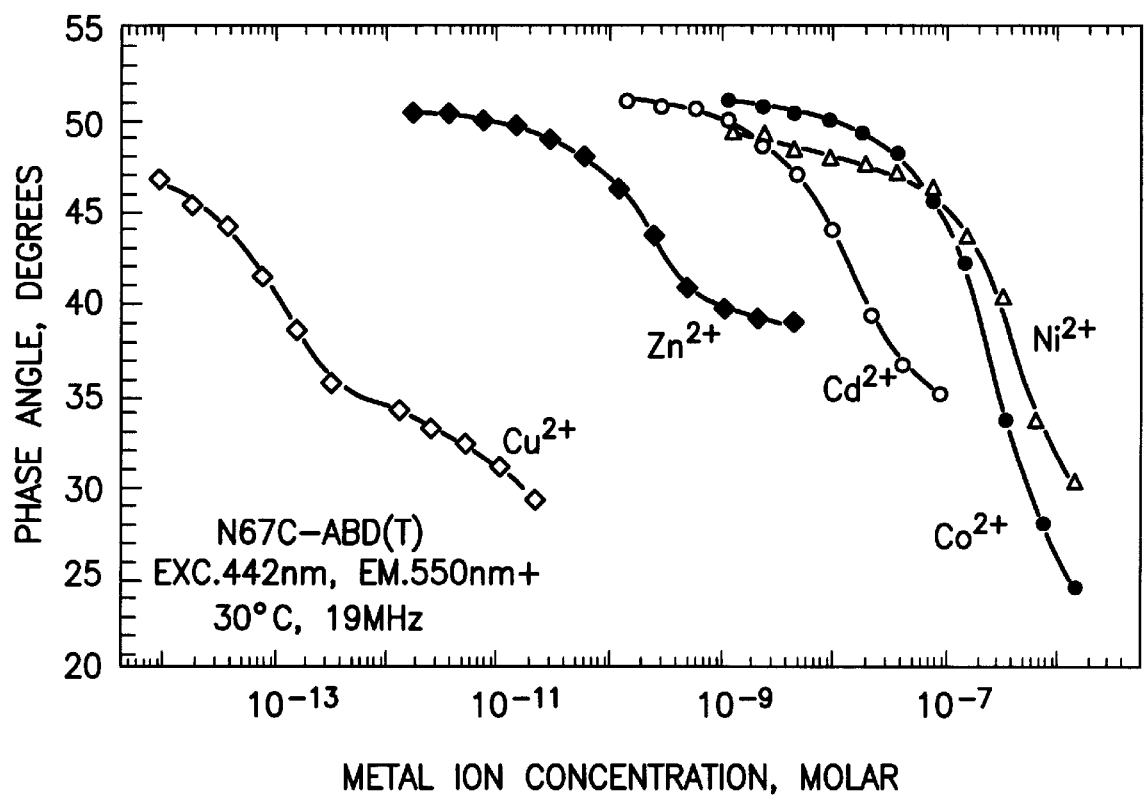
FIG. 44 shows phase angles at 19 MHz for apo-N67C-ABD-T (excitation 442 nm, emission at 550+ nm) as a function of the concentration of Cu(II) (◇), Zn(II) (♦), Cd(II) (○), Co(II) (●) and Ni (II) (△).
Figure 45:
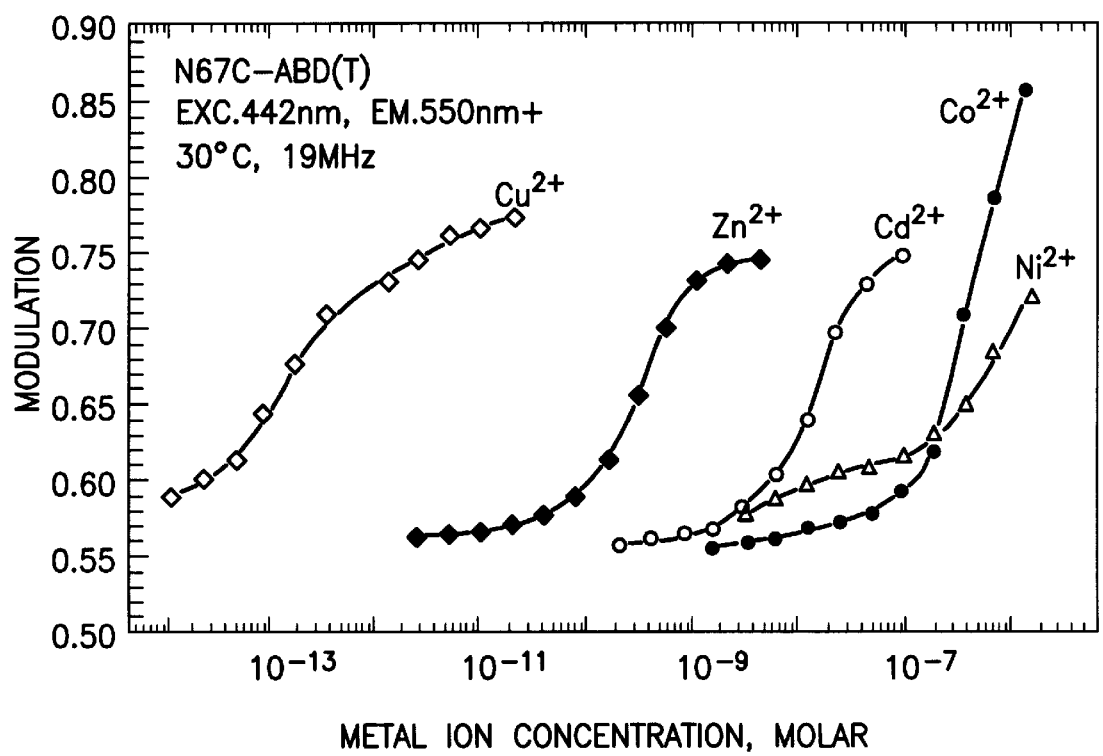
FIG. 45 shows modulations at 19 MHz for apo-N67C-ABD-T (excitation 442 nm, emission at 550+ nm) as a function of the concentration of Cu(II) (◇), Zn(II) (♦), Cd(II) (○), Co(II) (●) and Ni (II) (△).

These dramatic changes in phase angle and modulation at suitable frequencies can be used to determine the fractional occupancy of the binding site by the metal, and consequently the free concentration. In fact at the relatively low modulation frequency of 19 MHz the phase and modulation of the emission of ABD-T-N67C exhibits an excellent response to all the metals tested. This may be seen in FIGS. 44 and 45, which plot the phases and modulations, respectively, of apo-ABD-T-N67C as a function of metal ion concentration. The changes in phase angle, for instance, are as large as 15 degrees for Cd(II), and more than 20 degrees for Cu(II) (likely due to binding at a second, somewhat weaker site. These changes are quite usable inasmuch as the ordinary accuracy and precision of a phase angle measurement is less than 0.3 degrees. The modulation changes are comparably large, with Zn(II) increasing modulation by a full 20% upon binding. Again, the precision of modulation measurements is ordinarily of the order of a few parts per thousand, so using such measurements to determine free metal ion concentrations is clearly feasible.

Figure 46:
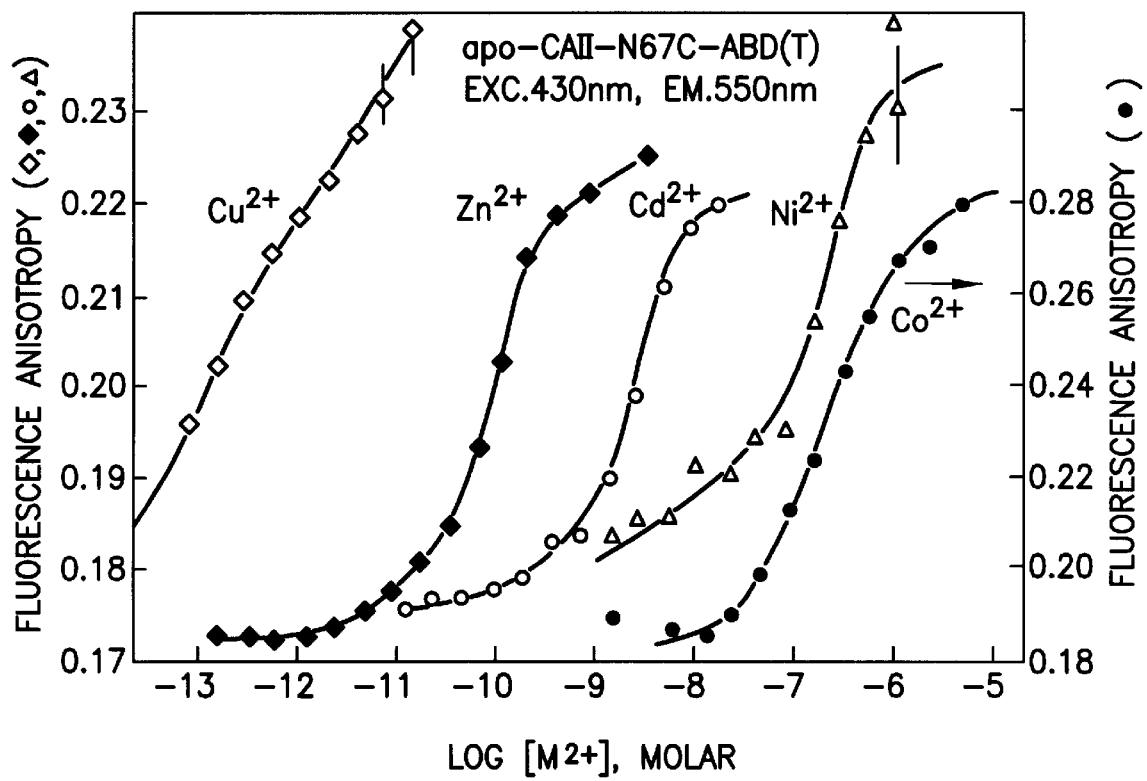
FIG. 46 shows fluorescence anisotropies for apo-N67C-ABD-T (excitation 430 nm, emission at 550 nm) as a function of the concentration of Cu(II) (◇), Zn(II) (♦), Cd(II) (○), Co(II) (●) and Ni (II) (△).

Since the average lifetime of apo-N67C-ABD-T ($<\tau>$= 11.98 nsec) is comparable to the rotational correlation time of carbonic anhydrase ($\theta_c$=15 nsec), we might anticipate a significant change in the fluorescence anisotropy upon binding of the metal due to the decline in average lifetime; the success of the approach depends in part on the degree of independent motion of the label. In fact it works quite well in this case, as determined by the metal-dependent anisotropies FIG. 46. In particular, the anisotropy of the apoCA increases approximately 50% in most cases upon binding, a change that is readily measurable inasmuch as the ordinary accuracy and precision of anisotropy measurements is ±0.002.

All references cited herein are hereby incorporated by reference in their entirety. While the invention has been described in detail, and with reference to specific embodiments thereof, it will be apparent to one of ordinary skill in the art that various changes and modifications can be made therein without departing from the spirit and scope thereof.

What is claimed:

1. A photoluminescent sensor for use the detection of a metal ion in an aqueous sample, said metal ion selected from the group consisting of Zn(II), Cu(II), Co(II), Ni(II), and Cd(II), said sensor comprising a macromolecule having a metal ion binding site, said macromolecule selected from the group consisting of human apocarbonic anhydrase, F131C variant of human apocarbonic anhydrase, and N67C variant of human apocarbonic anhydrase, said macromolecule having a photoluminescent label covalently bound thereto, said label selected from the group consisting of PyMPO, 1-[[(2', 7'-difluoro-3',6'-dihydroxy-3-oxospiro[isobenzofuran-1 (3H),9'-[9H]xanthen]-5-yl)carbonyl]oxy]-2,5-pyrrolidinedione, and ABD-T.

2. The sensor of claim 1 wherein said metal ion partially quenches the fluorescence of said label in a proximity dependent manner.

3. The sensor of claim 1 wherein said metal ion does not quench the fluorescence of said label.

4. A photoluminescent sensor for use the detection of a metal ion in an aqueous sample, said metal ion selected from the group consisting of Zn(II), Co(II), and Cd(II),, said sensor comprising a macromolecule having a metal ion binding site selected from the group consisting of human apocarbonic anhydrase, Q92A variant of human apocarbonic anhydrase, E117A variant of human apocarbonic anhydrase, E117D variant of human apocarbonic anhydrase, and E117Q variant of human apocarbonic anhydrase, said macromolecule having a photoluminescent label non-covalently bound thereto or associated therewith, said label selected from the group consisting of dapoxyl sulfonamide, ABD-N, ABD-M, and BTCS.

5. The sensor of claim 4 wherein said metal ion partially quenches the fluorescence of said label in a proximity dependent manner.

6. The sensor of claim 4 wherein said metal ion does not quench the fluorescence of said label.

* * * * *